US007105647B1

(12) United States Patent
Bradfield et al.

(10) Patent No.: US 7,105,647 B1
(45) Date of Patent: Sep. 12, 2006

(54) CDNAS AND PROTEINS INVOLVED IN HYPOXIA, CIRCADIAN AND ORPHAN SIGNAL TRANSDUCTION PATHWAYS, AND METHODS OF USE

(75) Inventors: Christopher A. Bradfield, Madison, WI (US); Yi Zhong Gu, Sunnyvale, CA (US); John B. Hogenesch, San Diego, CA (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 09/555,362

(22) PCT Filed: Nov. 27, 1998

(86) PCT No.: PCT/US98/25314

§ 371 (c)(1), (2), (4) Date: Jul. 24, 2000

(87) PCT Pub. No.: WO99/28464

PCT Pub. Date: Jun. 10, 1999

Related U.S. Application Data

(60) Provisional application No. 60/066,863, filed on Nov. 28, 1997.

(51) Int. Cl.
*C07H 21/02* (2006.01)

(52) U.S. Cl. .................. 536/23.1; 536/23.4; 536/23.5; 424/93.1

(58) Field of Classification Search ............... 536/23.1, 536/23.4, 23.5, 24.31; 424/93.1
See application file for complete search history.

(56) References Cited

U.S. PATENT DOCUMENTS

| | | | | |
|---|---|---|---|---|
| 5,650,283 A | 7/1997 | Bradfield et al. | ............ | 435/7.1 |
| 5,695,963 A | 12/1997 | McKnight et al. | ......... | 435/69.1 |

OTHER PUBLICATIONS

Genbank accession No. U51627, human MOP3 Apr. 12, 1997.*
Genbank accession No. H17840, EST 27778, Jun. 29, 1995.*
Genbank accession No. T77200, EST 139563, Mar. 6, 1995.*
Hogenesch et al. JBC 272(13):8581-8593, Mar. 28, 1997.*
Ikeda et al. BBRC 233:258-264, 1997.*
Saunier et al. App Envir. Micro 62(7):2360-2374, Jul. 1996.*
Strauchen et al. Am J. Pathol 123(2) Pubmed abstract, May 1986.*
Goyert et al. J. Immunol 137(12) Pubmed abstract, Dec. 15, 1986.*
Allada, Ravi et al., A Mutant *Drosophila* Homolog of Mammalian Clock Disrupts Circadian Rhythms and Transcription of period and timeless, Cell 93:791-804 (1998).
Antoch, Marina P. et al., Functional Identification of the Mouse Circadian Clock Gene by Transgenic BAC Rescue, Cell 89:655-667 (1997).
Atchley, William R. and Fitch, Walter M. , A natural classification of the basic helix-loop-helix class of transcription factors, Proc. Natl. Acad. Sci. USA 94:5172-5176 (1997).
Antonsson, Camilla et al., Constitutive Function of the Basic Helix-Loop-Helix/PAS Factor Arnt, The Journal of Biological Chemistry 270:13968-13972 (1995).
Burbach, Kristine M. et al., Cloning of the Ah-receptor cDNA reveals a distinctive ligand-activated transcription factor, Proc. Natl. Acad. Sci. USA 89:8185-8189 (1992).
Carver, Lucy A. and Bradfield, Christopher A., Ligand-dependent Interaction of the Aryl Hydrocarbon Receptor with a Novel Immunophilin Homolog in Vivo, The Journal of Biological Chemistry 272:11452-11456 (1997).
Carver, Lucy A. et al., Tissue specific expression of the rat Ah-receptor and ARNT mRNAs, Nucleic Acid Research 22:3038-3044 (1994).
Carver, Lucy A. et al., The 90-kDa Heat Shock Protein Is Essential for Ah Receptor Signaling in a Yeast Expression System, The Journal of Biological Chemistry 269:30109-30112 (1994).
Carver, Lucy A. et al., Characterization of the Ah Receptor-associated Protein, ARA9, The Journal of Biological Chemistry 273:33580-33587 (1998).
Chan, William K. et al., Baculovirus Expression of the Ah Receptor and Ah Receptor Nuclear Translocater, The Journal of Biological Chemistry 269:26464-26471 (1994).
Darlington, Thomas K. et al., Closing the Circadian LoopL CLOCK-Induced Transcription of Its Own Inhibitors per and tim, Science 280:1599-1603 (1998).
Dolwick, Kristine M. et al., Cloning and Expression of a Human Ah Receptor cDNA, Molecular Pharmacology 44:911-917 (1993).
Dolwick, Kristine M. et al. In vitro analysis of Ah receptor domains involved in ligand-activated DNA recognition, Proc. Natl. Acad. Sci USA 90:8566-8570 (1993).
Dunlap, Jay, Circadian Rhythms: An End in the Beginning, Science 280:1548-1549 (1998).
Ema, Masatsugu et al., A novel bHLH-PAS factor with close sequence similarity to hypoxia-inducible factor 1α regulates the VEGF expression and is potentially involved in lung and vascular development, Proc. Natl. Acad. Sci. USA. 94:4273-4278 (1997).
Ema, Masatsugu et al., Two New Members of the Murine Sim Gene Family Are Transcriptional Repressors and Show Different Expression Patterns during Mouse Enbryogenesis, Molecular and Cellular Biology 16:5865-5875 (1996).

(Continued)

*Primary Examiner*—Joseph Woitach
(74) *Attorney, Agent, or Firm*—Woodcock Washburn LLP

(57) ABSTRACT

The present invention provides isolated nucleic acids and proteins that are new and distinct members of the bHLH-PAS superfamily of transcription regulators. These "MOPs" (members of PAS) are useful in a variety of research, diagnostic and therapeutic applications. Several of the MOPs of the present invention are α-class hypoxia-inducible factors. Several other of the MOPs of the invention are involved in circadian signal transduction.

10 Claims, 8 Drawing Sheets

OTHER PUBLICATIONS

Enan, Essam and Matsumara, Fumio, Identification of c-Src as the Integral Component of the Cytosolic Ah Receptor Complex, Transducing the Signal of 2,3,7,8-Tetrachlorodibenzo-p-dioxin (TCDD) Through the Protein Phosphorylation Pathway, Biochemical_Pharmacology 52:1599-1612 (1966).

Gekakis, Nicholas et al., Isolation of timeless by PER Protein Interaction: Defective Interaction Between timeless Protein and Long-Period Mutant PER, Science 270:811-815 (1995).

Gekakis, Nicholas et al., Role of the CLOCK Protein in the Mammalian Circadian Mechanism, Science 280:1564-1569 (1998).

Golemis, Erica A. et al., Interaction Trap/Two-Hybrid System to Identify Interacting Proteins, Current Protocols in Molecular Biology 20.1.1-20.1.35 (1997).

Hirose, Ken et al., cDNA Cloning and Tissue-Specific Expression of a Novel Basic Helix-Loop-Helix/PAS Factor (Arnt2) with Close Sequence Similarity to the Aryl Hydrocarbon Receptor Nuclear Translocator (Arnt), Molecular and Cellular Biology 16:1706-1713 (1996).

Hogenesch, John B. et al., The basic-helix-loop-helix-PAS orphan MOP3 forms transcriptionally active complexes with circadian and hypoxia factors, Proc. Natl. Acad. Sci. USA 95:5474-5479 (1998).

Hogenesch, John B. et al., Characterization of a Subset of the Basic-Helix-Loop-Helix-PAS Superfamily That Interacts with Components of the Dioxin Signaling Pathway, The Journal of Biological Chemistry 272:8581-8593 (1997).

Ikeda, Masaaki and Nomura, Masahiko, cDNA Cloning and Tissue-Specific Expression of a Novel Basic Helix-Loop-Helix/PAS Protein (BMAL1) and Identification of Alternatively Spliced Variants with Alternative Translation Initiation Site Usage, Biochemical and Biophysical Research Communications 233:258-264 (1997).

Jain, Sunjay et al., Potent Transactivation Domains of the Ah Receptor and the Ah Receptor Nuclear Translocator Map to Their Carboxyl Termini, The Journal of Biological Chemistry 269:31518-31524 (1994).

King, David P. et al., Positional Cloning of the Mouse Circadian Clock Gene, Cell 89:641-653 (1997).

LeBeau, M.M. et al., Chromosomal location of the human AHR locus encoding the structural gene for the Ah receptor to 7p21→p15, Cytogenetics and Cell Genetics 66:172-176 (1994).

Ma, Qiang and Whitlock, Jr., James P., A Novel Cytoplasmic Protein That Interacts with the Ah Receptor, Contains Tetratricopeptide Repeat Motifs, and Augments the Transcriptional Response to 2,3,7,8-Tetrachlorodibenzo-p-dioxin, The Journal of Biological Chemistry 272:8878-8884 (1997).

Maltepe, Emin et al., Abnormal angiogenesis and responses to glucose and oxygen deprivation in mice lacking the protein ARNT, Nature 386:403-407 (1997).

Meyer, Brian K. et al., Hepatitis B Virus X-Associated Protein 2 Is a Subunit of the Unliganded Aryl Hydrocarbon Receptor Core Complex and Exhibits Transcriptional Enhancer Activity, Molecular and Cellular Biology 18:978-988 (1998).

Pollenz, Richard S. et al., Isolation and Expression of cDNAs from Rainbow Trout (*Oncorhynchus mykiss*) That Encode Two Novel Basic Helix-Loop-Helix/PER-ARNT-SIM (bHLH/PAS) Proteins with Distinct Functions in the Presence of the Aryl Hydrocarbon Receptor, Journal of Biological Chemistry 271:30886-30896 (1996).

Rutila, Joan E. et al., CYCLE Is a Second bHLH-PAS Clock Protein Essential for Circadian Rhythmicity and Transcription of *Drosophila* period and timeless, Cell 93:805-814 (1998).

Schmidt, Jennifer V. et al., Characterization of a murine Ahr null allele: Involvement of the Ah receptor in hepatic growth and development, Proc. Natl. Acad. Sci. USA 93:6731-6736 (1996).

Schmidt, Jennifer V. and Bradfield, Christopher A., Ah Receptor Signaling Pathways, Annu. Rev. Cell Dev. Biol. 12:55-89 (1996).

Schmidt, Jennifer V. et al. ,Molecular Characterization of the Murine Ahr Gene, The Journal of Biological Chemistry 268:22203-22209 (1993).

Tian, Hui et al., Endothelial PAS domain protein 1 (EPAS1), a transcription factor selectively expressed in endothelial cells, Genes & Development 11:72-82 (1997).

Vaziri, Cyrus et al., Expression of the Aryl Hydrocarbon Receptor Is Regulated by Serum and Mitogenic Growth Factors in Murine 3T3 Fibroblasts, The Journal of Biological Chemistry 271:25921-25927 (1996).

Wang, Guang L. et al., Hypoxia-inducible factor 1 is a basic-helix-loop-helix-PAS heterodimer regulated by cellular $O_2$ tension, Proc. Natl. Acad. Sci. USA. 92:5510-5514 (1995).

Zhou, Yu-Don't et al., Molecular characterization of two mammalian bHLH-PAS domain proteins selectively expressed in the central nervous system, Proc. Natl. Acad. Sci. USA. 94:713-718 (1997).

* cited by examiner

```
1 MEGAGGANDKKKISSER MOP1
1 MTADKEKKRSSSER MOP2
1 MSKEAVSLWALTVSLQPPVPLCVCREMTGSGRRKQQCVTLPFISRELCFYLLLFPPPRLEYTEHQGGIKN MOP3
1 ..MDEDEKDRA MOP4
1 NSRRPALRAAAAGARPAGGPSGSQPPEQH MOP5

18  RKEKSRDAARSRRSKESEVFYELAHQLPLPHNVSSHLDKASVMRLTISYLRVRKLLDA-- MOP1
15  RKEKSRDAARCRRSKETEVFYELAHELPLPHSVSSHLDKASIMRLAISFLRTHKLLSSVC MOP2
71  AREAHSQIEKRRRDKMNSFIDELASLVPTCNAMSRKLDKLTVLRMAVQHMKTLRGATNPY MOP3
9   KRASRNKSEKKRRDQFNVLIKELSSMLP---GNTRKMDKTTVLEEVIGFLQKHNEVSAQT MOP4
29  ------------------------------------------------------------ MOP5
    basic region          helix-loop-helix

76  GDLDIEDD------MKAQMNCFYLKALDGFVMVLTDD-GDMIYISDNVNKYMGLTQFELT MOP1
75  SENESEAE------ADQQMDNLYLKALEGFIAVVTQD-GDMIFLSENISKFMGLTQVELT MOP2
131 T----EANYKPIFLSDDELKHLILRAADGFLFVVGCDRGKILFVSESVFKILNYSQNDLI MOP3
66  EICDIQQDWKPSFLSNEEFTQLMLEALDGFIIAVTTD-GSIIYVSDSITPLLGHLPSDVM MOP4
34  -----------------LGGHILQSLDGFVFALNQE-GKFLYISETVSIYLGLSQVEMT MOP5
                                          A-repeat

129 GHSVFDFTHPCDHEEMREMLTHR---------------------NG--LVKKGKEQNT- MOP1
128 GHSIFDFTHPCDHEEIRENLSLK---------------------NGSGFGKKSKDMST- MOP2
187 GQSLFDYLHPKDIAKVKEQLSSSDTAPRERLIDAKTGLPVKTDITPGPSRLCSGARRSFF MOP3
125 DQNLLNFLPEQEHSEVYKILSS------HMLVTD----------SPSPEYLKSDGDLEFY MOP4
70  GSSVFDYIHPGDHSEVLEQLGLRIPTP-----GPPTPPSVSSSSSSSSSLADTPEIEASL MOP5

164 --------------QRSF----FLRMKCTLTSRGRTMNIKSATW-KVLHCTGHIHVYDT-N MOP1
165 --------------ERDF----FMRMKCTVTNRGRTVNLKSATW-KVLHCTGQVKVYNNCP MOP2
247 CRMKCNRPSVKVEDKDFPS-TCSKKKADRKSFCTIHST---GYLKSWP-PTKMGLDEDNE MOP3
169 CHLL----RGSLNPKEFPTYEYIKFVGNFRSYNNVPSPSCNGFDNTLSRPCRVPLGKE-- MOP4
125 TKV---PPSSLVQERSF----FVRMKSTLTKRG--LHVKASGY-KVIHVTGRLRAHA--- MOP5

205 SNQPQCGYKKPPMTCLVLIC----EPIPHPSNIEIPLDS--KTFLSRHSLDMKFSYCDER MOP1
207 PHNSLCGYKEPLLSCLIIMC----EPIQHPSHMDIPLDS--KTFLSRHSMDMKFTYCDDR MOP2
302 PDNEGCN-----LSCLVAIGRLHSHVVPQPVNGEIRVKSM--EYVSRHAIDGKFVFVDQR MOP3
223 --------------VCFIATVRLAT---PQFLKEMCIVDEPLEEFTSRHSLEWKFLFLDHR MOP4
172 -------------LG-LVALG----HTLPPAPLAELPLHG--HMIVFRLSLGLTILACESR MOP5

259 ITELMGYEPEELLGRSIYEYYHALDSDHLTKTHHDMFT-KGQVTTGQYRMLAKRGGYVWV MOP1
261 ITELIGYHPEELLGRSAYEFYHALDSENMTKSHQNLCT-KGQVVSGQYRMLAKHGGYVWL MOP2
355 ATAILAYLPQELLGTSCYEYFHQDDIGHLAECHRQVLQTREKITTNCYKFKIKDGSFITL MOP3
267 APPIIGYLPFEVLGTSGYDYYHIDDLELLARCHQHLMQF-GKGKSCCYRFLTKGQQWIWL MOP4
213 VSDHMDLGPSELVGRSCYQFVHGQDATRIRQSHVDLLD-KGQVMTGYYRWLQRAGGFVWL MOP5
            B-repeat

318 ETQATVIYNTKNSQPQCIVCVNYVVSGIIQHDLIFSLQQTECVLKPVESSDMKMTQLFTK MOP1
320 ETQGTVIYNPRNLQPQCIMCVNYVLSEIEKNDVVFSMDQTESLFKPHLMAMNSIFDSSGK MOP2
415 RSRWFSFMNPWTKEVEYIVSTNTVVLANVLEGGDPTFPQLTASPHSMDSMLPSGEGGPKR MOP3
326 QTHYYITYHQWNSKPEFIVCTHSVVSYADVRVERRQELALEDPPSEALHSSALKDKGSSL MOP4
272 QSVATVAGSGKSPGEHHVLWVSHVLSQAEGGQTPLDAFQLPASVACEEASSPGPEPTEPE MOP5

378 VESEDTSSLFDKLKKEPDALTLLAPAAGDTIISLDFGSNDTETDDQQLEEVPLYNDVMLP MOP1
380 GAVSEKSNFLFTKLKEEPEELAQLAPTPGDAIISLDFGNQNFEESSAYGKAILPPSQPWA MOP2
475 THPTVPGIPGGTRAGAGKIGRMIAEEIMEIHRIRGSLRSSCGSSPLNITSTPPPDASSPG MOP3
386 EPRQHFNALDVGASGLNTSHSPSASSRSSHKSSHTAMSEPTSTPTKLMAEASTPALPRSA MOP4
332 PPTEGKQAAPAENEAPQTQGKRIKVEPGPRETKGSEDSGDEDPSSHPATPRPEFTSVIRA MOP5

438 SPNEKLQNINLAMSPLPTAETPKPLRSSADPALNQEVALKLEPNPESLELSFTMPQIQDQ MOP1
440 TELRSHSTQSEAGSLPAFTVPQAAAPGSTTPSATSSSSSCSTPNSPEDYYTSLDNDLKIE MOP2
535 GKKILNGGTPDIPSSGLLSGQAQENPGYPYSDSSSILGENPHIGIDMIDNDQGSSSPSND MOP3
446 TLPQELPVPGLSQAATMPAPLPSPSSCDLTQQLLPQTVLQSTPAPMAQFSAQFSMFQTIK MOP4
392 GVLKQDPVRPWGLAPPGDPPPTLLHAGFLPPVVRGLCTPGTIRYGPAELGLVYPHLQRLG MOP5

498 TPSPSDGSTRQSSPEPNSPSEYCFYVDSDMVNEFKLELVEKLFAEDTEAKNPFSTQDTDL MOP1
500 VIEKLFAMDTEAKDQCSTQTDFNELDLETLAPYIPMDGEGFQLSPICPEERLLAENPQST MOP2
595 EAAMAVIMSLLEADAGLGGPVDFSDLPWPL• MOP3
506 DQLEQRTRILQANIRWQQEELHKIQEQLCLVQDSNVQMFLQQPAVSLSFSSTQRPEAQQQ MOP4
452 PGPALPEAFYPPLGLPYPGPAGTRLPRKGD• MOP5

558 DLEMLAPYIPMDDDFQLRSFDQLSPLESSSASPESASPQSTVTVFQQTQIQEPTANATTT MOP1
560 PQHCFSAMTNIFQPLAPVAPHSPFLLDKFQQQLESKKTEPERRPMSSIFFDAGSKASLPP MOP2
566 LQQRSAAVTQPQLGAGPQLPGQISSAQVTSQHLLRESSVISTQGPKPMRSSQLMQSSGRS MOP4

618 TATTDELKTVTKDRMEDIKILIASPSPTHIHKETTSATSSPYRDTQSRTASPNRAGKGVI MOP1
620 CCGQASTPLSSMGGRSNTQWPPDPPLHFGPTKWAVGDQRTEFLGAAPLGPPVSPPHVSTF MOP2
626 IPAERRSLPLPVGLVS... MOP4

678 EQTEKSHPRSPNVLSVALSQRTTVPEEELNPKILALQNAQRKRKMEHDGSLFQAVGIGTL MOP1
680 KTRSAKGFGARGPNVLSPAMVALSNKLKLKRQLEYEKQAFQDPSGGDPPGGSTSHLMWKR MOP2

738 LQQPDDHAATTSLSWKRVKGCKSSEQNGMEQKTIILIPSDLACRLLGQSMDESGLPQLTS MOP1
740 MKNLRGGSCPLMPDKPLSANVPNDKLTQNSMRGLGHPLRHLPLPQPPSAISPGENSKSRF MOP2

798 YDCEVNAPIQGSRNLLQGEELLRALDQVN• MOP1
800 PPQCYATQYQDYSLSSAHKVSGMASRLLGPSFESYLLPELTRYDREVKVPVLGSSTLLQG MOP2

860 GDLLRALDQATM• MOP2
```

FIG. 2

| | | | | | | | | | | | | | |
|---|---|---|---|---|---|---|---|---|---|---|---|---|---|
| g | g | G | G | C | A | C | G | T | G | A | C | A | C |
| G | G | T | A | C | A | C | G | T | G | A | C | C | c |
| t | g | a | a | C | A | C | G | T | G | A | C | C | C |
| t | g | a | a | C | A | C | G | T | G | A | C | T | C |
| g | g | G | C | C | A | C | G | T | G | A | C | C | T |
| G | G | G | A | C | A | C | G | T | G | A | C | C | g |
| c | T | A | A | C | A | C | G | T | G | A | C | C | G |
| g | a | a | c | C | A | C | G | T | G | A | G | C | T |
| t | g | a | a | C | A | C | G | T | G | A | C | A | C |
| g | G | G | T | C | A | C | G | T | G | A | C | T | C |
| G/T | G | A/G | A | C | A | C | G | T | G | A | C | C | C |
| −7 | −6 | −5 | −4 | −3 | −2 | −1 | +1 | +2 | +3 | +4 | +5 | +6 | +7 |

FIG. 5

LexAbHLH–PAS "Bait"

| Full Length "Fish" | HIF1α | HIF2α | MOP3 | MOP4 | AHR | ARNT | CLOCK | LEXA |
|---|---|---|---|---|---|---|---|---|
| MOP3 | + | ++ | – | ++ | – | – | ++ | – |
| ARNT | + | ++ | – | – | ++ | – | – | – |

FIG. 6

CDNAS AND PROTEINS INVOLVED IN HYPOXIA, CIRCADIAN AND ORPHAN SIGNAL TRANSDUCTION PATHWAYS, AND METHODS OF USE

Pursuant to 35 U.S.C. §371, this is a national stage of International Application No. PCT/US98/25314, filed Nov. 27, 1998 and claiming benefit of U.S. Provisional Application No. 60/066,863, filed Nov. 28, 1997, the entireties of each of which are incorporated by reference herein.

Pursuant to 35 U.S.C. §202(c), it is acknowledged that the U.S. Government has certain rights in the invention described herein, which was made in part with funds from the National Institutes of Health, Grant Nos. P30-CA07175 and ES05703.

FIELD OF THE INVENTION

This invention relates to the field of molecular signaling and physiological responses to external stimuli. In particular, this invention provides nucleic acid molecules and proteins that constitute new members of the bHLH-PAS superfamily of transcription regulators.

BACKGROUND OF THE INVENTION

Several publications are referenced in this application to describe the state of the art to which the invention pertains. Each of these publications is incorporated by reference herein.

The aryl hydrocarbon receptor (AH receptor or AHR), AH receptor nuclear transporter (ARNT), *Drosophila* single-minded gene product (SIM) and *Drosophila* period gene product (PER) are the founding members of an emerging superfamily of regulatory proteins. The AHR and ARNT are heterodimeric partners that transcriptionally upregulate genes involved in the metabolism of xenobiotics. The AHR is activatable by a number of widespread environmental pollutants like 2,3,7,8-tetrachlorodibenzo-p-dioxin (TCDD). In the absence of agonist, the AHR is primarily cytosolic and functionally repressed, presumably as the result of its tight association with Hsp90. Current models suggest that agonist binding initiates translocation of the receptor complex to the nucleus and concomitantly weakens the AHR-Hsp90 association. Within the nucleus, Hsp90 is displaced and the AHR dimerizes with its partner ARNT resulting in a bHLH-PAS heterodimer with binding specificity for DNA sequences within enhancer elements upstream of gene products that metabolize foreign chemicals. In *Drosophila*, SIM is master regulator of midline cell lineage in the embryonic nervous system. In vitro and in vivo studies suggest that SIM may also dimerize with an ARNT-like protein to regulate enhancer sequences present in the sim, slit and Toll structural genes. The *Drosophila* PER protein plays a role in the maintenance of circadian rhythms. PER has been shown to form heterotypic interactions with a second *Drosophila* protein, TIM, in vivo, and homotypic interactions with the ARNT molecule in vitro.

The distinguishing characteristic of these proteins is a 200–300 stretch of amino acid sequence similarity known as a PAS (PER/ARNT/SIM) domain. In the AHR, the PAS domain has been shown to encode sites for agonist binding, surfaces to support heterodimerization with other PAS domains, as well as surfaces that form tight interactions with Hsp90. In addition to the PAS domain, the AHR, ARNT and SIM also harbor a bHLH (basic helix-loop-helix) motif that plays a primary role in dimer formation. The bHLH motif is found in a variety of transcription factors that utilize homotypic interactions to regulate various aspects of cell growth and differentiation. Dimerization specificity is dictated by sequences within both the bHLH and determinants within secondary interaction surfaces, such as the "leucine zipper or PAS domains. Interestingly, these dimerization surfaces also appear to restrict pairing to within a given bHLH protein superfamily, thus minimizing crosstalk between important cellular pathways.

Because other bHLH protein families utilize multiple homotypic interactions to provide fine control in the regulation of certain gene batteries, it is possible that additional bHLH-PAS proteins exist in the mammalian genome and that a subset of these proteins might dimerize with either the AHR or ARNT. However, prior to the present invention, the AHR and ARNT were the only mammalian bHLH-PAS proteins that had been identified. Accordingly, a need exists to identify and characterize other bHLH-PAS domain proteins, particularly those that are novel receptors for drugs, or are AHR or ARNT binding partners. Such molecules would find broad utility as research tools in elucidating environmentally and developmentally controlled signal transduction pathways, and also as diagnostic and therapeutic agents for detection and control of such pathways.

SUMMARY OF THE INVENTION

This invention provides isolated nucleic acids and proteins which are new and distinct members of the bHLH-PAS superfamily of transcription regulators. These "MOPs" (members of PAS) are useful for a wide variety of research, diagnostic and therapeutic applications, as described in greater detail herein.

According to one aspect of the invention, isolated nucleic acid molecules are provided that include an open reading frame encoding a protein selected from the group consisting of: MOP2, MOP3, MOP4, MOP5, MOP6 MOP7, MOP8 and MOP9. In preferred embodiments, the open reading frame encodes a protein having an amino acid sequence substantially the same as a sequence selected from the group consisting of SEQ ID NO:11, SEQ ID NO:12, SEQ ID NO:13, SEQ ID NO:14, SEQ ID NO:15, SEQ ID NO:16 SEQ ID NO:17 and SEQ ID NO:18. The nucleic acid molecules of the invention preferably comprise sequences substantially the same as a sequence selected from the group consisting of SEQ ID NO:2, SEQ ID NO:3, SEQ ID NO:4, SEQ ID NO:5, SEQ ID NO:6, SEQ ID NO:7 SEQ ID NO:8 and SEQ ID NO:9.

According to another aspect of the invention, isolated MOP proteins are provided, which are products of expression of part or all of the open reading frames of the aforementioned nucleic acid molecules.

According to another aspect of the invention, recombinant DNA molecules are provided, which comprise MOP encoding nucleic acid molecules, operably linked to vectors for transforming cells. Cells transformed with those recombinant DNA molecules are also provided, as well as cellular assay systems utilizing those recombinant molecules.

According to another aspect of the invention, oligonucleotides between about 10 and about 100 nucleotides in length are provided, which specifically hybridize with portions of the MOP-encoding nucleic acid molecules.

According to another aspect of the invention, antibodies are provided which are immunologically specific for part or all of any of the MOP2-MOP8 proteins of the invention.

According to another aspect of the invention, assays and other methods of using the aforementioned MOP nucleic acids, proteins and immunospecific antibodies are provided.

BRIEF DESCRIPTION OF THE DRAWINGS

FIG. 2. Amino acid sequence and multiple alignment of the PAS domains of MOP1 (SEQ ID NO:10), MOP2 (SEQ ID NO:11), MOP3 (SEQ ID NO:12), MOP4 (SEQ ID NO:13) and MOP5 (SEQ ID NO:14). The amino acid sequence including a CLUSTAL alignment of the bHLH-PAS domains is depicted. The CLUSTAL alignment was performed using the MEGALIGN program (DNASTAR, Madison, Wis.) with a PAM250 weight table using the following parameters: Ktuple=1, Gap Penalty=3, Window=5. Amino acid boundaries for the residues encompassing the bHLH and PAS domains of the MOPs were defined based on previous observations. The bHLH domain is boxed, while the basic region is specified by a vertical line. The PAS domain is underlined, while the "A" and "B" repeats of the PAS domain are boxed. Consensus (60%) residues in the PAS domain are denoted with an asterisk.

FIG. 3. Yeast two-hybrid analysis. In vivo interaction of MOPs with dioxin signaling pathway.

FIG. 5. The consensus DNA binding site for MOP3-MOP4 heterodimer in vitro. Ten selected DNA sequences bound by the MOP3-MOP4 complex are indicated with the E-box core boxed (from top to bottom, SEQ ID NOS: 110, 111, 112, 113, 114, 115, 116, 117, 118 and 119). Underneath, the M34 consensus is indicated (SEQ ID NO:120). Nucleotide positions relative to the E-box core are shown. Bases in uppercase are randomer derived, while bases in lower case are primer derived.

FIG. 6. Interaction panel of LexAbHLH-PAS fusion proteins with full-length MOP3 and ARNT. FIG. 6A: Schematic representation of the LexAbHLHPAS "bait" and the full-length "fish." The bHLH and PAS domains are boxed. The "A" and "B" repeats of the PAS domains are indicated. The transactivation domain of the full-length "fish" is indicated. FIG. 6B: LexA fusion protein plasmids containing the bHLH-PAS domains of HIF1α, HIF2α, MOP3, MOP4, AHR, ARNT, and CLOCK were coexpressed with plasmids harboring full-length MOP3 and ARNT (see Materials and Methods). LexAAHR interactions were assayed on plates containing 1 μM β-naphthoflavone. After incubation, an 5-bromo-4-chloro-3-indolyl 13-β-galactoside overlay assay was performed. ++, A strong interaction, turning blue within 2 hr; +, a weaker interaction, turning blue between 8 hr and overnight; and –, a negative interaction after overnight incubation. The experiment was performed three times with identical results.

DETAILED DESCRIPTION OF THE INVENTION

I. Definitions

Figure 1:
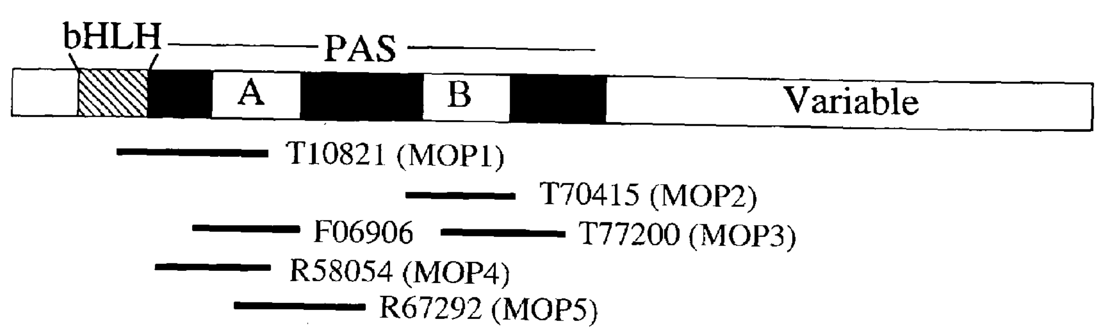
FIG. 1. Schematic representation of a generic bHLH-PAS member and the corresponding region where EST "hits" occurred. Top, schematic of a generic bHLH-PAS family member. The hatched box represents the bHLH region, the overlined area represents the PAS domain with the characteristic "A" and "B" repeats in white. The variable C terminus is boxed in white. A bold line representing the region in a generic bHLH-PAS member where the homology occurs is indicated next to the original Gen Bank™ accession number for each identified EST (MOP1=T10821, MOP2=T70415, MOP3=T77200 and F06906, MOP4=R58054, MOP5=R67292; see Table 1).

Various terms relating to the biological molecules of the present invention are used hereinabove and also throughout the specifications and claims. The terms "substantially the same," "percent similarity" and "percent identity" are defined in detail below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest, but which do not substantially recognize and bind other molecules in a sample containing a mixed population of antigenic biological molecules.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "promoter region" refers to the transcriptional regulatory regions of a gene. In the present invention, the use of SV40, TK, Albumin, SP6, T7 gene promoters, among others, is contemplated.

The term "selectable marker gene" refers to a gene encoding a product that, when expressed, confers a selectable phenotype such as antibiotic resistance on a transformed cell.

The term "reporter gene" refers to a gene that encodes a product which is easily detectable by standard methods, either directly or indirectly.

The term "operably linked" means that the regulatory sequences necessary for expression of the coding sequence are placed in the DNA molecule in the appropriate positions relative to the coding sequence so as to enable expression of the coding sequence. This same definition is sometimes applied to the arrangement of transcription units and other transcription control elements (e.g. enhancers) in an expression vector.

II. Characterization of MOPS 1–9

Our hypothesis in accordance with the present invention was that additional bHLH-PAS proteins are encoded in the mammalian genome and that some of these proteins are involved in mediating the pleiotropic response to potent AHR agonists like TCDD. It has been observed that other bHLH superfamilies employ multiple dimeric partnerships to control complex biological processes, such as myogenesis (MyoD/myogenin), cellular proliferation (Myc, Max, Mad) and neurogenesis (achaete-scute/daughterless). The observation that bHLH proteins often restrict their dimerization to within members of the same gene family (i.e., "homotypic interactions") and that this restriction may occur as the result of constraints imposed by both primary (e.g., bHLH) and secondary dimerization surfaces (e.g., leucine zippers and PAS), prompted us to screen for additional bHLH-PAS proteins and test each protein for its capacity to interact with either the AHR or ARNT. The ultimate objective was to identify MOPs that were physiologically relevant partners of either the AHR or ARNT in vivo. Our prediction was that such proteins might respond to or modulate the AHR signaling pathway or other signaling pathways involving ARNT.

To rapidly identify expressed genes, the "expressed sequence tag" (EST) approach was developed, whereby a cDNA library is constructed and randomly selected clones are sequenced from both vector arms (Adams et al., Science 252: 1651–1656, 1991). These partial sequences, generally 200–400 bp, are deposited in a number of computer databases that can be readily analyzed using a variety of search algorithms. As of 1996, the I.M.A.G.E. Consortium has deposited over 300,000 human ESTs, generated from different tissues and developmental time periods into publicly accessible databases, identifying approximately 40,000 unique cDNA clones (Lennon et al., Genomics 33: 151–152, 1996). The availability of these sequences and plasmids harboring their corresponding cDNA clones provided a means by which to identify novel members of the bHLH-PAS family by nucleotide homology screening of available EST databases.

At the time this invention was initiated, the human AHR and ARNT and the *drosophila* SIM and PER were the only PAS protein that had been described. Therefore, we used the nucleotide sequences encoding their PAS domains as query sequences in BLASTN searches of the available EST databases. Using this strategy in an iterative fashion and confirming each hit with a reverse BLASTX search, we have identified eight cDNAs referred to herein as members of the PAS superfamily, or "MOPs". Using PCR, we were able to obtain the complete ORFs of MOPs 1–4, and extensive but incomplete ORFs of MOP5. We have also identified four more MOPs, MOPs 6, 7, 8 and 9, and obtained their complete ORFs.

While MOPs 1–5 were being characterized, Wang and colleagues identified two factors involved in cellular response to hypoxia, HIF1α and HIF1β. These proteins are identical to MOP1 and ARNT, respectively (Wang et al., Proc. Natl. Acad. Sci. USA 92: 5510–5514, 1995). Thus, of the nine MOPs we have cloned, seven have not been previously characterized. For consistency herein, we describe MOP1 extensively, and describe heretofore undisclosed methods of using MOP1.

The experimental approach taken in accordance with the present invention has significantly expanded the number of known members of the emerging bHLH-PAS superfamily of transcriptional regulators. Along with the MOPs described herein, five additional mammalian bHLH-PAS proteins have been identified, HIF1α (MOP1, as described above), SIM1, SIM2, ARNT2, and SRC-1 (Wang et al., 1995, supra; Hirose et al., Mol. Cell. Biol. 16: 1706–1713, 1996; Fan et al., Mol. Cell. Neurosci. 7: 1–16, 1996; Ema et al., Mol. Cell. Biol. 16: 5865–5875, 1996; Chen et al., Nat. Genet. 10: 9–10, 1995; and Kamei et al., Cell 85: 403–414, 1996). To compare amino acid sequences of these proteins, we performed a CLUSTAL alignment with the bHLH-PAS domains of MOPs 1–5 and all the known family members using a PAM250 residue weight table (Higgins & Sharp, Gene (Amst.) 73: 237–244, 1988). The two most related members were MOP1/HIF1α and MOP2, which shared 66% identity in the PAS domain. A comparison of these two proteins reveals only a single amino acid difference in the basic region and 83% identity in the HLH region. This sequence similarity is in agreement with our contention (discussed in Example 1) that MOP1/HIF1α and MOP2 function analogously, interacting with the same heterodimeric partners and binding similar enhancer sequences in vivo. A comparison of MOP3 and ARNT and a comparison of MOP5 and SIM reveal 40% and 38% identity in the PAS domain, respectively. The basic regions of MOP3 and ARNT have only three substitutions, while the HLH domains share 66% identity, again suggesting that the two proteins may regulate similar or identical enhancer sequences (half sites).

A CLUSTAL alignment of the C-termini of MOPs 1–5 and the previously identified PAS members demonstrated that these regions are not well conserved (data not shown) (Burbach et al., Proc. Natl. Acad. Sci. USA 89: 8185–8189, 1992). This lack of conservation may indicate that the C-termini of these genes have divergent functions, or that the functions harbored in the C-termini can be accomplished by a variety of different sequences. For example, the C-termini of the AHR, ARNT, and SIM all harbor potent transactivation domains, yet display little sequence homology.

Figure 4:
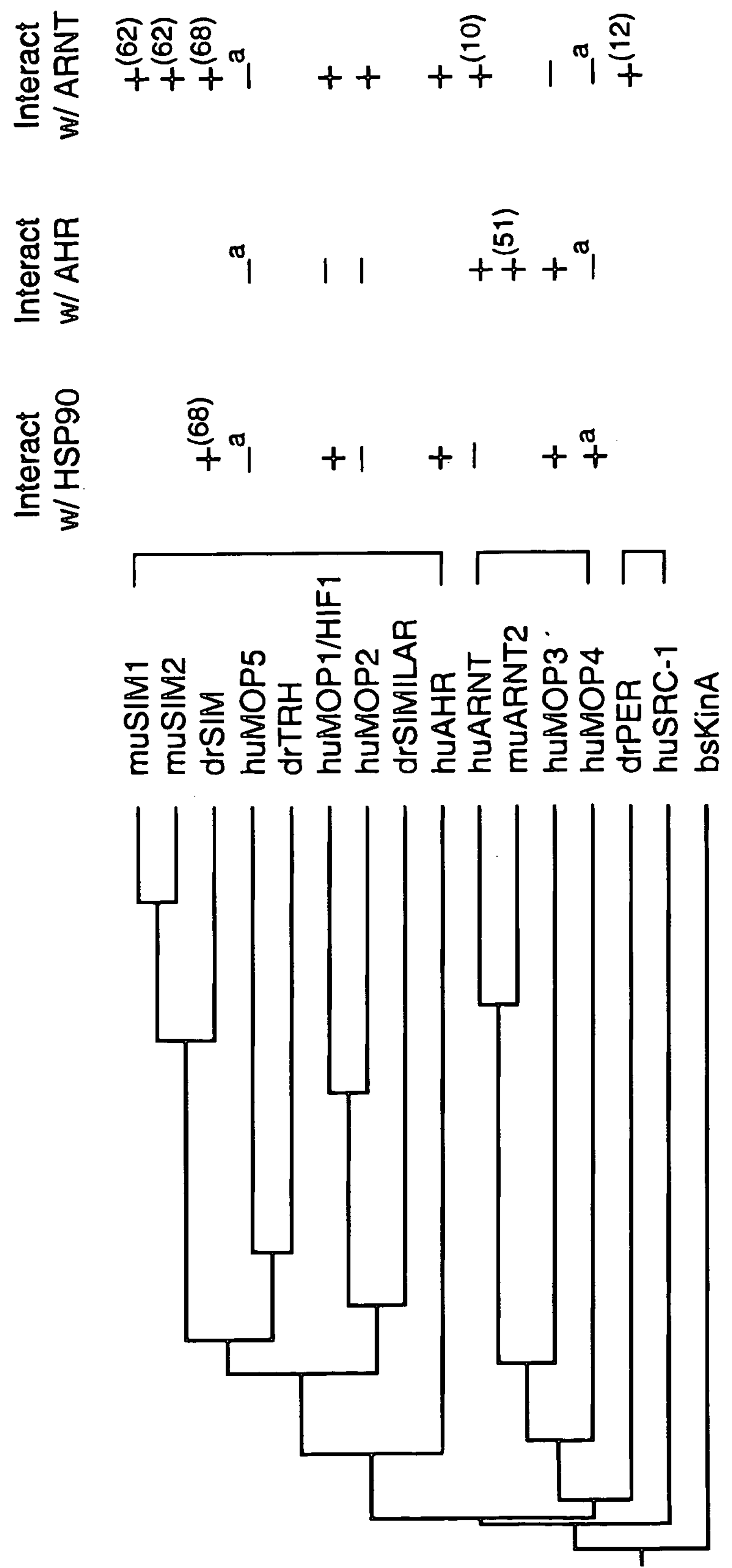
FIG. 4. Schematic comparison of homology of PAS family members. A dendrogram was prepared from the primary amino acid CLUSTAL alignment above using the MEGALIGN program. The CLUSTAL alignment was performed using the MEGALIGN program (DNASTAR, Madison, Wis.) with PAM250 weight table using the following parameters: Ktuple=1, Gap Penalty=3, Window=5. Amino acid boundaries for the residues encompassing the bHLH and PAS domains of the MOPs were defined based on previous observations. The amino acid boundaries are as follows: huMOP1/HIF1 (91–342), huMOP2 (90–342), huMOP3 (148–439), huMOP4 (87–350), huMOP5 (32–296), huAHR (117–385), huARNT (167–464), drSIM (82–356), drPer (232–496) bsKINA (27–248), huSRC-1 (115–365), muARNT2 (141–437, muSIM1 (83–331), muSIM2 (83–332), drSIMILAR (174–419), and drTRH (145–471). The scale at the bottom indicates number of amino acid residue substitutions. PAS family members that interact with HSP90, interact with the AHR, and interact with ARNT by the coimmunoprecipitation method are indicated by a +, whereas members that do not interact are indicated by a –. An α denotes a bHLH-PAS member whose cDNA is not complete. Note that these interactions occur in vitro and may or may not be physiologically relevant. Where appropriate, the reference is included in parentheses.

To characterize the evolutionary and functional relationships of these proteins, we performed a parsimony analysis to identify functionally related subsets. A dendrogram representing the primary amino acid relationship between the PAS domains of these proteins is illustrated in FIG. 4. This schematic suggests that major groups exist for eukaryotic PAS family members. The AHR, drSIMILAR, MOP1/HIF1α, MOP2, drTRACHEALESS, MOP5, and SIM exist in one group, ARNT, muARNT2, MOP3, and MOP4 in another and PER and huSRC-1 exist in their own groups. Interestingly, this pattern reflects what is known functionally about the existing PAS members. The AHR, SIM, MOP1/HIF1α and MOP2 have all been shown to heterodimerize with the ARNT molecule and bind DNA. Additionally, the AHR and SIM are known to interact with HSP90, a chaperonin protein necessary for the signaling of the AHR and a number of steroid receptor family members in response to ligand. Based on these groupings, MOP5 may also be an ARNT-interacting protein and a candidate for interacting with Hsp90 and being activated by small molecule ligands. The observation that ARNT has been shown to be capable of forming DNA binding homodimers and as heterodimers with a number of previously identified members of the bHLH-PAS family (at least in vitro), suggests that it plays a role in a number of biological processes. Based on their similarity with ARNT, MOP3 and MOP4 may be candidates for binding DNA as homodimers, or for interacting with multiple bHLH-PAS members, possibly from the AHR group.

In addition to the relevance of the above data to TCDD signaling, they also reveal additional factors important to cellular responses to hypoxic stress. HIF1α/MOP1 and MOP2 appear to share a common dimeric partner—ARNT, and are capable of regulating a common battery of genes. This notion is supported by three lines of evidence: (1) both MOP1 and MOP2 interact with ARNT as defined by coimmunoprecipitation or two-hybrid assay; (2) they have similar DNA half-site specificities when complexed with ARNT; and (3) they are both transcriptionally active from TACGTG enhancers in vivo. The observation that HIF1α/MOP1 and MOP2 have markedly different tissue distributions suggests that these two proteins may be regulating similar batteries of genes in response to different environmental stimuli. Alternatively, these proteins may be involved in restricting expression of certain groups of genes regulated by TACGTG-dependent enhancers. Finally, it is now known that MOP2 and MOP7 are subunits of a "HIF1-like" complex (i.e. a "HIF2α" and a "HIF3α, respectively) that regulates hypoxia responsive genes in distinct sets of tissues.

From the foregoing discussion, it can be seen that, while the MOPs share certain common features among themselves and with other new members of the bHLH-PAS superfamily, each of MOPs 2–9 is a distinctive and unique member of that family. cDNA and deduced amino acid sequences for each of MOPs 1–9 is set forth at the end of this specification. General features of each MOP are summarized below. In addition, MOPs 1–5 are described in great detail in Example 1, MOP3 is specifically described in Example 2 and MOP 7 is described in Example 3.

MOP1: The nucleotide and deduced amino acid sequences of a cDNA encoding MOP1 are set forth herein as SEQ ID NOS: 1 and 10, respectively. The cDNA includes a complete coding sequence for MOP1. As discussed above, MOP1 is known more commonly in the literature as HIF (Hypoxia-Inducible Factor)-1α (Wang et al., 1995, supra). The factor is induced by low oxygen. It interacts with HSP90 and with ARNT (AHR's binding partner). The ARNT-dimerized factor regulates expression of erythropoietin, among other genes.

MOP2: The nucleotide and deduced amino acid sequences of a cDNA encoding MOP2 are set forth herein as SEQ ID NOS: 2 and 11, respectively. The cDNA includes a complete coding sequence for MOP2. MOP2 appears to be related structurally and functionally to MOP1. Similar to MOP1, MOP2 interacts with ARNT, but not AHR, and drives transcription in its ARNT-dimerized form. Unlike MOP1, MOP2 does not appear to interact significantly with HSP90. MOP2 is induced by low oxygen and may be involved in hypoxia responses in different cells and tissues than is MOP1. MOP2 is sometimes referred to herein as HIF2α.

MOP3: The nucleotide and deduced amino acid sequences of a cDNA encoding MOP3 are set forth herein as SEQ ID NOS: 3 and 12, respectively. The cDNA includes a complete coding sequence for MOP3. MOP 3 and MOP 4 are related to each other as binding partners, analogous to ARNT and AHR, respectively. As described in greater detail in Example 2, in addition to being a specific partner for MOP4, MOP3 is a general dimerization partner for a subset of the bHLH/PAS superfamily of transcriptional regulators. MOP3 interacts with MOP4, CLOCK, HIF1α and HIF2α. The MOP3-MOP4 heterodimer binds a CACGTGA-containing DNA element. Moreover, MOP3-MOP4 and MOP3-CLOCK complexes bind this element in COS-1 cells and drive transcription from a linked luciferase reporter gene. A high-affinity DNA binding site has also been deduced for a MOP3-HIF1α complex (TACGTGA). MOP3-HIF1α and MOP3-HIF2α heterodimers bind this element, drive transcription, and respond to cellular hypoxia.

MOP3 also binds HSP90, and may be conditionally activated (like AHR) depending on whether it is bound to HSP90 (see Example 1) (of the MOP3/MOP4 dimerization pair, one appears to be conditionally activated, but as yet it is unclear which one). Evidence from *Drosophila* and rat suggest that MOP3 (cycle/bMAL1b) is regulated in a circadian manner.

MOP3 expression appears to be controlled by alternate 5' promoter regions. MOP3 mRNA expression overlaps in a number of tissues with each of its four potential partner molecules in vivo.

MOP4: The nucleotide and deduced amino acid sequences of a cDNA encoding MOP4 are set forth herein as SEQ ID NOS: 4 and 13, respectively. The cDNA includes an apparently complete coding sequence for MOP4. MOP4 appears to be a human ortholog of a recently identified murine gene called "Clock", for its involvement in circadian rhythms (King et al., Cell 89: 641–653). MOP4 also interacts with HSP90 and, as discussed above, is the dimerization partner of MOP3, and may be conditionally activated. MOP4 appears to be localized in the cytoplasm.

MOP5: The nucleotide and deduced amino acid sequences of a cDNA encoding MOP5 are set forth herein as SEQ ID NOS: 5 and 14, respectively. The cDNA includes a partial coding sequence for MOP5; however a complete coding sequence for MOP5 has become publicly available subsequent to the making of the present invention (GenBank Accession No. U77968, submitted Nov. 11, 1996, published Jan. 21, 1997 by Zhou et al., Proc. Natl. Acad. Sci. USA 94: 713–718).

MOP6: The nucleotide and deduced amino acid sequences of a cDNA encoding MOP6 (of human origin) are set forth herein as SEQ ID NOS: 6 and 15, respectively. The cDNA includes a complete coding sequence for MOP6. The nucleotide sequence of MOP6 is fairly unique. It is most similar in the 5' region to the bHLH-PAS member trachealess, which suggests that MOP6 may be a regulator (developmental or otherwise) of hypoxia. Functional data shows that MOP6 forms a partnership with ARNT and drives a hypoxia responsive element.

MOP7: The nucleotide and deduced amino acid sequences of a cDNA encoding MOP7 are set forth herein as SEQ ID NOS: 7 and 16, respectively. The cDNA includes a complete coding sequence for MOP7. In accordance with this invention, MOP7 has been characterized as a new hypoxia-inducible factor, and therefore is sometimes referred to herein as HIF3α. The expression profile of MOP7 is as follows: testis, thymus>[lung, brain, heart, liver, skeletal muscle]>[skin, stomach, small intestine, kidney]. This expression profile is distinct from any of MOP1, MOP2, MOP3, AHR and ARNT, suggesting a different functional role for MOP7. MOP7 is most closely related to MOP1/HIF1α and MOP2 (HIF2α), as described in greater detail in Example 3. Accordingly, MOP7 is likely to regulate the same genes as does HIF1α and HIF2α, as evidenced by its dimerization with the same partners (ARNT, MOP3) and recognition of the same core response element. This, combined with the unique tissue-specific expression of MOP7 suggests that it may have a functional role associated with response to low oxygen in the tissues in which it is expressed.

MOP8: The nucleotide and deduced amino acid sequences of a cDNA encoding MOP8 are set forth herein as SEQ ID NOS: 8 and 17, respectively. The cDNA includes a complete coding sequence for MOP8. Like MOP4 and MOP3, MOP8 may be involved in regulation of circadian rhythm. MOP8 shows sequence similarity to other genes involved in the circadian pathway (human PER, *Drosophila* PER, human RIGUI).

MOP9: The nucleotide and deduced amino acid sequence of a cDNA encoding MOP9 are set forth herein as SEQ ID NOS: 9 and 18, respectively. Two ESTs (GenBank AA577389, AA576971) corresponding to a novel bHLH-PAS protein homologous to MOP3/bMAL1 were identified by TBLASTN searches of the *Drosophila* homolog of MOP3. Upon characterization, these clones were revealed to be truncated, and one of which appeared to be a splice variant. The cDNA was cloned from human brain mRNA, and alternative 5' splicing was found probably reflecting multiple promoters. A BLASTX search of the MOP 9 sequence reveals that it displays extended homology to MOP3 (E-154). These data suggest that MOP9 also pairs with CLOCK and MOP4 and binds an E-box element with flanking region specificity.

Although specific MOP clones are described and exemplified herein, this invention is intended to encompass nucleic acid sequences and proteins from humans and other species that are sufficiently similar to be used interchangeably with the exemplified MOP nucleic acids and proteins for the purposes described below. It will be appreciated by those skilled in the art that MOP-encoding nucleic acids from diverse species, and particularly mammalian species, should possess a sufficient degree of homology with human MOPs so as to be interchangeably useful in various applications. The present invention, therefore, is drawn to MOP-encoding nucleic acids and encoded proteins from any species in which they are found, preferably to MOPs of mammalian origin, and most preferably to MOPs of human origin. Additionally, in the same manner that structural homologs of human MOPs are considered to be within the scope of this invention, functional homologs are also considered to be within the scope of this invention.

Allelic variants and natural mutants of SEQ ID NOS: 1–9 or 10–17 are likely to exist within the human genome and within the genomes of other species. Because such variants are expected to possess certain differences in nucleotide and amino acid sequence, this invention provides isolated MOP-encoding nucleic acid molecules having at least about 65% (and preferably over 75%) sequence homology in the coding region with the nucleotide sequences set forth as SEQ ID NOS: 1–9 (and, most preferably, specifically comprising the coding regions of any of SEQ ID NOS: 1–9). This invention also provides isolated MOPs having at least about 75% (preferably 85% or greater) sequence homology with the amino acid sequence of SEQ ID NOS: 10–18. Because of the natural sequence variation likely to exist among the MOPs and nucleic acids encoding them, one skilled in the art would expect to find up to about 25–35% nucleotide sequence variation, while still maintaining the unique properties of the MOPs of the present invention. Such an expectation is due in part to the degeneracy of the genetic code, as well as to the known evolutionary success of conservative amino acid sequence variations, which do not appreciably alter the nature of the protein. Accordingly, such variants are considered substantially the same as one another and are included within the scope of the present invention.

For purposes of this invention, the term "substantially the same" refers to nucleic acid or amino acid sequences having sequence variation that do not materially affect the nature of the protein. With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function of the protein. The terms "percent identity" and "percent similarity" are also used herein in comparisons among amino acid sequences. These terms are intended to be defined as they are in the UWGCG sequence analysis program (Devereaux et al., Nucl. Acids Res. 12: 387–397, 1984), available from the University of Wisconsin.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1998) (hereinafter "Ausubel et al.") are used.

III. Preparation of MOP Nucleic Acid Molecules, MOP Proteins and Anti-MOP Antibodies A. Nucleic Acid Molecules Nucleic acid molecules encoding the MOPs of the invention may be prepared by two general methods: (1) They may be synthesized from appropriate nucleotide triphosphates, or (2) they may be isolated from biological sources. Both methods utilize protocols well known in the art.

The availability of nucleotide sequence information, such as a full length cDNA having any of SEQ ID NOS: 1–9, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a several-kilobase double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire double-stranded molecule. A synthetic DNA molecule so constructed may then be cloned and amplified in an appropriate vector.

Nucleic acid sequences encoding MOPs may be isolated from appropriate biological sources using methods known in the art. In a preferred embodiment, cDNA clones are isolated from libraries of human origin. In an alternative embodiment, genomic clones encoding MOPs may be isolated. Alternatively, cDNA or genomic clones encoding MOPs from other species, preferably mammalian species, may be obtained.

In accordance with the present invention, nucleic acids having the appropriate level sequence homology with the coding regions of any of Sequence I.D. Nos. 1–9 may be identified by using hybridization and washing conditions of appropriate stringency. For example, hybridizations may be performed, according to the method of Sambrook et al., using a hybridization solution comprising: 5×SSC, 5× Denhardt's reagent, 1.0% SDS, 100 μg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° in 1×SSC and 1% SDS, changing the solution every 30 minutes.

One common formula for calculating the stringency conditions required to achieve hybridization between nucleic acid molecules of a specified sequence homology (Sambrook et al., 1989):

$$T_m = 81.5° \text{ C.} + 16.6 \text{Log } [\text{Na+}] + 0.41(\% \text{ G+C}) - 0.63 (\% \text{ formamide}) - 600/\#\text{bp in duplex}$$

As an illustration of the above formula, using [N+]=[0.368] and 50% formamide, with GC content of 42% and an average probe size of 200 bases, the $T_m$ is 57° C. The $T_m$, of a DNA duplex decreases by 1–1.5° C. with every 1% decrease in homology. Thus, targets with greater than about 75% sequence identity would be observed using a hybridization temperature of 42° C.

Nucleic acids of the present invention may be maintained as DNA in any convenient cloning vector. In a preferred embodiment, clones are maintained in plasmid cloning/expression vector, such as pGEM-T (Promega Biotech, Madison, Wis.) or pBluescript (Stratagene, La Jolla, Calif.), either of which is propagated in a suitable *E. coli* host cell.

MOP nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having any of SEQ ID NOS: 1–9. Such oligonucleotides are useful as probes for detecting MOP genes or mRNA in test samples of cells, tissue or other biological sources, e.g. by PCR amplification, or for the positive or negative regulation of expression of MOP genes at or before translation of the mRNA into proteins.

B. Proteins

MOP proteins of the present invention may be prepared in a variety of ways, according to known methods. The proteins may be purified from appropriate sources, e.g., cultured or intact cells or tissues.

Alternatively, the availability of nucleic acids molecules encoding MOPs enables production of the MOP proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

According to a preferred embodiment, larger quantities of MOP proteins may be produced by expression in a suitable procaryotic or eucaryotic system. For example, part or all of a DNA molecule, such as any of the cDNAs having SEQ ID NOS: 1–9, may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The MOPs produced by gene expression in a recombinant procaryotic or eucyarotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners. The MOP proteins of the invention, prepared by the aforementioned methods, may be analyzed according to standard procedures.

The present invention also provides antibodies capable of immunospecifically binding to MOP proteins of the invention. Polyclonal or monoclonal antibodies directed toward any of MOPs 1–9 may be prepared according to standard methods. Monoclonal antibodies may be prepared according to general methods of Köhler and Milstein, following standard protocols. In a preferred embodiment, antibodies have been prepared, which react immunospecifically with various epitopes of the MOPs.

Polyclonal or monoclonal antibodies that immunospecifically interact with MOPs can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-MOP antibodies are described below.

IV. Uses of MOP-Encoding Nucleic Acids, MOP Proteins and Anti-MOP Antibodies

A. MOP-Encoding Nucleic Acids

MOP-encoding nucleic acids may be used for a variety of purposes in accordance with the present invention. MOP-encoding DNA, RNA, or fragments thereof may be used as probes to detect the presence of and/or expression of genes encoding MOPs. Methods in which MOP-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR). In addition, recombinant cellular assay systems to examine signal transduction pathways in which the MOPs are involved are described below.

The MOP-encoding nucleic acids of the invention may also be utilized as probes to identify related genes either from humans or from other species. As is well known in the art, hybridization stringencies may be adjusted to allow hybridization of nucleic acid probes with complementary sequences of varying degrees of homology. Thus, MOP-encoding nucleic acids may be used to advantage to identify and characterize other genes of varying degrees of relation to the respective MOPs, thereby enabling further characterization the AHR or related signaling cascades. Additionally, they may be used to identify genes encoding proteins that interact with MOPs (e.g., by the "interaction trap" technique, or modifications thereof, as described in Example 1), which should further accelerate elucidation of these cellular signaling mechanisms.

Nucleic acid molecules, or fragments thereof, encoding MOPs may also be utilized to control the production of the various MOPs, thereby regulating the amount of protein available to participate in cellular signaling pathways. In one embodiment, the nucleic acid molecules of the invention may be used to decrease expression of certain MOPs in cells. In this embodiment, full-length antisense molecules are employed which are targeted to respective MOP genes or RNAs, or antisense oligonucleotides, targeted to specific regions of MOP-encoding genes that are critical for gene expression, are used. The use of antisense molecules to decrease expression levels of a pre-determined gene is known in the art. In a preferred embodiment, antisense oligonucleotides are modified in various ways to increase their stability and membrane permeability, so as to maximize their effective delivery to target cells in vitro and in vivo. Such modifications include the preparation of phosphorothioate or methylphosphonate derivatives, among many others, according to procedures known in the art.

In another embodiment, the transcription regulation activity of bHLH-PAS homodimers or heterodimers involving MOPs may be blocked by genetically engineering a target cell to express a defective MOP—specifically one that has been modified to be unable to bind DNA. When the defective MOP dimerizes, the dimer is also unable to bind DNA, and therefore is unable to carry out its transcriptional regulatory function.

In another embodiment, overexpression of various MOPs is induced, which can lead to overproduction of a selected MOP. Overproduction of MOPs may facilitate the isolation and characterization of other components involved in protein—protein complex formation occurring during the MOP-related signal transduction in cells.

As described above, MOP-encoding nucleic acids are also used to advantage to produce large quantities of substantially pure MOP proteins, or selected portions thereof.

B. MOP Proteins and Anti-MOP Antibodies

Purified MOPs, or fragments thereof, may be used to produce polyclonal or monoclonal antibodies which also may serve as sensitive detection reagents for the presence and accumulation of MOPs (or complexes containing the MOPS) in cultured cells or tissues or in intact organisms. Recombinant techniques enable expression of fusion proteins containing part or all of a selected MOP protein. The full length protein or fragments of the protein may be used to advantage to generate an array of monoclonal or polyclonal antibodies specific for various epitopes of the protein, thereby providing even greater sensitivity for detection of the protein in cells or tissue.

Polyclonal or monoclonal antibodies immunologically specific for a MOP may be used in a variety of assays designed to detect and quantitate the protein. Such assays include, but are not limited to: (1) flow cytometric analysis; (2) immunochemical localization of a MOP in cells or tissues; and (3) immunoblot analysis (e.g., dot blot, Western blot) of extracts from various cells and tissues. Additionally, as described above, anti-MOPs can be used for purification of MOPs (e.g., affinity column purification, immunoprecipitation).

C. Recombinant Cells and Assay Systems

Genetically engineered cells, such as yeast cells or mammalian cells, may be produced to express any one, or a combination, of MOPs described herein. Such cells can be used to evaluate the binding interactions between MOPs, or between a MOP and another member of the bHLH-PAS superfamily (e.g., AHR, ARNT), and the requirement for homodimerization or heterodimerization of the MOPs for initiation of transcriptional control of a reporter gene driven by appropriate enhancer elements. In addition, such recombinant cells can be used to study the effect of external stimuli, such as hypoxia or TCDD, on activation of a selected MOP, or they can be used to screen panels of drugs for control of MOP-involved signal transduction pathways. U.S. Pat. No. 5,650,283 to Bradfield et al., the disclosure of which is incorporated herein by reference, describes recombinant cellular systems and assays for detecting agonists to the AHR. These materials and methods may be used similarly to design recombinant systems for evaluating any of MOP1-MOP8, in the presence or absence of an external stimulant.

Appropriate yeast cells for production of such recombinant systems include *Saccharomyces cerevisiae* and *Saccharomyces* pombe. Yeast strains carrying endogenous functional HSPs may be utilized (e.g., A303 obtained from Rick Gaber, Northwestern University, or commercially available equivalents). Yeast strains in which the genes encoding HSPs have been disrupted may also be utilized (e.g., GRS4, obtained from Susan Lindquist, University of Chicago), affording an opportunity to examine the relationship of various MOPs to HSPs.

Appropriate mammalian cells for production of such recombinant systems include COS, Hep3b, HepGr and Hepalclc7 cells, among others.

In one type of assay where the MOP signal transduction pathway is affected by an external stimulus (i.e. an agonist such as TCDD in the AHR-ARNT system, or cobalt chloride in the MOP1/HIF1α-ARNT system), an appropriate cell can be transformed with an expression plasmid expressing a full length agonist receptor MOP, along with its dimerization partner (if the MOP forms heterodimers) and a reporter plasmid expressing a reporter gene, such as LacZ or luciferin, which is driven by an appropriate enhancer element. The presence or potency of a selected agonist may be determined by its ability to activate transcription of the reporter gene in the recombinant system.

In another embodiment, a recombinant system that does not rely on heterodimerization can be constructed. In this case, a cell is transformed with an expression plasmid expressing a chimeric agonist-sensitive MOP, along with a reporter plasmid expressing a reporter gene driven by a suitable promoter. The chimeric MOP is modified to replace the heterodimerization domains (i.e. the bHLH-PAS domain) with a DNA binding domain, such as LexA or Gal4. Such chimeras will homodimerize and activate transcription of genes positioned downstream of LexA or Gal4 binding sites engineered into the reporter plasmid.

In a preferred embodiment, described in detail in Example 1, a modified yeast "two hybrid" system is used to assess binding interactions between MOPs (and other bHLH-PAS proteins) and the subsequent initiation of transcriptional control. For instance, as described in Example 1, fusion proteins were constructed in which the DNA binding domain of the bacterial repressor, LexA, was fused to the bHLH-PAS domains of the MOP proteins. Interactions were tested by cotransformation of each LexAMOP construct with either the full length AHR or ARNT into the L40 yeast strain, which harbors an integrated lacZ reporter gene driven by multiple LexA operator sites. In this system, LexAMOP fusions which interact with AHR or ARNT drive expression of the lacZ reporter gene. The effect of various agonists on reporter gene expression can also be evaluated using this system.

Any one or more of the aforementioned recombinant cell systems and assays can be used to screen panels of drugs for their effect on specific signal transduction pathways. For instance, recombinant systems employing any or MOPs 1, 2, 6 or 7 may be used to screen for drugs that stimulate red blood cell synthesis, angiogenesis or glucose metabolism.

Recombinant systems employing any of MOPs 3, 4, 8 or 9 may be used to screen for drugs that modify circadian rhythms. In connection with this embodiment, as described in greater detail in Example 2, we have determined the binding sequence for the MOP3/MOP4 heterodimer, and have constructed the following recombinant plasmids: PL833, a MOP3 expression vector for mammalian cells; PL834, a MOP4 expression vector for mammalian cells; and PL880, a reporter plasmid (expressing luciferase) driven by the MOP3/MOP4 consensus enhancer sequence GCA-_CACGTG_ACC (SEQ ID NO: 124). When the three plasmids are introduced into a mammalian cell, the reporter gene responds to the presence of the MOP3/MOP4 dimer. This system is used in a high throughput microwell assay to screen for compounds that are specific activators or inhibitors of these transcription factors. A similar system has been established for MOP7 (HIF3α), as set forth in Example 3.

The following examples are intended to illustrate embodiments of the invention. They are not intended to limit the scope of the invention in any way.

EXAMPLE 1

Identification and Characterization of MOPs 1–5 cDNAs and Encoded Proteins

We employed an iterative search of human expressed sequence tags to identify novel basic-helix-loop-helix-PAS (bHLH-PAS) proteins that might interact with either the Ah receptor (AHR) or the Ah receptor nuclear translocator (ARNT). In this example, we describe the identification and characterization of five new "Members of the PAS superfamily," or MOPs 1–5, that are similar in size and structural organization to the AHR and ARNT.

Methods

Search Strategy. The bHLH-PAS domains of the huAHR, huARNT, drSIM, and the PAS domain of drPER were used as query sequences in BLASTN searches of the GenBank database between December of 1994 and October of 1995, using the following default values: Database=NR, expect=10, word length=12 (Altschul et al., J. Mol. Biol. 215: 403–410, 1990). Preliminary experiments comparing AHR and PER led us to define candidate ESTs as those "hits" that yielded scores of 150 or higher. As a method to confirm the similarity of these EST sequences to known bHLH-PAS proteins, each candidate EST was subsequently compared to the NR subset of GenBank using the BLASTX program, matrix=blosum 62, word length=3. Only ESTs that retrieved known bHLH-PAS proteins by this method of confirmation were further characterized.

Oligonucleotide Sequences: Sequences of oligonucleotides are given below. In cases where the oligonucleotide was used in gel shift assays, the 6 bp target sequence is underlined.

OL21 5' CGAGGTCGACGGTATCG 3' (SEQ ID NO:19)

OL22 5' TCTAGAACTAGTGGATC 3' (SEQ ID NO:20)

OL124 5' CCCAAGCTTACGCGTGGTCTTTGAAGTCAACCTCACC 3' (SEQ ID NO:21)

OL145 5' AGCTCGAAATTAACCCTCACTAAAGG 3' (SEQ ID NO:22)

OL176 5' CGGGATCCTTACACATTGGTGTTGGTACAGATGATGTACTC 3' (SEQ ID NO:23)

OL180 5' GCGTCGACTGATGAGCAGCGGCGCCAACATCACC 3' (SEQ ID NO:24)

OL201 5' GATAAGAATGCGGCCGCAGATCTGGGTCCGAAGCACACG 3' (SEQ ID NO:25)

OL202 5' CATTACTTATCTAGAGCTCG 3' (SEQ ID NO:26)

OL226 5' CGGGATCCTCATGGCGGCGACTACTGCCAACC 3' (SEQ ID NO:27)

OL365 5' GACAGTTGCTTGAGTTTCAACC 3' (SEQ ID NO:28)

OL386 5' TTATGAGCTTGCTCATCAGTTGCC 3' (SEQ ID NO:29)

OL387 5' CCTCACACGCAAATAGCTGATGG 3' (SEQ ID NO:30)

OL392 5' CCGCTCGAGTGATGAGCAGCGGCGCCAACATCACC 3' (SEQ ID NO:31)

OL393 5' CCGCTCGAGTGGCAGCTACAGGAATCCACC 3' (SEQ ID NO:32)

OL404 5' GCGGTACCGGGACCGATTCACCATGGAG 3' (SEQ ID NO:33)

OL414 5' TCGAGCTGGGCAGG GTACGTGGCAAGGC 3' (SEQ ID NO:34)

OL415 5' TCGAGCCTTGCCACGTACCCTGCCCAGC 3' (SEQ ID NO:35)

OL418 5' GTAAAACGACGGCCAGT 3' (SEQ ID NO:36)

OL419 5' GGAAACAGCTATGACCATG 3' (SEQ ID NO:37)

OL443 5' TCGAGCTGGGCAGG GTGCGTGGCAAGGC 3' (SEQ ID NO:38)

OL444 5' TCGAGCCTTGCCACGCACCCTGCCCAGC 3' (SEQ ID NO:39)

OL445 5' TCGAGCTGGGCAGGT CACGTGGCAAGGC 3' (SEQ ID NO:40)

OL446 5' TCGAGCCTTGCCACGTGACCTGCCCAGC 3' (SEQ ID NO:41)

OL447 5' TCGAGCTGGGCAGG TTGCGTGGCAAGGC 3' (SEQ ID NO:42)

OL448 5' TCGAGCCTTGCCACGCAACCTGCCCAGC 3' (SEQ ID NO:43)

OL450 5' TACTGGCCACTTACTACCTGACC 3' (SEQ ID NO:44)

OL456 5' AACCAGAGCCATTTTTGAGACT 3' (SEQ ID NO:45)

OL477 5' GCTCTAGAGGCCACAGCGACAATGACAGC 3' (SEQ ID NO:46)

OL479 5' GATCGGAGGTGTTCTATGAGC 3' (SEQ ID NO:47)

OL489 5' TTAGGATGCAGGTAGTCAAACA 3' (SEQ ID NO:48)

OL496 5' GTTCTCCATGGACCAGACTGA 3' (SEQ ID NO:49)

OL499 5' CGGGTACCCTGGGCCCTACGTGCTGTCTC 3' (SEQ ID NO:50)

OL500 5' CGGCTAGCCTCTGGCCTCCCTCTCCTTGATGA 3' (SEQ ID NO:51)

OL514 5' CTGGGAGCCTGCCTGCCTTCA 3' (SEQ ID NO:52)

OL520 5' CCCAAGGAGAGGCGTGAT 3' (SEQ ID NO:53)

OL540 5' GGGATCCTCGTCGCCACTG 3' (SEQ ID NO:54)

OL541 5' ATGCAGTACCCAGACGGATTTC 3' (SEQ ID NO:55)

OL560 5' TGCACGGTCACCAACAGAG 3' (SEQ ID NO:56)

OL561 5' TTGCCAGTCGCATGATGGA 3' (SEQ ID NO:57)

OL565 5' CTGAACAGCCATCCTTAG 3' (SEQ ID NO:58)

OL568 5' AGCTTGCCCTACGTGCTGTCTCAG 3' (SEQ ID NO:59)

OL569 5' AATTCTGAGACAGCACGTAGGGCA 3' (SEQ ID NO:60)

OL590 5' AGAGGTGCTGCCCAGGTAGAA 3' (SEQ ID NO:61)

OL611 5' CAATGATGAGGGAAACACTG 3' (SEQ ID NO:62)

OL657 5' CGGGATCCCGTCAACTGGAGATGAGCAAGGAG 3' (SEQ ID NO:63)

OL665 5' CTGCAAAAATCCGATGACCTCTT 3' (SEQ ID NO:64)

OL681 5' CGGGCAGCAGCGTCTTC 3' (SEQ ID NO:65)

OL682 5' GCGTCCGCAGCCCCAGTTG 3' (SEQ ID NO:66)

OL683 5' TTCAATGTTCTCATCAAAGAGC 3' (SEQ ID NO:67)

OL684 5' GAACAGTTTTATAGATGAATTGGC 3' (SEQ ID NO:68)

OL689 5' GAGGTGTTTCAATTCATCGTCT 3' (SEQ ID NO:69)

OL715 5' GGGATCCGTGACCGATTCACCATGGAG 3' (SEQ ID NO:70)

OL716 5' CTGCAGGTCACACAACGTAATTCACACA 3' (SEQ ID NO:71)

OL717 5' GGGATCCGTATGACAGCTGACAAGGAG 3' (SEQ ID NO:72)

OL718 5' GGTCGACGTCACAGGACGTAGTTGACACA 3' (SEQ ID NO:73)

OL719 5' GAATCCATGAGCAAGGAGGCCGTG 3' (SEQ D NO:74)

OL720 5' GGTCGACGTCAAACAACAGTGTTAGTTGA 3' (SEQ BD NO:75)

OL721 5' GGGATGCGTATGGATGAAGATGAGAAAGAC 3' (SEQ ID NO:76)

OL722 5' GGTCGACGCTAGACCGAGTGTGTGCA 3' (SEQ ID NO:77)

Cloning strategy. To obtain extended open reading frames for each EST, an anchored-PCR strategy was employed to amplify additional flanking sequence from a variety of commercial cDNA libraries that were constructed in the phagemid Lambda Zap (Tissues; HepG2, Fetal Brain and Skeletal Muscle; Stratagene, La Jolla, Calif.) (Table 1) (Innis et al. (eds), *PCR Protocols: a Guide to Methods and*

*Applications*, Academic Press, San Francisco, 1990). The resulting PCR products were subjected to agarose gel electrophoresis, transferred to a nylon membrane and analyzed by hybridization with a $^{32}$P-labeled probe generated from the corresponding parent EST plasmid (Table 1). After autoradiography, the positive PCR products were purified by gel electrophoresis and cloned using the pGEM-T vector system (Promega, Madison, Wis.). Dideoxy sequencing was performed to characterize each positive clone.

TABLE 1

MOP cDNA Clone Information

Row 1: clones (in parentheses) containing the candidate ESTs were requested from their laboratory of origin.

Row 2: the Genbank accession number for each original EST is indicated.

Row 3: oligonucleotides used in library screening. Sequence information generated from this original clone was used to design oligonucleotides for use in an anchored PCR strategy, whereby gene-specific and vector-specific primers were used to amplify 5' and 3 portions of the cDNA. Vector specific primers corresponded to modified T3 (5', OL145) or T7 (3', OL146) primers. A matrix of gene-specific primers against annealing temperature (50–65° C.) was attempted for each clone, generally leading to at least one successful reaction.

Row 4: the cDNA libraries from which additional sequence of positive clones was identified.

Row 5: size of ORFs. We define a complete ORF by the presence of an in-frame stop codon 5' to a methionine codon that lies within a Kozak consensus sequence for translational initiation. The 3' end of open reading frames are defined by the presence of an in-frame termination codon. An asterisk (*) denotes a clone which does not meet these criteria (see text).

Row 6: Genbank accession numbers of the final MOP cDNAs are given.

| | MOP1/HIF1α | MOP2 | MOP3 | MOP4 | MOP5 |
|---|---|---|---|---|---|
| Laboratory of origin (clone desig.) | Bell (hbc025) | IMAGE (67043) | IMAGE (23820, 50519) | Liew (F9047, PL420) | IMAGE (42596) |
| EST Genbank accession number | T10821 | T70415 | T77200, H17840 | R58054 | R67292 |
| Gene-specific oligo used in PCR | OL365 (5') | OL456 (5') OL496 (3') OL514 (3') OL541 (3') | OL489 (5') | OL520 (5') | OL540 (5') |
| Library screened | HepG2 | HepG2 | Fetal brain | HeLa | HepG2 |
| ORF size (a.a.'s) | 826 | 870 | 624 | 642* | 412* |
| Final cDNA Genbank accession number | U29165 | U51626 | U51627 | U51625 | U51628 |

Plasmid Construction for Expression in Vivo. Sequence information from each EST was used to design PCR primers for the amplification of cDNA from commercially available libraries. Expression plasmids were constructed by standard protocols (Sambrook et al., 1989). For a summary of clone designations, PCR primers, DNA templates and GenBank accession numbers, refer to Table 1. A brief description follows.

MOP1 expression vectors. Oligonucleotides OL404 and OL365 were used as primers in a PCR to amplify a 970 bp fragment from a HepG2 cell cDNA library. This fragment was cloned into the pGEM-T vector in the T7 orientation and designated PL439. To generate pGMOP1, the SalIXhoI fragment of hbc025 was subcloned into SalI digested PL439. To increase transcription efficiency of the MOP1 cDNA, pGMOP1 was digested with KpnI and SacI and this fragment subcloned into the corresponding sites of psputk generating PL415 (Stratagene, La Jolla, Calif.) (Falcone & Andrews, Mol. Cell. Biol. 11: 2656–2664, 1991). The complete ORF of the MOP1 cDNA was amplified using the PCR and oligonucleotides OL425 and OL536. This fragment was digested with BamHI and ligated into the BamHI site in the psport polylinker (Life Technologies, Inc.). This plasmid was designated PL611.

MOP2 expression vectors. PCR was employed using OL477 and OL450 to amplify a 931 bp MOP2 fragment from a HepG2 cDNA library. This fragment was cloned into pGEM-T in the SP6 orientation and designated PL424. Using OL560 and OL590, PCR amplification from this same library yielded a 3' fragment of the MOP2 cDNA. This fragment was cloned into pGEM-T in the SP6 orientation and was designated PL445. PL424 was digested SalI and EcoRI and the fragment ligated into a SalI/EcoRI digested PL445 to generate a full ORF MOP2 expression vector designated PL447. The complete ORF of the MOP2 cDNA was cloned into psport as follows; PL447 was digested with SacII, treated with the Klenow fragment of DNA Polymerase I in the presence of dNTPs, and subsequently digested with SalI. This fragment was purified and ligated into pSport digested with HindIII, repaired with Klenow, then digested with SalI. This construct was designated PL477.

MOP3 expression vectors. Using the primers OL145 and OL489 and a human fetal brain cDNA library as template, the PCR was used to obtain a 1380 bp fragment. This fragment was isolated and cloned into pGEM-T as above, and this plasmid designated PL487. A fragment of MOP3 was obtained by the PCR using Pfu polymerase (Stratagene), primers OL657 and OL689 and PL487 as template. To obtain a full length MOP3 cDNA fragment, the megaprimer fragment obtained above was used in the PCR against oligonucleotide OL611 using IMAGE clone 50519 as a template (Sarkar & Somers, Biotechniques 8: 404–407, 1990). This product was cloned into pGEM-T in the SP6 orientation as above and designated PL425.

MOP4 expression vectors. Using primers OL520 and OL145 and a HepG2 cDNA library as template, the PCR was performed to isolate a 5' fragment of the MOP4 cDNA. This fragment was cloned in the T7 orientation of pGEM-T and designated PL448. The cDNA insert of the phage clone F9047 (C. C. Liew, Toronto, Calif.) was amplified by the PCR using oligonucleotides OL418 and OL419 and subcloned into the pGEM-T vector (Hwang et al., J. Mol. Cell. Cardiol. 26: 1329–1333, 1994). This clone was designated PL420. An EcoRI fragment of PL448 was isolated and cloned into a partially EcoRI digested PL420. This clone was subjected to the PCR with oligonucleotides OL698 and OL146, and the fragment cloned into the pGEM-T vector, and designated PL545.

MOP5 expression vectors. The PCR was used to obtain a 1260-bp fragment of the MOP5 gene using oligonucleotides OL685 and OL686 and IMAGE clone 42596 as template. This fragment was purified and subcloned into the pGEM-T vector as above in the SP6 orientation. This plasmid was designated PL528 and subsequently digested with SalI and partially digested with NcoI. This fragment was ligated into Nco I/SalI-cut psputk, and the resulting vector designated PL554.

Hypoxia responsive luciferase reporters. The plasmid pGL2EPOEN was constructed as follows: The hypoxia responsive enhancer from the 3' region of the EPO gene was amplified by PCR using oligonucleotides OL499 and OL500 and human genomic DNA as template (amplified fragment corresponds to nucleotides 127 to 321 as reported in the EPO structural gene sequence found in GenBank Accession GBL16588). This fragment was digested with KpnI and NheI and cloned into the corresponding sites of the plasmid pGL2-Promoter (Promega).

Antibody Production. Antisera against MOP1, MOP2, AHR and ARNT were prepared in rabbits using immunization protocols that have been described previously (Poland et al., Mol. Pharmacol. 39: 20–26, 1991; Pollenz et al., Mol. Pharmacol. 45: 428–438, 1994). Crude antisera was chosen for use in all coimmunoprecipitation experiments and the PI sera from the same rabbit served to preclear the samples. For MOP1, the plasmid hbcO25 was digested with EcoRI and the 604 bp fragment was treated with the Klenow fragment of DNA polymerase-1 in the presence of dNTPs and cloned into the SmaI site of the histidine tag fusion vector pQE-32 (Qiagen, Chatsworth, Calif.). This clone, designated PL377, was transformed by electroporation into M15(REP4) cells for expression under IPTG induction. The expressed protein was purified from 8 M urea using Ni-NTA agarose, extensively dialyzed against 25 mM MOPS, pH 7.4, 100 mM KCl, and 10% glycerol before its use as an immunogen. For AHR, the human cDNA clone PL71 (Dolwick et al., Mol. Pharmacol. 44: 911–917, 1993) was digested with BamHI and cloned into the corresponding site of the histidine fusion vector pQE31 (Qiagen). The AHR protein fragment was expressed and purified exactly as described for MOP1 (above). Antiserum produced against this protein was designated R2891. For MOP2 a SacI/PstI fragment of PL445 was cloned into SacI/PstI cut pQE-31 to generate PL456. This clone, designated PL456, was transformed into M15 (REP4) cells and the protein expressed under IPTG induction. The histidine tagged fusion protein was first extracted in guanidine hydrochloride, dialyzed extensively and purified on Ni-NTA agarose as above. Antiserum produced against this protein was designated R4064. ARNT-specific antisera was raised against huARNT protein purified from baculovirus as previously described (Chan et al., J. Biol. Chem. 269: 26464–26471, 1994).

Northern Protocol. Multiple tissue northern blots containing 2 μg of poly(A)+ mRNA prepared from human heart, brain, placenta, lung, liver, skeletal muscle, kidney, and pancreas were probed with random primed cDNA fragments using an aqueous hybridization protocol (Clontech, Palo Alto, Calif.). Hybridization solution contained 5×SSPE (0.75 M NaCl, 50 mM $NaH_2PO_4$, 5 mM $Na_2EDTA$, pH 7.4) 2× Denhardt's solution (0.04% w/v Ficoll 400, 0.04% w/v polyvinylpyrrolidone, 0.04% w/v Bovine Serum Albumin), 0.5% SDS, and 100 ug/mL heat denatured salmon sperm DNA. A blot was prehybridized for 3–6 hours at 65° C., the hybridization solution was changed and $1–5\times10^6$ cpm/mL of a random primed cDNA fragment was added. Samples were hybridized overnight at 65° C., washed twice with 2×SSC (0.3 M NaCl, 30 mM $Na_2$Citrate, pH 7.0), 0.5% SDS at room temperature, once with 1×SSC, 0.1% SDS at the hybridization temperature, and once with 0.1×SSC, 0.1% SDS at the hybridization temperature.

Yeast Two-Hybrid Analysis. A modified yeast interaction trap was employed to identify those MOPs that could interact with the AHR or ARNT. LexAMOP chimeras were constructed to fuse the bHLH-PAS domains of the MOP proteins with the DNA binding domain of the bacterial protein LexA (amino acids 1–202) (Bartel et al., BioTechniques 14: 920–924, 1993). To amplify the region corresponding to the bHLH-PAS domains of MOP1, OL715 and OL716 were employed in the PCR using PL415 as template. To amplify the region corresponding to the bHLH-PAS domains of MOP2, OL717 and OL718 were employed in the PCR using PL447 as template. To amplify the region corresponding to the bHLH-PAS domains of MOP3, OL719 and OL720 were employed in the PCR using PL486 as template. To amplify the region corresponding to the bHLH-PAS domains of MOP4, OL721 and OL722 were employed in the PCR using PL545. Since a more detailed domain map existed for the AHR, a construct was made with a fine deletion of the transactivation domain. The N-terminal portion of the AHR was amplified by the PCR using oligonucleotides OL180 and OL124 and pmuAHR as template (Dolwick et al., Proc. Natl. Acad. Sci. USA 90: 8566–8570, 1993). This product was digested with KpnI and SalI, and cloned into the corresponding sites of pSG424 (Sadowski & Ptashne, Nucl. Acids Res. 17: 7539, 1989). This clone was designated PL187. The 3' end of the AHR cDNA was amplified by PCR using oligonucleotides OL201 and OL202 and pmuAHR as template. This product was digested with NotI, and cloned into the corresponding site of pSGAhN-delta-166 (Dolwick et al, Proc. Natl. Acad. Sci. USA 90: 8566–8570, 1993). This clone was designated PL188. PL188 was digested with KpnI and XbaI, and this fragment cloned into the corresponding sites of PL187. This clone was designated PL204. A cDNA fragment of the AHR was amplified by the PCR using OL392 and OL393 and PL204 as template. This product was cloned using the pGEM-T system, and designated pGTAHR-delta-TAD. This construct was digested with XhoI and this fragment ligated into SalI cut pBTM116 (Vojtek et al., Cell 74: 205–214, 1993). This construct was designated pBTMAHR. LexAARNT was constructed by PCR using oligonucleotides OL226 and OL176 and PL87 as template. The PCR product was cloned into pGEM-T as above, and the BamHI fragment cloned into a BamHI digested pGBT9 vector (Clontech). This construct was cut with BamHI and subcloned into a BamHI digested pBTM116. This construct was designated LexAARNT. Following amplification these products were purified and cloned into the pGEM-T vector. These clones were designated PL537 (MOP1), PL538 (MOP2), PL539 (MO3), and PL540 (MOP4). These plasmids were digested with BamHI/PstI (PL537), BamHI/SalI (PL538 and PL540), and EcoRI/SalI (PL539), and these fragments ligated into the appropriately digested pBTM116. These clones were designated LexAMOP1, LexAMOP2, LexAMOP3, and LexAMOP4, respectively. Full length expression plasmids harboring the AHR and ARNT were constructed as follows: PL104 (psporthuAHR) was cut with SmaI, the insert purified and subcloned into SmaI site of pCW10, and this plasmid was designated PL317. This clone was digested with SmaI and subcloned into a SmaI cut pRS305, and this clone designated PRSAHR. The ARNT cDNA (PL101) was digested with Not I and XhoI, and cloned into the corresponding sites of pSGBMX1. This plasmid was designated PL371, and subsequently was digested with NotI and XhoI, this fragment cloned into the corresponding sites of pSGBCU11. This clone was designated PL574. The LexAMOP fusion protein constructs were cotransformed with a yeast expression vector containing the full length AHR or ARNT into L40, a yeast strain containing integrated lacZ and HIS3 reporter genes. As controls, LexAAHR and LexAARNT were cotransformed with AHR and ARNT. The strength of interaction was visually characterized by X-Gal (5-bromo-4-chloro-3-indolyl-(-D-galactoside) plate assays, performed after three days growth on selective media (Bohen et al, Proc. Natl. Acad. Sci. USA 90: 11424–11428, 1993). To provide quantitation of the interaction strength, multiple colonies from yeast harboring each bHLH-PAS combination colonies were grown overnight in liquid media. Liquid cultures were grown for 5 hours, and assayed for lacZ activity using the Galacto-Light chemiluminescence reporter system (Tropix, Bedford, Mass.). To determine the effect of AHR agonists on these interactions, yeast were also grown on plates or in liquid culture with and without 1 μM βNF (Carver et al., J. Biol. Chem. 269: 30109–30112, 1994).

To ensure expression of each bHLH-PAS construct, western blot analysis was performed using antibodies raised against the LexA DNA binding domain. Yeast extracts were prepared from 15 mL overnight cultures derived from multiple colonies of yeast expressing each LexAMOP fusion protein. Cultures were subjected to centrifugation at 1200×g for 5 minutes and the pellet was resuspended in 500 μL of 6 M Guanidinium-HCl, 0.1 M Na-Phosphate Buffer, 0.01 M Tris pH 8.0. This suspension was transferred to a fresh eppendorf tube containing 500 μL of acid washed glass beads (Sigma), and mixed on the max setting in a Bead-Beater (BioSpec, Bartlesville, Okla.) for 3 minutes at 4° C. The samples were cleared by centrifugation at 14,000×g, and 400 μL of supernatant was precipitated with 400 μL of 10% TCA on ice. After clearing by centrifugation at 14,000×g for 20 minutes at 4° C., the extracts were resuspended in SDS loading buffer and subjected to SDS-PAGE analysis. Following electrophoresis, proteins were transferred to nitrocellulose membrane and detected with LexA antisera and secondary antibodies linked to alkaline phosphatase by standard protocols (Jain et al., J. Biol. Chem 269: 31518–31524, 1994).

Transient Transfection of Hep 3b Cells. pGL2EPOEN was cotransfected with pSport, PL464 (pSportMOP1), or PL477 (pSportMOP2) using the Lipofectin protocol (Life Technologies, Inc.). Briefly, the expression vector was mixed with the epo-reporter and the beta-galactosidase control plasmid pCH110 (Clontech) at a 3:1 charge ratio of TFX-50 reagent (Promega) and incubated for 15 minutes at room temperature. The lipofection media (200 μL) was added to Hep3b cells in 4 cm plates in the presence of serum. The cells were incubated at 37° C. for 2 hr. Following incubation, fresh media was added, and the cells were incubated for an additional 48 hours prior to harvesting. Cell extraction and beta-galactosidase assays were performed using the Galacto-Light assay according to manufacturer's protocols (Tropix).

Coimmunoprecipitation with Hsp90. Each MOP construct was in vitro translated in the presence of [$^{35}$S]-methionine in a TNT coupled transcription/translation system (Promega). Hsp90 immunoprecipitation assays were performed with monoclonal antibody 3G3p90 or a control IgM antibody, TEPC 183 (Sigma) essentially as described. Each immunoprecipitation was subjected to SDS-PAGE, and the resulting gel was dried. The level of radioactivity in each coprecipitated protein band was quantified on a Bio-Rad GS-363 Molecular Imager System. The amount of protein immunoprecipitated with the Hsp90 antibody is presented as a percentage of the amount of murine AHR immunoprecipitated in parallel assays.

Results

EST Search. Our initial BLAST searches in December 1994 were performed with the bHLH-PAS or PAS domains of all family members known at that time (AHR, ARNT, SIM and PER). In these searches we identified an EST clone, hbc025, derived from human pancreatic islets (Table 1) (Takeda et al., Hum. Mol. Genet. 2: 1793–1798, 1993). To confirm this similarity, we performed a BLASTX search, comparing hbc025 to the GenBank database and found that this sequence was most homologous to *Drosophila* SIM. This EST clone was designated MOP1. The bHLH-PAS domains of all family members, including MOP1, were again searched from May to October of 1995. Human ESTs that recorded BLASTN scores above 150 were again retrieved and confirmed using the BLASTX algorithm. This routine resulted in the discovery of six ESTs with significant homology to the bHLH-PAS domains of known members (Table 1).

cDNA Cloning. In order to more completely characterize the similarities and domain structures of the candidate clones, an anchored-PCR strategy was employed to obtain additional flanking cDNA sequence using phagemid libraries as a template. Comparison of amino acid sequences of these bHLH-PAS proteins is displayed in FIG. 2. Upon characterization of the open reading frames, it was learned that two of these ESTs (F06906 and T77200) corresponded to the same gene product (Table 1). Thus, we designated these remaining five unique cDNAs as "Members of PAS superfamily" or MOPs 1–5. The PCR strategy provided what appeared to be the complete ORFs of MOP1, MOP2 and MOP3 based upon the following criteria: (1) at their 5' ends these clones contain an initiation methionine codon (AUG) downstream of an in-frame stop codon, and (2) at their 3' ends these clones contain an in-frame stop codon followed by no obvious open reading frames. In addition, the nucleotide sequences flanking of the MOP1 and MOP2 most 5' AUG codons (see GenBank accessions U29165 and U51626) are in reasonable agreement with the proposed optimal context for translational initiation, i.e., CCACC AUGG (Kozak, Cell 44: 283–292, 1986; Kozak, Nucl. Acids Res. 15: 8125–8132, 1987).

Using the same anchored-PCR technique, we were unable to obtain the complete open reading frames of MOP4 or MOP5. This may have been due to the low copy number of these mRNAs in the tissues from which our PCR source cDNA was obtained (see below). We did identify a potential start methionine for MOP4 and the 3' stop codon for MOP5 (FIG. 2). Our preliminary designation of the MOP4 start methionine is tentative and is based only on its proximity to the start methionines of MOP1, MOP2, MOP3, AHR and SIM (FIG. 2) (Burbach et al., Proc. Natl. Acad. Sci. USA 89: 8185–8189, 1992; Nambu et al., Cell 67: 1157–1167, 1991). The fact that only one of the six nucleotides flanking the MOP4 AUG codon (ATTTAATGG) matches the consensus sequences for optimal translational initiation provides an indication that a more 5' initiation codon may exist. Therefore, the initiation codon of MOP4 is uncertain and that of MOP5 remains to be identified. This low level expression is consistent with our difficulties in amplifying these cDNAs by PCR (see above) and suggests that expression may be limited to specific cell types or developmental time periods not identified in our study.

Tissue Specific Expression. To characterize the tissue specific expression patterns of the MOP mRNAs, Northern blots of poly A(+) RNA from eight human tissues were probed with random primed cDNA restriction fragments. Single transcripts of 3.6 kb (MOP1/HIF1α), 6.6 kb (MOP2) and 3.2 kb (MOP3) were detected. Expression levels of each mRNA varied significantly between tissues, with MOP1 being highest in kidney and heart, MOP2 highly expressed in placenta, lung, and heart, and MOP3 highly expressed in skeletal muscle and brain. No detectable message was detected for MOP4 or MOP5 by our northern blot protocol.

Identification of Novel AHR or ARNT Partners:

1. Interaction of MOPs with the AHR and ARNT in vitro; Coimmunoprecipitation experiments. We first performed coimmunoprecipitation experiments to determine if MOPs 1–4 had the capacity to interact with either the AHR or ARNT in vitro. These proteins were expressed in a reticulocyte lysate system in the presence of $^{35}$S-methionine and then incubated in the presence or absence of the AHR or ARNT. Complex formation was assayed by coimmunoprecipitation with AHR or ARNT specific antisera, followed by quantitation of coimmunoprecipitated $^{35}$S-labeled MOP by phosphoimage analysis. Interactions were identified by a reproducible increase in an AHR or ARNT-dependent precipitation of MOP protein. Because we have observed considerable variability in this coimmunoprecipitation assay, each experiment was performed at least three times.

In the AHR interaction studies, we observed that MOP3 was coimmunoprecipitated with AHR. The positive control, ARNT-AHR interaction, was also reproducible, but weaker. Neither MOP1, MOP2 or MOP4 could be shown to interact with the AHR by this protocol. The ARNT protein displayed a broad range of interactions and was shown to coimmunoprecipitate with AHR (positive control), MOP1 and MOP2, but not MOP3 or MOP4.

Figure 3A:
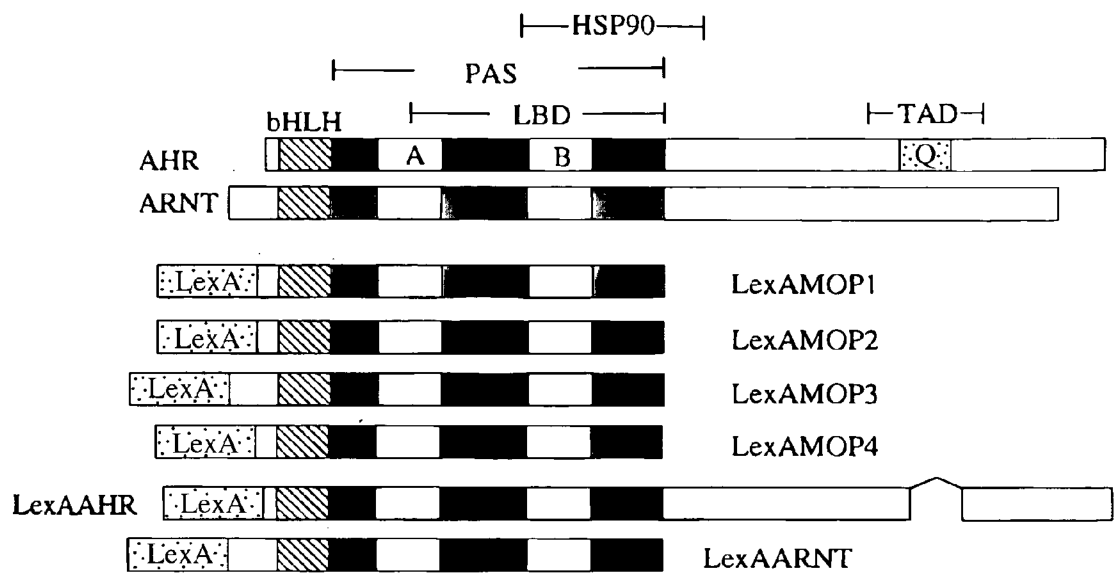
FIG. 3A, schematic of AHR, ARNT, and LexA fusion constructs. Panel shows a schematic of the AHR, with the PAS domain (black) with the characteristic "A" and "B" repeats (white), the bHLH domain (striped), and the variable C terminus (white). The transcriptionally active glutamine rich domain is indicated with "Q" (shaded box). LexA fusion proteins are indicated with the N terminus of LexA DNA-binding protein fused to bHLH-PAS domains of MOPs 1–4, and ARNT. The LexAAHR construct contains the bHLH-PAS domains and the C terminus minus the transcriptionally active Q-rich region (see Example 1, "Materials and Methods").

2. Interaction of MOPs with the AHR and ARNT in vivo; Yeast two-hybrid experiments. To determine if MOP-AHR or MOP-ARNT complexes could form in vivo, a modified interaction trap was employed (Fields & Song, Nature 340: 245–246, 1989; Chien et al., Proc. Natl. Acad. Sci. USA 88: 9578–9582, 1991) (FIG. 3). Fusion proteins were constructed in which the DNA binding domain of the bacterial repressor, LexA, was fused to the bHLH-PAS domains of the MOP proteins (FIG. 3A). The bHLH-PAS domains were chosen because they harbor both the primary and secondary dimerization surfaces of this family of proteins and they do not harbor transcriptional activity that would interfere with this assay (Jain et al., 1994, supra). Interactions were tested by cotransformation of each LexAMOP construct with either the full length AHR or ARNT into the L40 yeast strain, which harbors an integrated lacZ reporter gene driven by multiple LexA operator sites. In this system, LexAMOP fusions which interact with AHR or ARNT drive expression of the lacZ reporter gene.

We assessed the relative strength of these interactions by both a direct lacZ plate assay and by quantitation of the reporter activity in a liquid culture (FIG. 3). In all cases, these two methods of detection were equivalent. To test the validity of this model system as a method to detect bHLH-PAS interactions, LexAAHR and LexAARNT constructs were cotransformed with either the full length ARNT or AHR. In these control experiments, we were able to demonstrate the specificity of AHR-ARNT interaction and its dependence on the presence of the agonist βNF. The LexAAHR-ARNT interaction in the presence of βNF was 913 fold above background, while the LexAARNT-AHR interaction in the presence of βNF was 14 fold above background. Both combinations showed ligand inducibility. The LexAAHR-ARNT interaction in the presence of βNF was 6.4 fold over LexAAHR-ARNT in the absence of ligand, while the LexAARNT-AHR interaction in the presence of βNF was 2.0 fold over LexAARNT-AHR in absence of ligand. Despite our ability to readily detect the agonist-induced LexAARNT-AHR interaction in the two hybrid system, we were unable to detect any LexAMOP that could interact with the AHR. That is, none of the LexAMOP fusion proteins appeared to interact with cotransformed AHR and drive lacZ expression in the absence or presence of ligand.

Figure 3B:
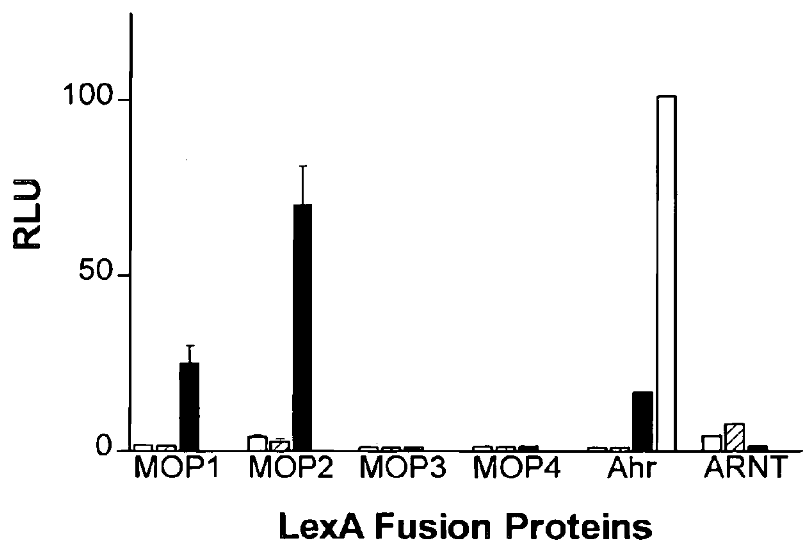
FIG. 3B, relative interaction of LexA fusion proteins with the AHR or ARNT. Galacto-Light assays were performed on yeast extracts prepared from colonies expressing LexAMOPs, LexAAHR, or LexAARNT and ARNT or AHR in the presence and absence of 1 μM βNF. Assays were performed in triplicate, and then the relative light units normalized to the LexAAHR-ARNT+βNF condition internally (set as 100%). The stippled bars represent LexA fusion proteins co-expressed with the full-length AHR in the presence of 1 μM βNF, the striped bars represent the fusion proteins co-expressed with the full length AHR in the absence of ligand, the shaded bars indicate the fusion proteins co-expressed with the full-length ARNT, and the open bar indicates LexAAHR co-expressed with full-length ARNT in the presence of 1 μM βNF.

Two of four MOP proteins tested were found to interact with ARNT in the two hybrid assay. Both the LexAMOP1 and LexAMOP2 interactions with full length ARNT were extremely robust, 36 and 28 fold above background, respectively (FIG. 3B). When compared with the LexAAHR-ARNT interaction in the presence of βNF, the LexAMOP1-ARNT and LexAMOP2-ARNT interactions were 24% and 69% as intense. These differences in LexAMOP1-ARNT and LexAMOP2-ARNT interaction could be attributed to differences in expression levels or to subtle differences in vector construction. To control for relative expression of the LexAMOP fusions, protein extracts were prepared and western blot analysis was performed with LexA specific antisera. We observed expression for each LexAMOP fusion proteins, indicating that negative results with LexAMOP3 and LexAMOP4 are not due to lack of expression.

3. DNA binding and specificity. Prompted by the observation that MOP1 and ARNT and MOP2 and ARNT specifically interact, we next examined the ability of MOP-ARNT dimeric complexes to bind those DNA response elements recognized by other bHLH-PAS protein complexes. Reports from a number of laboratories have demonstrated that bHLH-PAS dimers can bind to a variety of DNA elements: "DRE," TNGCGTG (Denison et al., J. Biol. Chem. 264: 16478–16482, 1989); "CME," ACGTG (Wharton et al., Development 120: 3563–3569, 1994); "SAE," GTGCGTG (Swanson et al., J. Biol. Chem. 270: 26292–26302, 1995); and "E-box," CANNTG (Sogawa et al., Proc. Natl. Acad. Sci. USA 92: 1936–1940, 1995; Swanson et al., 1995, supra). Using a gel-shift assay, we observed that MOP1-ARNT complexes specifically bound CACGTG and TACGTG, while the complex failed to bind GTGCGTG, TTGCGTG, and a non-palindromic E-box, CATGTG. Previous reports have demonstrated that ARNT homodimers are capable of binding the CACGTG sequence in vitro, and that this complex can drive reporter gene expression in vivo (Sogawa et al., 1995 supra, Swanson et al., 1995, supra). Our results suggest that the MOP1-ARNT dimeric complex binds the CACGTG oligonucleotide with a higher affinity than either MOP1 or ARNT alone. MOP1 failed to form a productive DNA binding complex with the AHR with any of the bHLH-PAS family response elements. As a comparison of MOP1-ARNT and MOP2-ARNT DNA binding, we provide results from gel shift assays using a double-stranded oligonucleotide containing a core TACGTG hexad binding site. WE observed that both MOP1-ARNT and MOP2-ARNT bound the TACGTG-containing oligonucleotide with approximately equal capacity and neither ARNT, nor MOP1, nor MOP2 could bind this DNA sequence alone. As additional controls, we confirmed the presence of the MOP proteins in the complex by showing that antisera raised against these proteins retarded the mobility of the complex.

4. Interaction of MOPs with Hsp90. In an effort to assess a MOP's ability to interact with Hsp90, we performed coimmunoprecipitation assays with anti Hsp90 antibodies. Given the remarkable stability of the Hsp90 complex with the AHR from the C57BL/6J mouse, we used this receptor species as a reference and compared all interactions relative to it. As additional controls, we immunoprecipitated ARNT and the human AHR as negative and positive controls, respectively. Despite our ability to readily detect huAHR-Hsp90 interactions, we were unable to detect ARNT, MOP2 or MOP5 interactions with Hsp90. In contrast, huAHR, MOP1, MOP3 and MOP4 all immunoprecipitated with HSP90-specific antisera. MOP3 formed the tightest interaction with HSP90, followed by the huAHR, MOP4 and MOP1 (71%, 53%, 31% and 17%, respectively).

Discussion

Since cDNAs encoding the complete open reading frames for MOPs 1–3 were available, most of the studies described in this example focused on those proteins. MOP4 was also included in some studies since our clone contained the sequences involved in dimerization, transcriptional activation and DNA binding of other bHLH-PAS proteins. Given the limited sequence information on MOP5, this clone was typically not included in functional studies.

Tissue specific expression. We observed that each MOP mRNA displayed a unique tissue specific distribution with MOP1 being highest in kidney and heart, MOP2 highly expressed in placenta, lung, and heart, and MOP3 highly expressed in skeletal muscle and brain. Previous studies conducted in our laboratory indicated that ARNT is expressed highly in skeletal muscle and placenta, while the AHR is most prevalent in placenta, lung, and heart (Carver et al., 1994, supra; Dolwick et al., 1993, supra). The observation that these bHLH-PAS proteins are coexpressed in a variety of tissues supports the idea that cross talk between these signaling pathways may be occurring in vivo and that multiple tissue specific interactions may be taking place. We also observed that AHR and MOP2 have very similar expression profiles in human tissues. An additional and equally important interpretation of these unique MOP expression profiles is that unidentified partners exist for these bHLH-PAS proteins and that they regulate a number of undescribed biological pathways.

Interactions. Our interaction screening strategy was based on the large amount of functional data and the detailed domain maps available for the AHR and ARNT. An important assumption used in the design and interpretation of our studies is that some of the MOPs may be constitutive interactors in vivo (like ARNT) and others may be conditional interactors that require activation in order to dimerize in vivo (like AHR). We chose to employ coimmunoprecipitation as an initial interaction screen for a number of reasons. First, AHR and ARNT-specific antibodies are available that have been shown to pull down AHR-ARNT complexes. This suggests that if MOP-AHR or MOP-ARNT interactions occurred in vitro, that these same antibodies would recognize and pull down such complexes. Second, data from a number of laboratories, using independently derived antibodies indicates that coimmunoprecipitation of AHR-ARNT complexes is independent of AHR-ligand. This observation suggests that AHR or ARNT interactions with conditional MOP proteins might still be identified by coimmunoprecipitation even in the absence knowledge about how to activate a conditional MOP (e.g., identification of a ligand).

As a secondary screen to characterize interacting MOPs, we employed a yeast interaction trap commonly referred to as the "Two Hybrid Assay". Support for use of this system comes from our previous observation that LexA-AHR chimeras are functional in yeast and provide a good model of AHR signaling and ARNT interaction. In addition, this method provides an independent confirmation of those interactions identified by coimmunoprecipitation and also provides a demonstration that interactions can occur in vivo. One major limitation of this system is that it may be insensitive at detecting conditional MOPs that require activation prior to dimerization. An example of this can be seen with the AHR and ARNT. In the absence of ligand, the AHR appears to reside primarily in the cytosol and ARNT appears to be primarily nuclear. This compartmentalization appears to be part of a cellular mechanism to prevent interaction of these proteins and minimize constitutive activity of the complex. It is important to point out that compartmentalization is only one component of AHR regulation, since ligand dependent DNA binding does occur in vitro in the presence of ARNT. Nevertheless, in vivo systems like the Two Hybrid Assay may yield false negative results for conditional MOP protein interactions that require an upstream activation event prior to nuclear transloction.

In light of the above considerations, our interpretation of the coimmunoprecipitation and two hybrid interaction results were as follows: First, since the MOP1-ARNT and the MOP2-ARNT interactions were confirmed in two independent systems these interactions should be pursued further (see below). Second, the observation that MOP3 interact with the AHR in vitro, but not in vivo, suggests that MOP3 may be a conditional MOP that has the capacity to interact with the AHR in vivo. This idea gained support from Hsp90 interaction studies (below). Third, the suspicion that MOP3 is a conditional bHLH-PAS protein, coupled with the observation that MOP3 and AHR have the disparate expression profiles led us to delay study of this interaction until we learn how to activate MOP3 or until we have evidence that these two proteins are expressed in the same cell type. Fourth, our observation that ARNT can form dimers with two out of four MOPs examined suggests that ARNT is a highly promiscuous bHLH-PAS partner that may be a focus of cross talk between different MOP signaling pathways. The multiplicity of ARNT partnerships is supported by recent observations from a number of laboratories (Sogawa et al, 1995, supra; Swanson et al., 1995, supra).

MOP1 and MOP2 interactions with ARNT. The concordance of the coimmunoprecipitation and two hybrid data led us to pursue the MOP1-ARNT and MOP2-ARNT interactions further. Given the pairing rules deduced from the interaction studies described above, we next attempted to determine if the MOP1-ARNT and MOP2-ARNT complexes bound specific DNA sequences in vitro. Earlier reports indicated that the basic region of each bHLH partner generates specificity for a distinct DNA half-site of at least 3 bp. Data from a number of laboratories has indicated that the ARNT protein displays specificity for the 3' GTG half site of the hexad target sequence, 5'NNCGTG3', where 5'NNC is the half site of the ARNT partner. To determine the half site specificity of the MOP1 protein when complexed with ARNT, we used gel shift analysis with oligonucleotides containing substitutions at the two variable 5' positions of 5'NNCGTG3'. These preliminary experiments indicated that MOP1-ARNT complex had greatest affinity for the 5'CAC and 5'TAC half sites.

Because the MOP1 and MOP2 basic regions differed by only one amino acid residue and since this residue is not thought to be in a DNA contact position, we hypothesized that MOP2 would bind the same DNA sequences. To confirm this, we performed MOP2-ARNT gel shift assays using a double stranded oligonucleotide containing a core TACGTG hexad binding site. We observed that both MOP1-ARNT and MOP2-ARNT bound the TACGTG containing oligonucleotide, that neither MOP1 nor MOP2 could bind this sequence in the absence of ARNT. As additional controls, we confirmed the presence of the MOP1 and MOP2 proteins in the complex by showing that antisera raised against these proteins retarded the mobility of the complex.

To assay MOP1-ARNT and MOP2-ARNT interactions in vivo, we constructed a luciferase reporter driven by the hypoxia responsive TACGTG containing enhancer from the human EPO gene. Our transient expression experiments in Hep3B cells consisted of cotransfection of this reporter with vector control, MOP1, or MOP2 in the presence or absence of cobalt chloride to stimulate the hypoxia heme sensor.

ARNT has been shown previously to be expressed in Hep3B cells. This experiment confirmed that the TACGTG-containing enhancer sequence is responsive to cobalt and cotransfected MOP1 or MOP2 under normal oxygen tension. The transfected MOP1 construct appeared to be responsive to hypoxia (3.5-fold over control), while the MOP2 construct was only slightly responsive (1.2-fold). MOP2 was more potent than MOP1 in driving expression of this reporter gene both in the presence and absence of cobalt chloride. This difference in efficacy of the MOP1 and MOP2 reporter plasmid in Hep3B cells could be explained by three possibilities: (1) the relative potency of the MOP2 transactivation domain may be much greater than MOP1; (2) the relative expression of MOP2 may be greater in this transient expression system than MOP1; or (3) the MOP1 may be partially repressed in vivo, by HSP90, while MOP2 is not (see HSP90 discussion below). Given that our MOP2 antisera are not useful in western blots, we could not assess the relative expression or stability of the MOP1 and MOP2 clones in this system.

MOP3 is a conditionally active bHLH-PAS protein. Data from a number of laboratories suggests that Hsp90 represses AHR activity by anchoring the receptor in the cytosol away from its nuclear dimeric partner ARNT. Ligand binding appears to weaken the Hsp90 association and induce a translocation of the Hsp90-AHR complex to the nucleus where dimerization with ARNT can occur.

Two lines of evidence suggest that MOP3, like the AHR, may be a conditionally active bHLH-PAS protein and that in the absence of an unidentified cognate ligand, might be repressed and unable to dimerize in vivo. First, MOP3 interacts with HSP90 even more efficiently than human AHR, suggesting that MOP3 may be functionally repressed or anchored in the cytosol like the AHR. Second, MOP3 interacts with AHR in the coimmunoprecipitation assay, but not in the yeast interaction trap. Similarly, the AHR interacts with ARNT in the coimmunoprecipitation assay, but interacts weakly, if at all, in the absence of ligand activation.

Alternative explanations for the different MOP3-AHR interaction results obtained from our in vitro and in vivo systems should also be considered. For example, the structure of MOP3 may be different than the AHR and ARNT, such that positioning of the LexA domain adjacent to the bHLH-PAS domain may sterically hinder dimerization surfaces within this protein or lead to improper subcellular localization or instability of the chimera. One example of the potential negative impact of context sensitivity in the two-hybrid system can be observed in FIG. 3. The LexAAHR-ARNT interaction is 14.7 times more robust than the LexAARNT-AHR interaction. In addition, the LexAAHR-ARNT interaction is more responsive to the AHR ligand βNF than the LexAARNT-AHR combination (6.4-fold and 2.0-fold, respectively). This difference cannot be explained by the relative transactivation potencies of the transactivation domains of AHR and ARNT in yeast, and therefore must be the result of context sensitivity. A final consideration is that coimmunoprecipitations may be capable of detecting weak interactions that cannot be maintained at the low cellular concentrations of the various MOPs. Thus, the MOP3-AHR dimerization may be too weak to occur in vivo. In this regard, we have previously reported ARNT—ARNT homodimers that bind specific DNA enhancer sequences in vitro, but they are weakly active, if active at all, in vivo (Swanson et al., 1995, supra).

It is also important to note that MOP1 and MOP4 also interact with HSP90 in the coimmunoprecipitation assay, albeit less strongly than MOP3 or human AHR. The relatively weak interaction of MOP1 with HSP90 may be an indication that this protein is partially repressed in vivo and that it may have both constitutive and conditional activity. Such a phenomenon might explain why MOP1 has less transcriptional activity in our in vivo systems than MOP2, which does not interact with HSP90. Finally, MOP4 did not interact with the AHR or ARNT in either the coimmunoprecipitation assay or the interaction trap. Although our experience with AHR indicates that interactions with conditional bHLH-PAS proteins can be observed by coimmunoprecipitation assays, MOP4's interaction with HSP90 may also indicate a requirement for activation and may inhibit the sensitivity of detecting interactions in vivo.

EXAMPLE 2

MOP3 Forms Transcriptionally Active Complexes with Circadian and Hypoxia Factors As described above, a number of "orphan" bHLH-PAS proteins have emerged from searches of expressed sequence tag databases and low stringency hybridization screens. For newly discovered bHLH-PAS proteins that have close homologs (e.g., HIF1α and HIF2α (MOP2), or ARNT and ARNT2), partnering and DNA binding specificity can often be predicted from amino acid sequence similarities in their bHLH-PAS domains. For divergent orphans like MOP3, MOP4, and MOP5, amino acid sequence does not provide the information necessary for similar predictions. To characterize this class of orphans, we have employed a series of assays that allow us to: (i) identify heterodimeric partnerships, (ii) determine the DNA response element bound by these heterodimers, (iii) verify that these complexes drive transcription in mammalian cells, and (iv) identify those tissues where these partnerships may occur. This example describes application of this approach to two bHLH-PAS orphans, MOP3 and MOP4.

Materials and Methods

Reagents. Oligonucleotides were supplied by GIBCO/BRL and designated as follows:

OL522 5'-GACAGTATCACGCCTCTCCTT-3' (SEQ ID NO:78)

OL579 5'-AGCGGCGTCGGGATAAAATGA-3' (SEQ ID NO:79)

OL595 5'-ATGCTGAACTGTGCCGAAAACTGT-3' (SEQ ID NO:80)

OL656 5'-GAACAGTGGGGTGGGTCCTCTTT-3' (SEQ ID NO:81)

OL990 5'-GGAATTCTGAGTCTGAAC-3' (SEQ ID NO:82)

OL991 5'-GGAATTCCACGCTCAGG-3' (SEQ ID NO:83)

OL992 5'-GGAATTCTGAGTCTGAAC(N)13CCT-GAGCGTGGATTCC-3' (SEQ ID NO:84)

OL116 5' GATCGGACACGTGACCATTGGTCACGT-GTCCATTGGACACGTGACC-3' (SEQ ID NO:85)

OL117 5'-GATCGGTCACGTGTCCAATGGACACGT-GACCAATGGTCACGTGTCC-3' (SEQ ID NO:86)

OL155 5'-GATCGGATACGTGACCATTGGTTACGT-GTCCATTGGATACGTGACC-3' (SEQ ID NO:87)

OL156 5'-GATCGGTCACGTATCCAATGGACACG-TAACCAATGGTCACGTATCC-3' (SEQ ID NO:88)

The yeast LexA fusion plasmid pBTM116 was provided by P. Bartel and S. Fields (State University of New York, Stony Brook). The yeast strain L40 was a kind gift of S. Hollenberg (Fred Hutchinson Cancer Research Center, Seattle, Wash.). The yeast strain AMR70 was constructed by Rolf Stemglanz, and was a kind gift of S. Hollenberg. LexA antiserum was a kind gift of J. W. Little (University of Arizona). pSGBCU11 was a kind gift of Stephen Goff (CIBA-Geigy, Research Triangle Park, N.C.). Human CLOCK was a kind gift of T. Nagase (Kazusa DNA Research Institute, Chiba, Japan). Mammalian expression vectors were purchased from GIBCO/BRL (pSVSport) and Promega (pTarget). Antibodies specific for MOP3 and MOP4 were prepared against peptides specific for each protein as described (Poland et al., 1991, Mol. Pharmacol. 39: 20–26). The MOP3 peptide sequence was DNDQGSSSPSNDEAAC (SEQ ID NO:125) and the MOP4 peptide sequence was KDKGSSLEPRQHFNALDVGC (SEQ ID NO:126).

Expression Plasmid Construction. Yeast expression plasmids harboring the LexA DNA binding domain fused to the bHLH-PAS domains of HIF1α (PL856), HIF2α (PL857), MOP4 (PL859), AHR (PL739), and ARNT (PL701) have been described (Example 1). LexAbHLH-PAS fusion plasmids for MOP3 (PL831) and CLOCK (PL828) were constructed in pBTM116 by an identical approach. Plasmids harboring the full-length ORFs of MOP3, MOP4, and CLOCK were constructed by PCR amplification of the ORF of each cDNA and cloned into the appropriate vectors for expression in yeast or mammalian systems. For yeast expression of full-length proteins, PCR products were cloned into the appropriate sites of pSGBCU11. For mammalian expression, PCR products were cloned into pSVSport and pTarget. The yeast expression vector for full-length ARNT has been described (PL574) (Example 1). The yeast expression vector for full-length MOP3 was designated PL694. Mammalian expression vectors for ARNT (PL87), HIF1α (PL611), and HIF2α (PL447) have been described (Example 1; Jain et al., 1994, J. Biol. Chen 269: 31518–31524). Mammalian expression vectors were constructed for MOP3 (PL691 and PL861), MOP4 (PL695 and PL871), and CLOCK (PL941).

Two-Hybrid cDNA Library Screen. The yeast interaction trap was performed using the yeast strain L40 (MATa, his3Δ200, trpl-901, leu2–3, 112, ade2, LYS::lexAop$_4$HIS, URA3::lexAop$_8$lacZ) or AMR70 (MATα, his3, lys2, trp1, leu2, URA::lexAop$_8$-lacZ) as described (Example 1; Carver and Bradford, 1997, J. Biol. Chem. 272: 11452–11456; Vojtek et al., 1993, Cell 74: 205–214). The bait plasmid (PL859) was a fusion of the bHLH-PAS domain of MOP4 to the DNA binding domain of LexA (Hogenesch et al., 1997, supra). The MOP4 bait construct was used to screen a human fetal brain cDNA library fused to the transactivation domain of Gal4 (CLONTECH) and transformants were plated on selective media (minus tryptophan, uracil, histidine, and leucine). The cDNAs from surviving colonies, positive for lacZ activity were sequenced by the chain termination method (Sanger et al., 1977, PNAS 74: 5463–5437). These sequences were analyzed using the BLAST algorithm (Altschul et al., 1990, J. Mol. Biol. 215: 403–410).

Interaction Screen Against Known bHLH-PAS Proteins. LexAbHLH-PAS fusion proteins ("baits") of HIF1α, HIF2α, MOP3, MOP4, AHR, ARNT, and CLOCK were transformed into the L40 strain of yeast. The full-length ("fish") MOP3 and ARNT plasmids were transformed into the AMR70 yeast strain, and these transformants were plated onto yeast complete media plates (Kaiser et al., 1994, in *Methods in Yeast Genetics*, Cold Spring Harbor Press, Plainview, N.Y.). The L40 yeast harboring the bait constructs were replica plated onto these yeast complete media plates and mated for 8 hr at 30° C. The plates were then replica plated onto selective media and grown for an additional day at 30° C. 5-Bromo-4-chloro-3-indolyl 13-D-galactoside (X-Gal) overlay assays were performed to determine the relative expression of the lacZ reporter gene (Bohen and Yamamoto, 1993, PNAS 90: 11424–11428). Western blot analysis, using LexA-specific sera, was performed on extract from each transformant to confirm expression of the fusion protein (see Example 1).

DNA Binding Specificity. To determine high-affinity DNA binding sites for MOP3-MOP4 heterodimers, site selection and amplification was performed as described (Swanson et al., 1995, J. Biol. Chem. 270: 26292–26302). Briefly, reticulocyte lysate expressed MOP3 and MOP4 proteins (−0.5 fmol each) were incubated with DNA oligonucleotide randomers corresponding to $-7\times10^7$ different nucleotide sequences. Randomers were generated and amplified by PCR using oligonucleotides OL990 and OL991 as primers and OL992 as template. After incubating the complexes with the randomers for 30 min at 30° C., samples were loaded directly on 4% polyacrylamide-TBE (90 mM Tris/64.6 mM boric acid/2.5 mM EDTA, pH 8.0) gels to separate MOP3-MOP4 bound DNA from free DNA (Swanson et al., 1995, supra). Gel slices corresponding to the migration of bound DNA were excised, incubated overnight in TE (10 mM Tris/1 mM EDTA, pH 8.0), and the eluate subjected to additional PCR using oligonucleotides OL990 and OL991.

Cell Culture and Transient Transfection. Transient transfections of COS-1 cells were performed by the Lipofectamine protocol (GIBCO) as described in Example 1. To mimic hypoxia, 100 μM of cobalt chloride was included in the cell growth media and incubated at 37° C. until harvest. To monitor the transcriptional activity of the MOP3-MOP4 or MOP3-CLOCK heterodimers, a synthetic reporter was constructed by annealing phosphorylated oligonucleotides OL1116 and OL1117 and cloning them into the BglII site in the reporter plasmid pGL3p (Promega). To measure the transcriptional activity of the MOP3-HIF1α or MOP3-HIF2α heterodimers, a synthetic reporter was constructed by annealing phosphorylated oligonucleotides OL1155 and OL1156 and then cloning them as above. Luciferase levels were reported in relation to β-galactosidase activity as described in Example 1.

mRNA Expression Analysis. To generate antisense riboprobes, partial cDNAs of the mouse MOP3 and MOP4 were cloned into plasmid vectors harboring bacteriophage promoters. A partial 1.2-kb mouse fragment of MOP3 was obtained by PCR of a mouse kidney cDNA library using oligonucleotides OL579 and OL656, and cloned into pGEM-T in the T7 orientation. For MOP4, reverse transcription-PCR was performed on 3 μg of E17.5d placenta total RNA with oligonucleotides OL522 and OL595. The resultant fragment was subcloned in PGEM-T in the 5P6 orientation. Total RNA from various mouse tissues was prepared using the Trizol reagent (GIBCO/BRL) according to manufacturer's protocols. Ribonuclease protection assay (RPA) was performed as described for both MOP3 and MOP4 (Luo et al, 1997, Gene Expression 6: 287–299). For in situ analysis, sense and antisense MOP3 and MOP4 riboprobes were generated with [α-[$^{35}$S]thio]UTP, 80 μCi (Amersham, >1,000 Ci/mmol; 1 Ci=37 GBq) as the radioactive ribonucleotide and subjected to alkaline hydrolysis for 13 min at 60° C. as described (Jain et al., 1998, Mech. Dev. 73: 117–123). Tissue sections (5 μm) were processed and hybridized with the specific riboprobes (Jain et al., 1998, supra).

Results

MOP4 Two-Hybrid Library Screen. The MOP4 bait plasmid was used to screen a human fetal brain cDNA library fused to the transactivation domain of Gal4. After screening $-7\times10^5$ colonies, 21 survived selection and were blue in the presence of 5-bromo-4-chloro-3-indolyl-β-D-galactoside. BLAST searches revealed that seven of these clones represented four independent MOP3 cDNA fragments. These cDNAs differed in their first 57 codons from the MOP3 cDNA we have described previously (GenBank accession no. U60415; SEQ ID NO:3). These 57 amino acids are identical to that reported by a second group, and appear to be derived from a second promoter (Ikeda and Nomura, 1997, Biochem. Biophys. Res. Commun. 233: 258–264). All subsequent functional studies were done using constructs derived from the MOP3 cDNAs identified by the yeast interaction trap.

Figure 6:
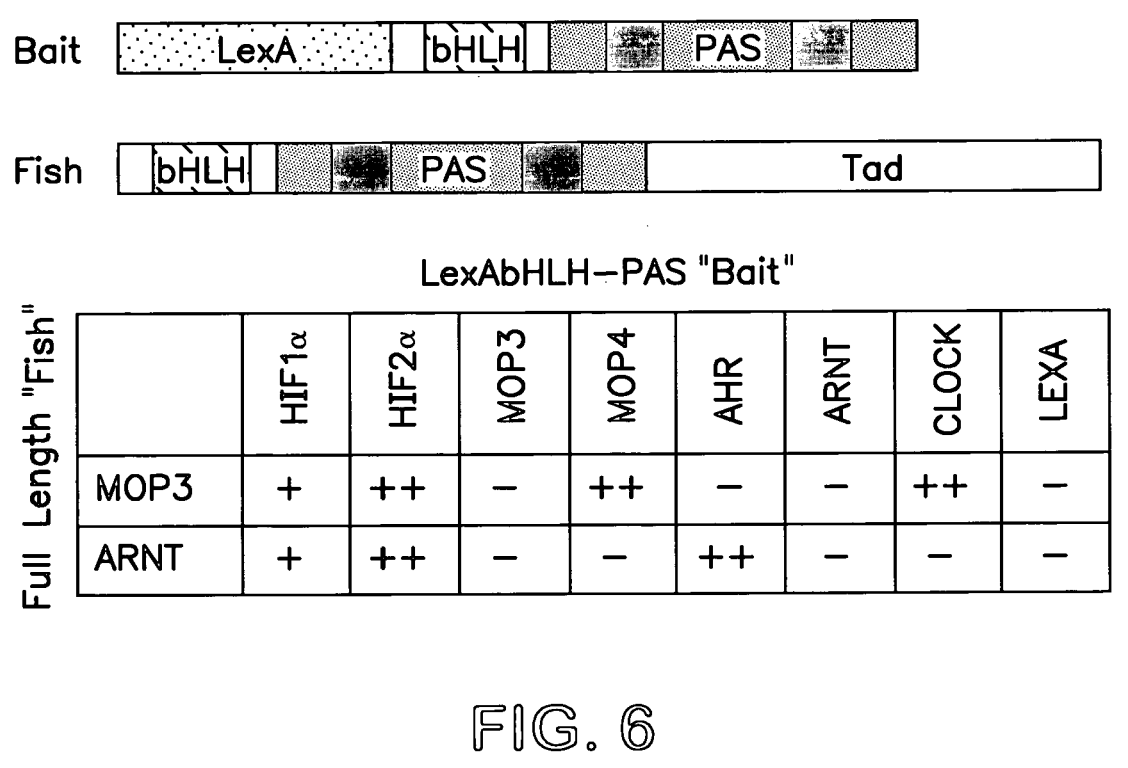

MOP3 and MOP4 Screened Against Known bHLH-PAS Proteins. To confirm the specificity of the MOP3-MOP4 interaction, we reversed the interaction trap strategy and screened full-length MOP3 against all bHLH-PAS proteins available in this laboratory. As a positive control we compared these results to a parallel screen using full-length ARNT. Western blot analysis using anti-LexA sera indicated approximately equal expression levels for all fusions. The full-length MOP3 protein interacted strongly with LexAbHLH-PAS fusions of MOP4, CLOCK, and HIF2α and weakly with HIF1α (FIG. 6). No interaction of full-length MOP3 could be detected with LexA fusions of MOP3, AHR, ARNT, or the LexA control. Full-length ARNT demonstrated robust interactions with HIF2α and the AHR, and weaker interactions with HIF1α. We did not detect full-length ARNT interactions with LexAbHLH-PAS fusions of MOP3, MOP4, CLOCK, ARNT, or the LexA control (FIG. 6).

DNA Binding Specificity of the MOP3-MOP4 Heterodimer. We performed a selection and amplification protocol to identify the DNA sequence bound with high-affinity by the MOP3-MOP4 complex. After three rounds of selection and amplification, a gel shift assay was performed using radiolabeled selected randomers to identify the migration of the complex. We identified a species dependent on the presence of both proteins. A band corresponding to this migration was excised from the polyacrylamide gel, and used as template for a fourth round of amplification before cloning the pool. Analysis of the sequencing data from 10 clones revealed that the MOP3-MOP4 heterodimeric pair bound the sequence G/TGA/GACACGTGACCC (SEQ ID NO:120) (FIG. 5). This sequence is an imperfect palindrome containing a core E-box enhancer element (defined as CANNTG, underlined) and specificity for nucleotides in the flanking region (e.g., +4 "A"). We refer to this response element bound by the MOP3-MOP4 as M34. To demonstrate sequence binding specificity and to confirm the selectivity for the +4 nucleotide, we performed competition experiment varying the +4 position to A, C, G, or T (FIG. 5). In agreement with our selection results, we observed a strong preference for the flanking +4 "A" nucleotide by the MOP3-MOP4 complex.

MOP3 Forms Transcriptionally Active Complexes with MOP4 and CLOCK. To demonstrate that both MOP3 and MOP4 are required for binding to the M34 element, we performed additional gel shift experiments. A specific band was present only with the combination of MOP3 and MOP4, and was not present with either protein alone. As an additional specificity control, affinity-purified anti-MOP3 or anti-MOP4-specific Igs were used in gel shift experiments. Both MOP3-specific and MOP4-specific IgG were capable of retarding the mobility of the MOP3-MOP4 complex, while purified preimmune IgG alone was not.

To determine whether the MOP3-MOP4 complex could drive transcription in vivo, we constructed a vector with three copies of the M34 element upstream of a minimal simian virus 40 promoter-luciferase reporter. Upon cotransfection of the reporter plasmid into COS-1 cells with MOP3 and MOP4, we observed that this combination enhanced transcription 3.3-fold, while neither protein alone was capable of driving transcription over control. The observations that CLOCK also interacted with MOP3 in the yeast interaction trap (FIG. 5) and that CLOCK shares extensive homology with MOP4 prompted us to determine if MOP3-CLOCK complex could also drive transcription in vivo from an M34 element. Cotransfection of MOP3 and CLOCK revealed that this complex was also active, driving transcription 5.6-fold over control. Transfections with MOP3, MOP4, CLOCK, and ARNT alone, as well as combinations of ARNT and MOP3 or MOP4 failed to drive transcription over control.

MOP3 Forms Functional DNA Binding Complexes with HIF1α and HIF2α. Prompted by our yeast interaction results, we set out to determine the ability of MOP3 to form DNA binding complexes with HIF1α in vitro. Because of the asymmetry at the +4 position of the M34 element, we were uncertain which half-site was bound by MOP3. Therefore, we synthesized enhancer elements with the HIF1α 5' half site (TAC) fused to both of the potential MOP3 3' half-sites described above (GCCCTACGTGACCC, SEQ ID NO:121 or GCCCTACGTGTTCC; SEQ ID NO:122). We found that the HIF1α/MOP3 complex preferred the GCCCTACGTGACCC (SEQ ID NO: 123) element in vitro, suggesting that MOP3 preferred an "A" at the +4 position. Therefore the corresponding response element bound by the HIF1α-MOP3 complex, which we refer to as M13, was used in subsequent experiments. The results demonstrate that the M13 element is bound in the presence of the MOP3-HIF1α combination, but not by either protein alone. MOP3-specific and HIF1α-specific antisera abolished this complex while preimmune IgG did not. For comparison we included ARINT in these experiments, and found that ARNT-HIF1α band was more intense than the MOP3-HIF1α complex when all proteins were used at equimolar concentrations.

To determine if MOP3 formed a transcriptionally active complex with either HIF1α or HIF2α in vivo, we constructed a synthetic reporter using six copies of the M13 element described above. The M13 reporter was up-regulated when cotransfected with combinations of MOP3-HIF1α and MOP3-HIF2α (3.3-fold and 3.6-fold, respectively). ARNT formed more active complexes with both HIF1α and HIF2α (14.1-fold and 8.1-fold, respectively), consistent with our in vitro results. Like ARNT, upon exposure of these transfected cells to cobalt chloride to simulate cellular hypoxia, MOP3 interacted and drove transcription in complexes with both HIF1α and with HIF2α.

Coexpression of MOP3, MOP4, and HIF1α in Neonatal and Adult Murine Tissues. To determine if MOP3 was coexpressed with MOP4 in any murine tissue, ribonuclease protection assays (RPA) and in situ hybridization analysis were performed. Parallel RPA analysis of neonatal and adult tissues indicated that MOP3 was most highly expressed in brain, thymus, and muscle. MOP4 showed highest expression in the brain. We performed in situ hybridization analysis on tissues where RPA data indicated overlap between MOP3 and MOP4, or MOP3 and HIF1α. Sense controls were negative in all tissues except eye, where the pigment of the retina gave a nonspecific signal. In transverse sections of E15.5 brain, we observed that both MOP3 and MOP4 showed their highest expression levels in the thalamus. In E15.5 eye, we were able to detect colocalization of MOP3 and HIF1α in the retina, but were unable to detect specific labeling of MOP4. The results show that both MOP3 and HIF1α are colocalized in the thymic cortex of postnatal animals. Prompted by the observation of others that the MOP4 mRNA is expressed at low levels in the colon, we assayed that target tissue and observed that MOP4 and HIF1α were coexpressed in postnatal colonic mucosa, while MOP3 was undetectable there (Zhou et al., 1997, PNAS 94: 713–718).

Discussion

In an effort to determine the pairing rules of MOP3 and MOP4, we employed the yeast interaction trap to identify the bHLH-PAS partners of these orphans. Our initial experiment using a MOP4 bait construct to screen a brain cDNA library identified MOP3 as a partner. In further experiments, we reversed this approach and used full-length MOP3 to detect interactions with other bHLH-PAS members. This analysis confirmed the MOP3-MOP4 interaction and also demonstrated that CLOCK, HIF1α and HIF2α were additional partners of MOP3. As demonstrated previously, ARNT interacted with the AHR, HIF1α, and HIF2α, but not with MOP4 or CLOCK. The fact that both MOP4 and CLOCK interacted with MOP3 was not surprising given their 75% amino acid sequence identity in their bHLH-PAS domains. The observation that MOP3 was a partner of both HIF1α and HIF2α, but that it did not dimerize with the AHR in the yeast interaction trap was an unexpected result. Due to lack of expression in our yeast system, we were unable to examine the interactions of MOP3 or MOP4 with a number of additional bHLH-PAS proteins, including mSIM1, mSIM2, hARNT2, and hSRC1. Thus, we do not exclude the possibility that additional MOP3 and MOP4 interactions with these proteins may be important. Nevertheless, our data lead us to suggest that MOP3 is a general partner of a number of bHLH-PAS factors, with a distinct interaction profile from that of the more well characterized general partner ARNT.

Analysis of MOP3 and MOP4 revealed that these proteins did not share perfect identity with any other known bHLH proteins in their basic residues thought to contact DNA. Therefore, we could not readily predict the response elements that the MOP3-MOP4 heterodimer would bind. To overcome this limitation, we employed a DNA selection and amplification protocol and determined that the MOP3-MOP4 complex bound an E-box, with flanking region specificity for an "A" at +4 (i.e., <u>CACGTG</u>A, M34 element). In keeping with our prediction that MOP4 and CLOCK are functional homologs, transfection experiments demonstrated that the combination of either MOP3-MOP4 or MOP3-CLOCK was capable of driving transcription from M34 elements, while neither MOP3, MOP4, or CLOCK alone displayed this activity. In support of our argument that MOP3 harbors a partnering specificity distinct from that of ARNT, we observed that neither MOP3 nor MOP4 was capable of interacting with ARNT and driving transcription from the M34 element in its presence.

What could be the consequence of these interactions? Experiments from a number of laboratories indicate that circadian behavior may be regulated at the transcriptional level by complex interactions between multiple PAS domain containing proteins. Strong genetic evidence supports a role for CLOCK in the maintenance of circadian behavior in mice and the product of the period gene (PER) for control of circadian rhythms in *Drosophila*. The fact that MOP4 is a brain specific homolog of CLOCK and that these factors share MOP3 as a common dimeric partner suggests that both MOP3 and MOP4 may play a role in this process as well. In addition to the mammalian MOP3, MOP4 and CLOCK proteins, murine and human homologs of *Drosophila* PER have recently been characterized. Like *Drosophila* PER, the mRNA levels of these mammalian homologs respond to light and display circadian rhythmicity. Sequence analysis of PER proteins indicates that they contain PAS domains, but do not contain consensus bHLH domains. Coupled with additional biochemical evidence from others, these data suggest that PER proteins may affect their own transcription through interactions mediated by their PAS domains. Thus, these PERs may impact transcriptional activity of other bHLH-PAS dimers by acting as either dominant negative inhibitors that block pairing of trancriptionally active complexes, or they may act in a positive manner as coactivators of these complexes.

In addition to defining the pairing rules and DNA binding specificities of MOP3 and MOP4, our data lead us to a testable model that describes circadian oscillation of transcription. Without intending to limit the present invention by any particular explanation of mechanism, we speculate that MOP3-CLOCK or MOP3-MOP4 complexes regulate PER transcription through <u>CACGTG</u>A-containing enhancers. The transcriptional activity of these promoters could in turn be modified by feedback inhibition/activation by the PER protein products themselves. In support of this idea, an E-box element in the *Drosophila* PER promoter, required for normal cycling of the PER mRNA, bears striking resemblance to the M34 element we have identified (i.e., 5'-<u>CACGTG</u>AGC-3' compared with 5'-<u>CACGTG</u>ACC-3'). Given that we are borrowing from both *Drosophila* and mammalian systems, our model assumes that these signal transduction pathways have been largely conserved throughout evolution. In keeping with this idea, a search of *Drosophila* expressed sequence tags revealed the existence of an uncharacterized MOP4/CLOCK homolog (GenBank accession no. AA698290) and an uncharacterized MOP3 homolog (GenBank accession no. AA695336).

What could be the consequences of MOP3-HIF interactions? Transient transfection experiments showed that MOP3 formed transcriptionally active complexes with HIF1α and HIF2α and that these complexes responded to cellular hypoxia. MOP3 may play a specialized role in hypoxia signaling. The different tissue specific expression profiles of MOP3 and ARNT suggests that MOP3 may regulate cellular responses to hypoxia at distinct sites, such as the retina, thymic cortex, and thalamus. Moreover, the observation that MOP3 binds a GTG half-site with flanking region specificity for an "A" at +4, may indicate that MOP3/HIF complexes may have greater affinity for a distinct subset of hypoxia response elements (i.e., TACGTGA vs. the more commonly observed TACGTGG elements observed in known hypoxia responsive enhancers). Finally, the observation that MOP4 is expressed at a site where MOP3 expression appears low, i.e., colonic mucosa, suggests that additional partners may exist for MOP4 and CLOCK and that all bHLH-PAS signaling pathways may involve complex equilibria between multiple PAS proteins.

EXAMPLE 3

Chromosomal Localization and Molecular Characterization of MOP7 as a Third Hypoxia Inducible Factor Hypoxia inducible factors (HIFs) regulate transcriptional responses to low oxygen tension and other physiological conditions that rely upon glucose for cellular ATP. The HIFs are heterodimeric transcription factors that are composed of two bHLH-PAS proteins. The bHLH-PAS subunits can be classified as α-class or β-class. In addition to amino acid sequence similarity, the most distinguishing characteristic of the α-class subunits is that they are rapidly up-regulated by cellular hypoxia, or treatment with iron chelators and certain divalent cations (e.g. $Co^{++}$). The previously described α-class subunits are referred to as HIF1α (MOP1 herein) and HIF2α (MOP2 herein). In contrast, the β-subunits appear to be constitutively expressed and ready to pair with their up-regulated α-class partner. Recent evidence suggests that ARNT, ARNT2 and MOP3 are prototype β-class subunits. At the present time, a number of well-characterized HIF-responsive gene products have been identified. These genes include those encoding EPO, VEGF and GLUT1, among others. The promoters of these genes are regulated by HRE elements that are recognized by the HIFαβ heterodimer. The HREs contain the core TACGTG element and are found both 5' and 3' to the regulated promoter in a number of hypoxia responsive genes.

It is of academic and practical interest to understand how bHLH-PAS proteins signal, as well as the biological consequences that result from the sharing of bHLH-PAS partners. The recent generation of thousands of expressed sequence tags (ESTs) has provided the opportunity to identify and classify orphan HIF subunits based upon nucleotide sequence similarity with known bHLH-PAS proteins. As the result of these efforts, we have identified, and describe the cloning and characterization below, of a third HIF α-class subunit, referred to above as MOP7. For consistency of nomenclature, this protein also is referred to as "HIF3α". Using a number of biochemical approaches, we demonstrate that the MOP 7 (HIF3α) cDNA encodes a protein that meets the major criteria of an α-class HIF subunit. The observation that multiple HIF α and β subunits are encoded by the mammalian genome suggests that a complex array of subunit interactions and tightly controlled developmental expression patterns governs transcriptional response to hypoxic stress.

Material and Methods

Gel-shift oligonucleotides. The complementary oligonucleotide pairs used in gel-shift assays are shown below (5' to 3'). They contain a constant flanking sequence and the wildtype or mutant HRE core sequence (underlined):

OL396 TCGAGCTGGGCAGGTAAGGTGGCAAGGC (SEQ ID NO:89)

OL397 TCGAGCCTTGCCACGTTACCTGCCCAGC (SEQ ID NO:90)

OL398 TCGAGCTGGGCAGGTGAGGTGGCAAGGC (SEQ ID NO:91)

OL399 TCGAGCCTTGCCACGTCACCTGCCCAGC (SEQ ID NO:92)

OL414 TCGAGCTGGGCAGGGTAGGTGGCAAGGC (SEQ ID NO:93)

OL415 TCGAGCCTTGCCACGTACCCTGCCCAGC (SEQ ID NO:94)

PCR Oligonucletides:

OL1014 GCCATGGCGTTGGGGTGCAG (SEQ ID NO:95)

OL1017 ACTGTGTCCAATGAGCTCCAG (SEQ ID NO:96)

OL1178 GCCTCCATCATGCGCCTCACAATCAGC (SEQ ID NO:97)

OL1210 CCCCGTTACTGCCTGGCCCTTGCTCA (SEQ ID NO:98)

OL1323 AGCCGAGGGGGTCTGCGAGTATGTTGC (SEQ ID NO:99)

OL1324 GCTGCTGACCCTCGCCGTTTCTGTAGT (SEQ ID NO:100)

OL1397 GTCGACGCCACCATGGACTGGGACCAAGACAGG (SEQ ID NO:101)

OL1427 GGATCCTCAGTGGGTCTGGCCCAAGCC (SEQ ID NO:102)

OL1548 GCGGGGTGCTGGGAGTGGCTGCTAC (SEQ ID NO:103)

OL1698 GCCTTCCTGCACCCGCCTTCCCTGAG (SEQ ID NO:104)

OL1769 GCGGCCGCAAAAAACAAGACCGTGGAGACA (SEQ ID NO:105)

OL1771 GCCCTGGGAGAATAGCTGTTGGACTTTGGGCAATTGCTCACT (SEQ ID NO:106)

OL1772 GCGGCCGCCTATTCTGAAAAGGGGGGAAA (SEQ ID NO:107)

AP1 CCATCCTAATACGACTCACTATAGGGC (SEQ ID NO:108)

AP2 ACTCACTATAGGGCTCGAGCGGC (SEQ ID NO:109)

Figure 7:
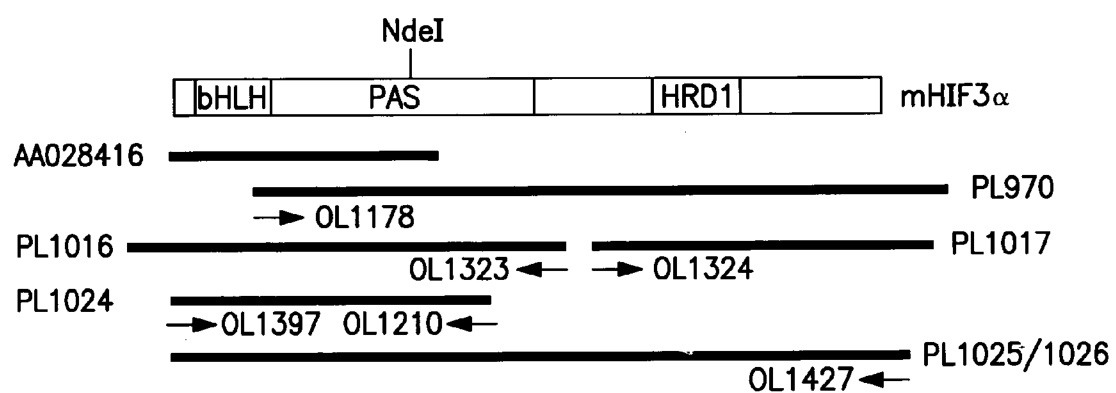
FIG. 7. Cloning of MOP7. The positions of the original EST clone (AA028416) and RACE products are shown as dark lines with the mMOP7 ORF shown as an open box. The PCR primers used are posted below the corresponding fragments and the plasmid numbers are marked on the side. The GenBank Accession Number for mouse MOP7 cDNA is AF060194.

Cloning of MOP7. TBLASTN and BLASTX algorithms were used to search nucleotide sequences corresponding to amino acids 54 to 125 of hHIF1α (http://dot.imgen. bcm.tmc.edu: 9331/seq-search/Options/blast.html) (Hwang et al., J. Mol. Cell. Cardiol. 26: 1329–1333, 1994). One mouse EST clone, Genbank Accession AA028416 (designated PL773), was found to encode a novel bHLH-PAS protein. To obtain the complete open reading frame, we performed a series of PCR amplifications using primer-anchored cDNA derived from mouse lung ("Marathon-Ready," Clontech) (Siebert et al., Nuc. Acids Res. 23: 1087–1088, 1995). A 3' rapid amplification of cDNA ends (RACE) reaction was performed using oligonucleotides OL1178 and anchor primer AP1. The product of this reaction was reamplified in a second reaction with OL1178 and AP2. The 2.0-kb 3' PCR product obtained by this protocol was cloned into the pGEM Teasy vector (Promega) and designated PL970. The clone was sequenced and found to contain an ORF followed by a translational stop site (FIG. 7). To confirm the position of the traslational stop site, OL1324 was used in an independent 3' RACE reaction. The 0.9 kb product was cloned into a pGEM Teasy vector (PL1017) and was found to contain the same stop codon (FIG. 7). To obtain the 5' end of the cDNA, OL1323 was used in a RACE reaction against oligonucleotide AP1. The 1.2 kb RACE product was cloned into PGEM Teasy vector (PL1016) and found to contain a translation start codon ATG followed by a long ORF. We define the nucleotide A from the initiation codon as position 1 of the cDNA. In addition, the translational start site is defined by the presence of an in-frame stop codon 51 nucleotides upstream. To generate expression plasmids containing the full ORF, a PCR reaction was performed using OL1210 and OL1397 with PL1016 as template. The PCR fragment was cloned into pGEM Teasy vector in the SP6 orientation and named PL1024. The NdeI digested PL1024 was then inserted into the NdeI digested PL970 to generate the full-length HIF 3α in the pGEM-Teasy vector (PL1025).

Construction of MOP7 expression plasmids. For MOP7 expression in mammalian cells, the ORF was amplified by PCR using OL1397 and OL1427 with PL1025 as template. The resultant plasmid was cloned into pTarget vector downstream of the CMV promoter (Promega) and was named PL1026 (FIG. 7).

To confirm the hypoxia inducibility of MOP7, we constructed a fusion protein comprised of the DNA binding domain from GAL4 (residues 1–147), the predicted hypoxia responsive domain-1 (HRD1) from mMOP7 (residues 453–496), and the transactivation domain (TAD) from hARNT (residues 581–789). The HRD1 was amplified using OL1769 and OL1771 with mMOP7 as template. To form the HRD1/TAD chimera, the resultant PCR fragment from above was used as a megaprimer in a second PCR reaction with OL1772 as the second primer and hARNT as the template (Barik et al., Biotechniques 10: 489–490, 1991). The HRD1/TAD chimeric fragment was cloned into the NotI site of the GAL4 fusion vector pBIND (Promega) and designated PL1131.

Structural gene analysis and chromosomal localization. The MOP7 insert from PL773 was cut with EcoRI/NdeI and the 0.6-kb fragment was purified and used as a probe to screen for bacterial artificial chromosome (BAC) clones containing the mouse MOP7 gene (Genome Systems, Inc.). Oligonucleotides derived from the mMOP7 sequence were used as primers to sequence the BAC DNA, and the splice sites were deduced by comparing the genomic and cDNA sequences. To obtain BACs containing the human MOP7, oligonucleotides OL1014 and OL1017 were used in a PCR reaction with human heart cDNA as template (Clontech) to amplify a MOP7 fragment (Genbank Accession No. AF079154). This fragment was subcloned into the pGEM-Teasy vector, confirmed by sequencing, and used as a probe to screen for a BAC clone harboring the human structural gene for MOP7 as above. The identity of the resultant BAC was confirmed by direct sequencing using primers specific for hMOP7. The human MOP7 chromosomal location was identified by PCR reactions against human/hamster somatic cell hybrid DNA using human MOP7-specific oligonucleotides. This location was confirmed by fluorescence in situ hybridization (FISH) using the BAC harboring human MOP7 structural gene as the probe (Genome Systems, Inc.).

Northern Blot analysis. To generate a hybridization probe for northern blot analysis, the 894 bp MOP7 insert from PL1017 was excised with EcoR1 and radiolabeled with [$\alpha$-$^{32}$P]dCTP by random priming. A northern blot containing poly A$^+$ mRNA from different mouse tissues (origene Technologies, Rockville, Md.) was hybridized with $5\times10^6$ cpm/ml MOP7 probe. β-actin was used as a loading control.

Gel-shift assay. To generate a double strand oligonucleotide probe containing the core HRE element, 50 ng of oligonucleotide OL414 was end-labeled with [$\gamma$-$^{32}$P]ATP and was annealed with 10 fold excess of cold complementary oligonucleotide OL415. Unlabeled oligonucleotides containing either wild-type HRE sequence (TACGTG) or mutant HRE sequences, AACGTG (OL396/397) or GACGTG (OL398/399), were used in competition experiments to demonstrate specificity. For expression of the bHLH-PAS proteins, mMOP7 (PL1025) and hARNT (PL87) were synthesized in a reticulocyte lysate in the presence of [$^{35}$S]methionine. The amount of each protein synthesized was calculated by measuring radioactivity and estimated to be approximately 1 fmol in each 10 μl gel-shift reaction. Each gel-shift assay was performed with 100,000 cpm of oligonucleotide probe per 10 μl reaction. To confirm complex identity, 1 μl of anti-ARNT sera was used to supershift the DNA bound protein complex.

Cell culture and transfection. COS-1 cells were maintained in high glucose DMEM medium supplemented with 10% fetal calf serum, 100 units/ml penicillin and streptomycin. The HRE driven luciferase reporter (PL945) was made by annealing OL1174 and OL1175 and then cloning the fragment into pGL3-promoter vector (Promega, Madison, Wis.). For transient transfection experiments, mammalian expression plasmids expressing MOP7 or hARNT with the reporter using lipofectamine (GIBCO BRL Life Technologies). A β-galactosidase-expression plasmid was co-transfected to control for transfection efficiency. Cells were incubated for 20–24 hours with or without treatment of cobalt chloride or hypoxia (1% $O_2$) before being harvested. The luciferase and β-galactosidase activities were determined using the luciferase assay and the Galacto-Light protocols as previously described (see Example 2).

Results and Discussion

From a TBLASTN search of the dBEST database with the sequence corresponding to amino acid residues 54 to 125 of hHIF1α, we identified a mouse EST clone (AA028416) that appeared to be a novel bHLH-PAS protein. This protein is referred to herein as MOP7 and as HIF3α, to denote its relationship to other hypoxia-inducible factors. To obtain the complete ORF of this cDNA, a series of RACE reactions was performed using cDNA from mouse lung as template. The MOP7 ORF (SEQ ID NO:7) spans 1.98 kb and encodes a 662-amino acid protein (SEQ ID NO:16) with a predicted molecular weight of 73 kDa. Northern blot analysis on mRNA prepared from selected mouse tissues identified a MOP7 transcript that is expressed in adult thymus, lung, brain, heart and kidney. This expression pattern is distinct from that reported for other α-class HIFs. HIF1α is most abundantly expressed in kidney and heart, and HIF2α is most abundantly expressed in vascular endothelial cells and is highest in lung, placenta and heart.

HIF1α (MOP1) is the most well-characterized α-class subunit. This protein can be described by a number of signature motifs. In addition to the bHLH-PAS domains, HIF1α also contains two HRD motifs in its C-terminus that confer hypoxia responsiveness. The HRD1 appears to primarily confer hypoxia-dependent protein stability, whereas HRD2 appears to confer hypoxia-responsive transcriptional activity. To determine if similar motifs occur in MOP7, we compared HIF1α. HIF2α and MOP7 protein sequences using the CLUSTAL algorithm (Higgins & Sharp, Gene 73: 237–244, 1988. These three sequences shared greater than 92% identity in the basic region, 68% in the HLH domain, and greater than 53% in the PAS domain. Although little sequence with significant homology to HRD2 was found, a 36-amino acid stretch within the C-terminal half of MOP7 was found to share 61% identity with the HRD1 of HIF1α.

Figure 8:
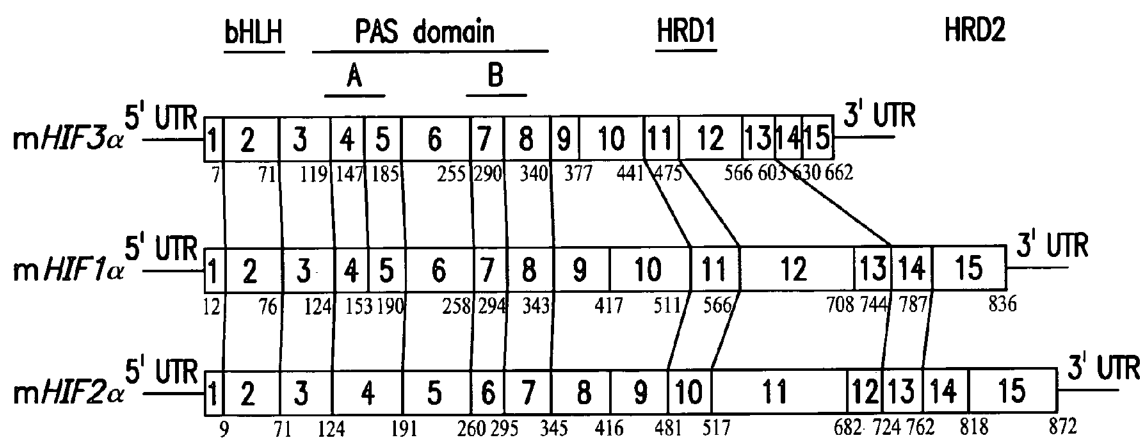
FIG. 8. The splicing site within mouse MOP7 ORF are compared with those previously reported for mHIF1α and hHIF2α. The numbers of amino acids at which the splicing occurs are marked underneath the sequence. The conserved splicing sites are defined as the splicing sites of HIF1α and HIF2α that are within one amino acid of the corresponding MOP7 splicing site on the aligned sequence map using CLUSTAL method. These sites are marked with lines between different ORFs (see GenBank Accession Numbers AF079140-079153 for detailed sequences of mMOP7 splice sites.

To further demonstrate the evolutionary relationship between these α-class HIFS, we compared their gene structure and chromosomal localization. Direct sequencing of a BAC clone containing the mMOP7 gene revealed 15 exons, all with consensus splice donor/acceptor sites (see sequences of Genbank Accession No. AF079140-079153 for exon-intron junctions). We found that 11 of 15 and 10 of 15 splice junctions found in the mMOP7 gene are conserved to those found in hte structural genes of mHIF1α and hHIF2α, respectively (FIG. 8). To characterize the distribution of HIF genes in the mammalian genome, we used human MOP7-specific PCR reactions against a human/hamster somatic cell panel and mapped the MOP7 gene locus on human chromosome 19. This locus was further defined to chromosome 19q13.13–13.2 by FISH using a BAC clone containing the human MOP7 structural gene as a probe. Therefore, the human MOP7 locus is distinct from that of human HIF1α and HIF2α, which reside on chromosome 14q21–24 and 2p16–21, respectively.

As a biochemical proof that MOP7 was a bona fide α-class HIF, we performed gel-shift and transient transfection analyses. Because HIF1α and HIF2α are known to pair with the β-class HIF subunit ARNT, we predicted that MOP7 would also pair with ARNT. Based upon sequence identity in their basic regions, we also predicted that a MOP7-ARNT would bind the HRE core sequence, TACGTG. As predicted, the gel-shift analysis showed that MOP7 only bound to the HRE containing oligonucleotide in the presence of ARNT. The specificity of the interaction was demonstrated by two additional observations. First, the MOP7-ARNT-HRE complex was abolished by anti-ARNT IgGs but not by preimmune antibodies. Second, the complex was blocked by an excess of HRE containing oligonucleotide but not by oligonucleotides with a single mutation within the core HRE sequence. To determine if this interaction could also occur in vivo, MOP7 and/or ARNT were cotransfected into COS-1 cells with a luciferase reporter driven by six HRE enhancer elements. The results demonstrated that the combination of MOP7 and ARNT upregulated transcription from the HRE-driven reporter by 11.7 fold, whereas neither protein alone had an effect. In addition, the activity of these complexes was enhanced by either hypoxia or cobalt chloride.

To demonstrate that the MOP7 activity was directly upregulated by hypoxia, we employed a fusion protein approach that has been used to map the HRDs of HIF1α. HRD1 of HIF1α has been shown to encode a hypoxia-responsive protein stability domain that also displays weak transcriptional activity. Given the sequence similarity between residues 453–496 if MOP7 and the HRD1 of HIF1α, we predicted that this domain would independently respond to hypoxic stimulus or cobalt ion exposure. To test this, we constructed a plasmid expressing a fusion protein comprised of the DNA binding domain of GAL4, the predicted HRD1 of MOP7, and the TAD from ARNT. We predicted that we could measure the response of this domain by monitoring the output from a GAL4-driven luciferase reporter in Hep3B cells. The results demonstrated that the fusion protein's activity increased by 4.5- and 4.2-fold, upon treatment with cobalt chloride or hypoxia, respectively. In control experiments, we observed that a GAL4 fusion protein harboring only the ARNT-TAD did not respond to either hypoxia or cobalt chloride treatment. The level of inducibility seen with the HRD1 fusion is consistent with that obtained for a similar fusion protein using the HRD1 domain of HIF1α. This result provided evidence that amino acids 453 to 496 of MOP7 was sufficient to confer the hypoxia inducibility and that the stability of the parent protein is regulated in a manner that is similar to that of HIF1α and HIF2α.

In eucaryotes, transcriptional responses to low oxygen tension are mediated by complex interactions between a number of α- and β-class HIF subunits. The characterization of a third α-class HIF with a tissue distribution that is distinct from either HIF1α or HIF2α provides evidence that cellular responses to hypoxia result from a complex set of interactions from multiple combinations of αβ pairs. MOP7 also may have a distinct role in mediating biological responses to hypoxia. In support of this notion, MOP7 and HIF1α have limited sequence homology in their C-termini. Most importantly, MOP7 contains sequence that corresponds to HIF1α's protein stability element, HRD1, but not to its hypoxia-responsive TAD element, HRD2. This may indicate that MOP7-ARNT complexes have decreased transcriptional potency relative to other HIF heterodimers. The importance of this complexity is underscored by the presence of HIF1α, HIF2α and MOP7 in both mice and humans. Finally, this complexity appears to be highly conserved among vertebrates. In support of this idea, we have cloned a partial human MOP7 cDNA and have shown all three HIF α-class genes reside on separate human chromosomes and display considerable sequence divergence in their C-termini.

The present invention is not limited to the embodiments described and exemplified above, but is capable of variation and modification within the scope of the appended claims.

We claim:

1. An isolated nucleic acid molecule having a sequence selected from the group consisting of:

a) SEQ ID NO:3;

b) a sequence encoding a polypeptide having amino acid SEQ ID NO:12.

2. A recombinant DNA molecule comprising the nucleic acid molecule of claim 1, operably linked to a vector for transforming cells.

3. A cell transformed with the recombinant DNA molecule of claim 2.

4. An oligonucleotide between about 10 and about 100 nucleotides in length, which is fully complementary to a portion of the nucleic acid molecule of claim 1.

5. The oligonucleotide of claim 4, wherein said portion includes a translation initiation site of said polypeptide.

6. An isolated nucleic acid molecule having a sequence selected from the group consisting of:

a) SEQ ID NO:9; and b) a sequence encoding a polypeptide having amino acid SEQ ID NO:17.

7. A recombinant DNA molecule comprising the nucleic acid molecule of claim 6, operably linked to a vector for transforming cells.

8. A cell transformed with the recombinant DNA molecule of claim 7.

9. An oligonucleotide between about 10 and about 100 nucleotides in length, which is fully complementary to a portion of the nucleic acid molecule of claim 6.

10. The oligonucleotide of claim 9, wherein said portion includes a translation initiation site of said polypeptide.

* * * * *

SEQUENCE LISTING

```
<160> NUMBER OF SEQ ID NOS: 126

<210> SEQ ID NO 1
<211> LENGTH: 3933
<212> TYPE: DNA
<213> ORGANISM: Homo sapiens

<400> SEQUENCE: 1

cacgaggcag cactctcttc gtcgcttcgg ccagtgtgtc gggctgggcc ctgacaagcc      60

acctgaggag aggctcggag ccgggcccgg accccggcga ttgccgcccg cttctctcta     120

gtctcacgag ggtttcccg cctcgcaccc ccacctctgg acttgccttt ccttctcttc     180

tccgcgtgtg gagggagcca gcgcttaggc cggagcgagc ctgggggccg cccgccgtga     240

agacatcgcg gggaccgatt caccatggag ggcgccggcg gcgcgaacga caagaaaaag     300

ataagttctg aacgtcgaaa agaaaagtct cgagatgcag ccagatctcg gcgaagtaaa     360

gaatctgaag ttttttatga gcttgctcat cagttgccac ttccacataa tgtgagttcg     420

catcttgata aggcctctgt gatgaggctt accatcagct atttgcgtgt gaggaaactt     480

ctggatgctg gtgatttgga tattgaagat gacatgaaag cacagatgaa ttgcttttat     540

ttgaaagcct tggatggttt tgttatggtt ctcacagatg atggtgacat gatttacatt     600

tctgataatg tgaacaaata catgggatta actcagtttg aactaactgg acacagtgtg     660
```

```
tttgatttta ctcatccatg tgaccatgag gaaatgagag aaatgcttac acacagaaat    720
ggccttgtga aaaagggtaa agaacaaaac acacagcgaa gctttttct cagaatgaag     780
tgtaccctaa ctagccgagg aagaactatg aacataaagt ctgcaacatg gaaggtattg    840
cactgcacag gccacattca cgtatatgat accaacagta accaacctca gtgtgggtat    900
aagaaaccac ctatgacctg cttggtgctg atttgtgaac ccattcctca cccatcaaat    960
attgaaattc ctttagatag caagactttc ctcagtcgac acagcctgga tatgaaattt   1020
tcttattgtg atgaaagaat taccgaattg atgggatatg agccagaaga acttttaggc   1080
cgctcaattt atgaatatta tcatgctttg gactctgatc atctgaccaa aactcatcat   1140
gatatgttta ctaaaggaca agtcaccaca ggacagtaca ggatgcttgc caaaagaggt   1200
ggatatgtct gggttgaaac tcaagcaact gtcatatata acaccaagaa ttctcaacca   1260
cagtgcattg tatgtgtgaa ttacgttgtg agtggtatta ttcagcacga cttgattttc   1320
tcccttcaac aaacagaatg tgtccttaaa ccggttgaat cttcagatat gaaaatgact   1380
cagctattca ccaaagttga atcagaagat acaagtagcc tctttgacaa acttaagaag   1440
gaacctgatg ctttaacttt gctggcccca gccgctggag acacaatcat atctttagat   1500
tttggcagca acgacacaga aactgatgac cagcaacttg aggaagtacc attatataat   1560
gatgtaatgc tcccctcacc caacgaaaaa ttacagaata taaatttggc aatgtctcca   1620
ttacccaccg ctgaaacgcc aaagccactt cgaagtagtg ctgaccctgc actcaatcaa   1680
gaagttgcat taaaattaga accaaatcca gagtcactgg aactttcttt taccatgccc   1740
cagattcagg atcagacacc tagtccttcc gatggaagca ctagacaaag ttcacctgag   1800
cctaatagtc ccagtgaata ttgtttttat gtggatagtg atatggtcaa tgaattcaag   1860
ttggaattgg tagaaaaact tttgctgaa gacacagaag caaagaaccc attttctact    1920
caggacacag atttagactt ggagatgtta gctccctata tcccaatgga tgatgacttc   1980
cagttacgtt ccttcgatca gttgtcacca ttagaaagca gttccgcaag ccctgaaagc   2040
gcaagtcctc aaagcacagt tacagtattc cagcagactc aaatacaaga acctactgct   2100
aatgccacca ctaccactgc caccactgat gaattaaaaa cagtgacaaa agaccgtatg   2160
gaagacatta aaatattgat tgcatctcca tctcctaccc acatacataa agaaactact   2220
agtgccacat catcaccata tagagatact caaagtcgga cagcctcacc aaacagagca   2280
ggaaaaggag tcatagaaca gacagaaaaa tctcatccaa gaagccctaa cgtgttatct   2340
gtcgctttga gtcaaagaac tacagttcct gaggaagaac taaatccaaa gatactagct   2400
ttgcagaatg ctcagagaaa gcgaaaaatg gaacatgatg gttcactttt tcaagcagta   2460
ggaattggaa cattattaca gcagccagac gatcatgcag ctactacatc actttcttgg   2520
aaacgtgtaa aaggatgcaa atctagtgaa cagaatggaa tggagcaaaa gacaattatt   2580
ttaataccct ctgatttagc atgtagactg ctggggcaat caatggatga aagtggatta   2640
ccacagctga ccagttatga ttgtgaagtt aatgctccta tacaaggcag cagaaaccta   2700
ctgcagggtg aagaattact cagagctttg gatcaagtta actgagcttt ttcttaattt   2760
cattcctttt tttggacact ggtggctcac tacctaaagc agtctattta tattttctac   2820
atctaatttt agaagcctgg ctacaatact gcacaaactt ggttagttca atttttgatc   2880
ccctttctac ttaatttaca ttaatgctct tttttagtat gttctttaat gctggatcac   2940
agacagctca ttttctcagt tttttggtat ttaaaccatt gcattgcagt agcatcattt   3000
```

-continued

```
taaaaaatgc acctttttat ttatttattt ttggctaggg agtttatccc tttttcgaat   3060

tatttttaag aagatgccaa tataattttt gtaagaaggc agtaaccttt catcatgatc   3120

ataggcagtt gaaaaatttt tacacctttt ttttcacatt ttacataaat aataatgctt   3180

tgccagcagt acgtggtagc cacaattgca caatatattt tcttaaaaaa taccagcagt   3240

tactcatgga atatattctg cgtttataaa actagttttt aagaagaaat tttttttggc   3300

ctatgaaatt gttaaacctg gaacatgaca ttgttaatca tataataatg attcttaaat   3360

gctgtatggt ttattattta aatgggtaaa gccatttaca taatatagaa agatatgcat   3420

atatctagaa ggtatgtggc atttatttgg ataaaattct caattcagag aaatcatctg   3480

atgtttctat agtcactttg ccagctcaaa agaaaacaat accctatgta gttgtggaag   3540

tttatgctaa tattgtgtaa ctgatattaa acctaaatgt tctgcctacc ctgttggtat   3600

aaagatattt tgagcagact gtaaacaaga aaaaaaaaat catgcattct tagcaaaatt   3660

gcctagtatg ttaatttgct caaaatacaa tgtttgattt tatgcacttt gtcgctatta   3720

acatcctttt tttcatgtag atttcaataa ttgagtaatt ttagaagcat tattttagga   3780

atatatagtt gtcacagtaa atatcttgtt ttttctatgt acattgtaca aatttttcat   3840

tccttttgct ctttgtggtt ggatctaaca ctaactgtat tgttttgtta catcaaataa   3900

acatcttctg tggaaaaaaa aaaaaaaaaa aaa                                 3933
```

<210> SEQ ID NO 2
<211> LENGTH: 2730
<212> TYPE: DNA
<213> ORGANISM: Homo sapiens

<400> SEQUENCE: 2

```
gcgtctgaac gtctcaaagg gccacagcga caatgacagc tgacaaggag aagaaaagga     60

gtagctcgga gaggaggaag gagaagtccc gggatgctgc gcggtgccgg cggagcaagg    120

agacggaggt gttctatgag ctggcccatg agctgcctct gccccacagt gtgagctccc    180

atctggacaa ggcctccatc atgcgactgg caatcagctt cctgcgaaca cacaagctcc    240

tctcctcagt ttgctctgaa aacgagtccg aagccgaagc tgaccagcag atggacaact    300

tgtacctgaa agccttggag ggtttcattg ccgtggtgac ccaagatggc gacatgatct    360

ttctgtcaga aaacatcagc aagttcatgg gacttacaca ggtggagcta acaggacata    420

gtatctttga cttcactcat ccctgcgacc atgaggagat tcgtgagaac ctgagtctca    480

aaaatggctc tggttttggg aaaaaaagca aagacatgtc cacagagcgg gacttcttca    540

tgaggatgaa gtgcacggtc accaacagag gccgtactgt caacctcaag tcagccacct    600

ggaaggtctt gcactgcacg ggccaggtga aagtctacaa caactgccct cctcacaata    660

gtctgtgtgg ctacaaggag cccctgctgt cctgcctcat catcatgtgt gaaccaatcc    720

agcacccatc ccacatggac atccccctgg atagcaagac cttcctgagc cgccacagca    780

tggacatgaa gttcacctac tgtgatgaca gaatcacaga actgattggt taccaccctg    840

aggagctgct tggccgctca gcctatgaat tctaccatgc gctagactcc gagaacatga    900

ccaagagtca ccagaacttg tgcaccaagg gtcaggtagt aagtggccag taccggatgc    960

tcgcaaagca tgggggctac gtgtggctgg agacccaggg gacggtcatc tacaaccctc   1020

gcaacctgca gccccagtgc atcatgtgtg tcaactacgt cctgagtgag attgagaaga   1080

atgacgtggt gttctccatg gaccagactg aatccctgtt caagccccac ctgatggcca   1140

tgaacagcat ctttgatagc agtggcaagg gggctgtgtc tgagaagagt aacttcctat   1200
```

-continued

```
tcaccaagct aaaggaggag cccgaggagc tggcccagct ggctcccacc ccaggagacg   1260
ccatcatctc tctggatttc gggaatcaga acttcgagga gtcctcagcc tatggcaagg   1320
ccatcctgcc cccgagccag ccatgggcca cggagttgag gagccacagc acccagagcg   1380
aggctgggag cctgcctgcc ttcaccgtgc cccaggcagc tgccccgggc agcaccaccc   1440
ccagtgccac cagcagcagc agcagctgct ccacgcccaa tagccctgaa gactattaca   1500
catctttgga taacgacctg aagattgaag tgattgagaa gctcttcgcc atggacacag   1560
aggccaagga ccaatgcagt acccagacgg atttcaatga gctggacttg gagacactgg   1620
caccctatat ccccatggac ggggaaggct tccagctaag ccccatctgc cccgaggagc   1680
ggctcttggc ggagaaccca cagtccaccc cccagcactg cttcagtgcc atgacaaaca   1740
tcttccagcc actggcccct gtagccccgc acagtccctt cctcctggac aagtttcagc   1800
agcagctgga gagcaagaag acagagcccg agcgccggcc catgtcctcc atcttctttg   1860
atgccggaag caaagcatcc ctgccaccgt gctgtggcca ggccagcacc cctctctctt   1920
ccatgggggg cagatccaac acccagtggc ccccagatcc accattacat tttgggccca   1980
caaagtgggc cgtcggggat cagcgcacag agttcttggg agcagcgccg ttggggcccc   2040
ctgtctctcc accccatgtc tccaccttca aaacaaggtc tgcaaagggt tttggggctc   2100
gaggcccaaa cgtgctgagt ccggccatgg tagccctctc caacaagctg aagctgaagc   2160
gacagctgga gtatgaaaag caagccttcc aggacccgag cggggggggac ccacctggtg   2220
gcagcacctc acatttgatg tggaaacgga tgaagaacct caggggtggg agctgccctt   2280
tgatgccgga caagccactg agcgcaaatg tacccaatga taagctcacc caaaactcca   2340
tgaggggcct gggccatccc ctgagacatc tgccgctgcc acagcctcca tctgccatca   2400
gtcccgggga gaacagcaag agcaggttcc ccccacagtg ctacgccacc cagtaccagg   2460
actacagcct gtcgtcagcc cacaaggtgt caggcatggc aagccggctg ctcgggccct   2520
catttgagtc ctacctgctg cccgaactga ccagatatga ccgtgaggtg aaagtgcccg   2580
tgctgggaag ctccacgctc ctgcaaggag gggacctcct cagagccctg gaccaggcca   2640
cctgagccag gcttctacct gggcagcacc tctgccgacg ccgtcccacc agcttcactc   2700
tctccgtctg tctttgcaac taggtatttg                                    2730
```

```
<210> SEQ ID NO 3
<211> LENGTH: 2430
<212> TYPE: DNA
<213> ORGANISM: Homo sapiens
<220> FEATURE:
<221> NAME/KEY: misc_feature
<222> LOCATION: (1883)..(1883)
<223> OTHER INFORMATION: nucleotide is a, c, t or g
<220> FEATURE:
<221> NAME/KEY: misc_feature
<222> LOCATION: (2413)..(2413)
<223> OTHER INFORMATION: nucleotide is a, c, t or g

<400> SEQUENCE: 3

ggagatgagc aaggaggccg tgagcctgtg ggcgctcact gtgtccctcc aacccccagt     60
ccccttgtgt gtctgcagag agatgacagg atcaggcaga agaaaacagc aatgtgtaac    120
tttgccattc atctccagag aattatgttt ttatcttttg ctttttcctc cccccaggtt    180
agaatataca gaacaccaag gagggataaa aaatgcaagg gaagctcaca gtcagattga    240
aaagcggcgt cgggataaaa tgaacagttt tatagatgaa ttggcttctt tggtaccaac    300
```

-continued

```
atgcaacgca atgtccagga aattagataa acttactgtg ctaaggatgg ctgttcagca    360
catgaaaaca ttaagaggtg ccaccaatcc atacacagaa gcaaactaca aaccaacttt    420
tctatcagac gatgaattga aacacctcat tctcagggca gcagatggat tttgtttgt     480
cgtaggatgt gaccgaggga agatactctt tgtctcagag tctgtcttca agatcctcaa    540
ctacagccag aatgatctga ttggtcagag tttgtttgac tacctgcatc ctaaagatat    600
tgccaaagtc aaggagcagc tctcctcctc tgacaccgca ccccgggagc ggctcataga    660
tgcaaaaact ggacttccag ttaaaacaga tataacccct gggccatctc gattatgttc    720
tggagcacga cgttctttct tctgtaggat gaagtgtaac aggccttcag taaaggttga    780
agacaaggac ttcccctcta cctgctcaaa gaaaaaagca gatcgaaaaa gcttctgcac    840
aatccacagc acaggctatt tgaaaagctg gccacccaca aagatggggc tggatgaaga    900
caacgaacca gacaatgagg ggtgtaacct cagctgcctc gtcgcaattg gacgactgca    960
ttctcatgta gttccacaac cagtgaacgg ggaaatcagg gtgaaatcta tggaatatgt   1020
ttctcggcac gcgatagatg gaaagtttgt ttttgtagac cagagggcaa cagctatttt   1080
ggcatattta ccacaagaac ttctaggcac atcgtgttat gaatattttc accaagatga   1140
cataggacat cttgcagaat gtcataggca agttttacag acgagagaaa aaattacaac   1200
taattgctat aaatttaaaa tcaaagatgg ttcttttatc acactacgga gtcgatggtt   1260
cagtttcatg aacccttgga ccaaggaagt agaatatatt gtctcaacta acactgttgt   1320
tttagccaac gtcctggaag gcggggaccc aaccttccca cagctcacag catcccccca   1380
cagcatggac agcatgctgc cctctggaga aggtggccca aagaggaccc accccactgt   1440
tccagggatt ccaggggga cccgggctgg ggcaggaaaa ataggccgaa tgattgctga    1500
ggaaatcatg gaaatccaca ggataagagg gtcattgcgt tctagctgtg gctccagccc   1560
attgaacatc acgagtacgc ctccccctga tgcctcttct ccaggaggca agaagatttt   1620
aaatggaggg actccagaca ttccttccag tggcctacta tcaggccagg ctcaggagaa   1680
cccaggttat ccatattctg atagttcttc tattcttggt gagaaccccc acataggtat   1740
agacatgatt gacaacgacc aaggatcaag tagtcccagt aatgatgagg cagcaatggc   1800
tgtcatcatg agcctcttgg aagcagatgc tggactgggt ggccctgttg actttagtga   1860
cttgccatgg ccgctgtaaa cantacatgt tgctttggca acagcctata gtatcaaagt   1920
gcattactgg tggagtttta cagtctgtga agcttactgg ataaggagag aatagctttt   1980
atgtactgac ttcataaaag ccatctcaga gccattgata caagtcaatc ttactatatg   2040
taacttcaga caaagtggaa ctaagcctgc tccagtgttt cctcatcatt gattattggg   2100
ctagctgtgg atagcttgca ttaattgtat attttggatt ctgtttgtgt tgaatttttt   2160
aatcattgtg cacagaagca tcattggtag cttttatatg caaatggtca tttcagatgt   2220
atggtgtttt tacactacaa agaagtcccc catgtggata tttcttatac taattgtatc   2280
ataaagccgt ttattcttcc ttgtaagaat cctttactat aaatatgggt taaagtataa   2340
tgtactagac agttaaatat ttttaataaa tgtttccctt gttctataaa aaaaaaaaaa   2400
aaaaaaaaaa aanattcgtg cggccgctag                                     2430
```

<210> SEQ ID NO 4
<211> LENGTH: 1912
<212> TYPE: DNA
<213> ORGANISM: Homo sapiens

<400> SEQUENCE: 4

```
gaattccggg ccggaaaaac tgcatagaaa atttaatgga tgaagatgag aaagacagag     60
ccaagagagc ttctcgaaac aagtctgaga agaagcgtcg ggaccagttc aatgttctca    120
tcaaagagct cagttccatg ctccctggca acacgcggaa aatggacaaa accaccgtgt    180
tggaagaggt catcggattt ttgcagaaac acaatgaagt ctcagcgcaa acggaaatct    240
gtgacattca gcaagactgg aagccttcat tcctcagtaa tgaagaattc acccagctga    300
tgttggaggc attagatggc ttcattatcg cagtgacaac agacggcagc atcatctatg    360
tctctgacag tatcacgcct ctccttgggc atttaccgtc ggatgtcatg gatcagaatt    420
tgttaaattt cctcccagaa caagaacatt cagaagttta taaaatcctt tcttcccata    480
tgcttgtgac ggattccccc tccccagaat acttaaaatc tgacggcgat ttagagtttt    540
attgccatct tctcagaggc agcttgaacc caaaggaatt tccaacttat gaatacataa    600
aatttgtagg aaattttcgc tcttacaaca atgtgcctag cccctcctgt aatggttttg    660
acaacaccct ttcaagacct tgccgggtgc cactaggaaa ggaggtttgc ttcattgcca    720
ccgttcgtct ggcaacacca caattcttaa aggaaatgtg catagttgac gaacctttag    780
aggaattcac ttcaaggcat agcttggaat ggaaattttt atttctggat cacagagcac    840
ctccaatcat aggatacctg ccttttgaag tgctgggaac ctcaggctat gactactacc    900
acattgatga cctggagctc ctggccaggt gtcaccagca cctgatgcag tttggcaaag    960
ggaagtcgtg ttgctaccgg tttctgacca aaggtcagca gtggatctgg ctgcagactc   1020
actactacat cacctaccat cagtggaact ccaagcccga gttcatcgtg tgcacacact   1080
cggtggtcag ttacgcagat gtccgggtgg aaaggaggca ggagctggct ctggaagacc   1140
cgccatccga ggccctccac tcctcagcac taaaggacaa gggctcaagc ctggaacctc   1200
ggcagcactt taacgcactc gacgtgggtg cctcgggcct taataccagt cattcgccat   1260
cggcgtcctc aagaagttcc cacaaatcct cgcacacagc catgtcagaa cccacctcca   1320
ctcccaccaa gctgatggca gaggccagca ccccggcttt gccaagatca gccaccctgc   1380
cccaagagtt acctgtcccc gggctcagcc aggcagccac catgccggcc cctctgcctt   1440
ccccatcgtc ctgcgacctc acacagcagc tcctgcctca gaccgttctg cagagcacgc   1500
ccgctcccat ggcacagttt tcggcacagt tcagcatgtt ccagaccatc aaagaccagc   1560
tagagcagcg gacgcggatc ctgcaggcca atatccggtg gcaacaggaa gagctccaca   1620
agatccagga gcagctctgc ctggtccagg actccaacgt ccagatgttc ctgcagcagc   1680
cagctgtatc cctgagcttc agcagcaccc agcgacctga ggctcagcag cagctacagc   1740
aaaggtcagc tgcagtgact cagccccagc tcggggcggg cccccaactt ccagggcaga   1800
tctcctctgc ccaggtcaca agccagcacc tgctcagaga atcaagtgtg atatcaaccc   1860
agggtccaaa gccaatgaga agctcacagc taatgcagag cagcggccgc tc           1912
```

<210> SEQ ID NO 5
<211> LENGTH: 1581
<212> TYPE: DNA
<213> ORGANISM: Homo sapiens

<400> SEQUENCE: 5

```
gaattcccgg agaccagcgc tgcgggccgc ggcggctggg gcgaggccag ctggcggccc     60
cggctctcag cccccagagc agcacctggg aggtcacatc ttgcagtccc tggatggctt    120
tgtgttcgcc ttgaaccagg aaggaaaatt cctctacatc tcagagacag tctccatcta    180
```

-continued

```
tctgggtctc tcacaggtgg agatgacggg cagcagcgtc ttcgactaca ttcaccctgg    240

ggaccactca gaggtgctgg agcaactggg gctgcggacg ccgacgcccg gccccccaac    300

cccgccctcc gtctcctctt cctcctcctc ttcctcttcg cttgcagata cccccgagat    360

cgaggccagc ctcaccaagg tgccccccctc ctccctggtc caggagcgct ccttctttgt   420

ccgcatgaaa tccacgctca ccaagagggg gctgcacgtc aaggcctcag ggtacaaggt    480

catccacgtg actgggcgcc ttcgggccca cgccctgggc cttgtggccc tcgggcacac    540

gttgccccccg gcccccctgg ctgagctgcc actccatgga cacatgatcg tcttccgtct   600

cagcctgggt ctcaccatcc ttgcttgtga gagcagagtc agcgaccaca tggacctggg    660

gccctcagag ctggtgggcc gcagctgcta ccagtttgtc cacggacaag acgccacgag    720

gatccgccag agccacgtgg acttgctgga caagggtcag gtgatgactg gttactaccg    780

ttggctgcag cgtgccgggg gcttcgtgtg gctgcagtct gtggccacag tggctgggag    840

cgggaagagc cccggggagc accatgtgct ttgggtcagc cacgtgctca gccaagccga    900

gggtggccaa actcctttgg atgccttcca gcttccagcc agcgtggcct gtgaggaggc    960

atccagcccg gggccagagc ccacagagcc ggagcctccg acggaaggga agcaggctgc   1020

cccagcggag aacgaggccc cccagaccca gggcaaacgc atcaaagtgg agcccggccc   1080

gagggaaacc aaaggctccg aggacagtgg cgacgaggat ccctccagcc acccggccac   1140

accgaggccc gagttcacct ctgtcatccg ggcaggggtc ctgaagcagg atccggtgcg   1200

gccatggggc ctggcgcctc ccggggaccc cccgcccacc ctcctgcacg cgggcttcct   1260

gccgccggtg gtgcggggcc tgtgcacacc cggcaccatc cgctacggcc ccgcggagct   1320

gggcctggtg tacccgcacc tgcagaggct gggtccgggc cccgcgctcc cggaggcctt   1380

ttacccgccc ctgggcctgc cctacccggg gcccgcgggc accaggctgc cgcggaaggg   1440

ggactgagga ctggcagagc tgccggcgcc ggaccctgcg acaaccgggg tcccccagga   1500

cagtaggccc ggctctgccc gtagccctga gaattaaacg ccggctctcc ctgcaaaaaa   1560

aaaaaaaaaa aaatttcctg c                                             1581
```

<210> SEQ ID NO 6
<211> LENGTH: 2148
<212> TYPE: DNA
<213> ORGANISM: Homo sapiens

<400> SEQUENCE: 6

```
ccacgcgtcc gacgcccccc acccgggagg ggggagagag gcaaaaagta agagaggaaa     60

aaaaatagca ggaagatggc gcccaccaag cccagctttc agcaggatcc ttccaggcga    120

gaacgtttac aagcattgag aaaggagaaa tcccgagatg ctgctcgctc ccgccgggga    180

aaagaaaact ttgagttcta tgaattggcc aagttgttgc ctcttcctgc agccattacc    240

agccagctcg acaaggcatc catcattcga cttacaatta gctatctgaa aatgagggac    300

tttgctaacc agggggaccc tccgtggaac ttgcgaatgg aaggccctcc acctaacaca    360

tcagtaaaag gtgcacagcg aaggagaagc cccagtgcac tagccattga agtatttgaa    420

gcacatttgg gaagccacat tttgcagtcc ctggatggct ttgtatttgc actaaatcag    480

gaaggaaaat ttttgtacat ttccgaaaca gtctccatct acctaggcct ctcacaagtg    540

gagctgacag gcagcagtgt ctttgactat gtccaccccg gagatcacgt ggagatggct    600

gagcagctgg gcatgaagct ccccccctggg cggggtctcc tgtcacaggg cactgctgag   660

gacggagcca gctcagcatc ttcctcctct cagtcggaga cccccgagcc agtggagtca    720
```

```
accagcccca gtctgctaac cactgacaac actcttgagc gttccttttt catccgaatg    780

aaatctactc tgaccaaacg cggtgtgcac atcaaatcat caggatataa ggtgattcac    840

ataacaggcc ggctacgcct gagagtgtcg ctgtcccacg ggaggaccgt ccccagccaa    900

atcatgggtc tcgtggttgt tgcgcatgcc ttgcctcccc ctacgatcaa tgaagtcaga    960

attgactgcc atatgttcgt cactcgagta aatatggacc tcaatatcat ttactgtgaa   1020

aataggatta gtgattatat ggatctgacc cctgtagata tcgtagggaa gagatgctac   1080

cacttcatcc atgctgaaga cgtggagggc atcaggcaca gtcacttgga cttgctgaat   1140

aagggtcagt gtgtgacaaa gtactatcgc tggatgcaga agaacggagg atatatttgg   1200

atacagtcca gtgccaccat agctattaat gccaagaatg caaatgaaaa gaatatcatc   1260

tgggtgaatt accttcttag caatcctgag tacaaggaca cacccatgga catcgcacag   1320

ctcccccatc tgccggagaa aacttccgaa tcctcggaga catccgactc tgagtcagac   1380

tctaaagaca cctcaggtat tacagaggac aacgagaact ccaagtccga cgagaagggg   1440

aaccagtccg agaacagcga agacccggag cccgaccgga agaagtcggg caacgcgtgt   1500

gacaacgaca tgaactgcaa cgacgacggc cacagctcca gtaacccgga cagccgcgac   1560

agcgacgaca gcttcgagca ctcggacttt gagaacccca aggcgggcga ggacggcttc   1620

ggtgctctgg gcgcgatgca gatcaaggtg gagcgctacg tggagagcga gtcggacctg   1680

cggctgcaga actgcgagtc actcacgtcc gacagcgcca aggactcgga cagcgcaggc   1740

gaggcgggcg cgcaggcctc cagcaagcac cagaagcgca agaaaaggcg gaaacggcaa   1800

aagggcggca gcgccagccg ccggcgcctg tccagcgcgt cgagcccagg cggcctggac   1860

gcgggcctgg tggagccccc gcggctgctg tcctccccca acagtgcctc ggtgctcaag   1920

atcaagacgg agatctcaga acccatcaat ttcgacaatg acagcagcat ctggaactac   1980

ccgcccaacc gggagatctc caggaacgag tccccctaca gcatgaccaa gccccccagc   2040

tctgagcact tcccgtcccc gcagggcggc ggcggtgggg gtggcggtgg cggggggctg   2100

cacgtggcca ttcccgactc ggtcctcacs ccgcccggcg ccgacggc                2148
```

<210> SEQ ID NO 7
<211> LENGTH: 2207
<212> TYPE: DNA
<213> ORGANISM: Mus musculus

<400> SEQUENCE: 7

```
agctaagtcc cggagaggac agagggcctt aggcacacaa cctaggggag aagcctggag     60

caaagcccca cagggagggc cacatggact gggaccaaga caggtcgaac accgagctgc    120

ggaaggagaa gtcgcgggac gcggcccgca gccggcgcag ccaggagacg gaggtgctgt    180

accagctggc gcacactctg ccctttgcgc gcggcgtcag cgcgcacctg gacaaggcct    240

ccatcatgcg cctcacaatc agctacctgc gcatgcaccg cctctgcgca gcaggggagt    300

ggaaccaggt ggaaaaaggg ggagagccac tggacgcctg ctacctgaag gccctggagg    360

gtttcgtcat ggtactcacc gccgagggag acatggctta cctgtcggaa aatgtcagca    420

agcacctggg cctcagtcag ctggagctca ttggacacag tatctttgat tttatccatc    480

cctgtgacca agaggaactt caagacgccc tgacccccag gccgaacctg tcaaagaaga    540

agctggaagc cccaacagag cgccactttt ccctgcgaat gaagagcacg ctcaccagca    600

gagggcgcac gctcaacctc aaagcggcca cctggaaggt gctgcactgc tcaggacata    660
```

-continued

```
tgagggccta caagcccccct gcacagactt cccctgccgg gagccctcgc tccgagcctc    720

ccctgcaatg cctggtgctt atctgtgaag ccatccccca cccagccagt ctggagcccc    780

cgctgggccg aggggccttt ctcagtcgcc acagcctgga catgaagttc acatactgcg    840

acgagaggat tgcagaagtt gctggctaca gtcctgatga cctgattggc tgttctgcct    900

atgaatacat ccacgctttg gactctgatg cggtcagcag gagcatccac actttgttga    960

gcaagggcca ggcagtaacg gggcagtatc gcttcctggc ccggactgga ggctatctgt   1020

ggactcagac tcaggctaca gtggtgtcag gggggcgggg cccccagtcg gaaagtatca   1080

tctgcgtcca cttcctgatc agccgtgtag aagagaccgg agtggtgctg tctctggaac   1140

aaacggagca acatactcgc agacccccctc ggctgagtgc ctcctcgcag aagggtatcc   1200

ctggcaacag tgtagactct cctgctccgc ggatcctggc cttcctgcac cctccggccc   1260

tgagtgaggc ctccctggct gctgaccctc gccgtttctg tagtccagac ctgcgccgcc   1320

tcatggcacc catcctggat ggacctcccc cagctgccac gcccagcacc cccacaagcta   1380

cacggagacc ccaaagtcct cttccggctg atctcccaga taagttggca gtgggcttgg   1440

aaaatgcgca cagactctcc actgcccaga aaaacaagac cgtggagaca gatctagata   1500

tagctcagga ctctgacact ctggacttgg agatgctggc cccctacatc tccatggatg   1560

atgacttcca gctcaactcc agtgagcaat tgcccaaagt ccaccgcaga cctcccaggg   1620

tggcccgcag gccccgtgct cggagcttcc atggcctgtc gcctcctatc cctgagccct   1680

ccctactgcc ccgctggggg agtgatccac gactgaactg ttccagtcct tccaggggcg   1740

atcgccccac agcctccctg atgcctggaa ctcggaagag ggccttggcc cagagctcag   1800

aggacaaagg gttggagctg ctggaaatta agcctcccaa gcggtcccca agactagaac   1860

ctggaagctt cctgctgcct ccgctcagcc tgagtttcct tctgcaaggt cgacaactcc   1920

tgggaaacca gcaggatccc agagcccccc tcgtgcattc tcatgagccc ttgggcctag   1980

ctccctcgct gctctctctc tgccagcatg aggaaactgt ccagcccagg aaccacttcc   2040

cgccagcagc aggcttgggc cagacccact gagtcagcct tcctctaagc cctcttcttc   2100

tatcccagaa aggactcagc cacactccac accagcagcc tacacccagg atggggcctc   2160

tctcctctga gtgtgccccc ccccagccag ccacagtcct acctcag                 2207
```

<210> SEQ ID NO 8
<211> LENGTH: 6218
<212> TYPE: DNA
<213> ORGANISM: Homo sapiens

<400> SEQUENCE: 8

```
gtggtcgagc cgcgcgcagg gtgcgctcgt ttgaactgcg gtgacaccga gggttgggga     60

ctcgaacccc cgcttcgcag ctcaggagcc tgaggtccga aagcttcgtt ccagagccca    120

gcatgaatgg atacgcggaa tttccgccca gccccagtaa ccccaccaag gagcccgtgg    180

agccccagcc cagccaggtc ccactgcagg aagatgtgga catgagcagt ggctccagtg    240

gacatgagac caacgaaaac tgctccacgg ggcgggactc gcagggcagt gactgtgacg    300

acagtgggaa ggagctgggg atgctggtgg agccaccgga tgcccgccag agtccagata    360

cctttagcct gatgatggca aaatctgaac acaacccatc tacaagtggc tgcagtagcg    420

accagtcttc gaaagtggac acacacaaag aactgataaa aacactaaag gagctgaagg    480

tccacctccc tgcagacaag aaggccaagg gcaaggccag tacgctggcc accttgaagt    540

acgccctcag gagcgtgaag caggtgaaag ccaatgaaga gtattaccag ctgctgatgt    600
```

-continued

```
ccagcgaggg tcacccctgt ggagcagacg tgccctccta caccgtggag gagatggaga    660
gcgttacctc tgagcacatt gtgaagaatg ccgatatgtt tgcggtggcc gtgtccctgg    720
tgtctgggaa gatcctgtac atctctgacc aggttgcatc catatttcac tgtaaaagag    780
atgccttcag cgatgccaag tttgtggagt tcctggcgcc tcacgatgtg ggcgtgttcc    840
acagtttcac ctccccgtac aagcttccct tgtggagcat gtgcagtgga gcagattctt    900
ttactcaaga atgcatggag gagaaatctt tcttttgccg tgtcagtgtc cggaaaagcc    960
acgagaatga aatccgctac cacccctcc gcatgacgcc ctacctggtc aaggtgcggg   1020
accaacaagg tgctgagagt cagctttgct gccttctgct ggcagagaga gtgcactctg   1080
gttatgaagc ccctagaatt cctcctgaaa agagaatttt tacaaccacc catacaccaa   1140
attgtttgtt ccaggatgtg gatgaaaggg cggtccctct cctgggctac ctacctcagg   1200
acctgattga aaccccagtg ctcgtgcagc tccaccctag tgacaggccc ttgatgctgg   1260
ccatccacaa aaagatcctg cagtcaggcg ggcagccttt cgactattct cccattcggt   1320
ttcgcgcccg gaacggagag tacatcacgt tggacaccag ctggtccagc ttcatcaacc   1380
catggagcag gaaaatctcc ttcatcattg ggaggcacaa agtcagggtg ggccctttga   1440
atgaggacgt gtttgcagcc cacccctgca cagaggagaa ggccctgcac cccagcattc   1500
aggagctcac agagcagatc caccggctcc tgctgcagcc cgtcccccac agcggctcca   1560
gtggctacgg gagtctgggc agcaacgggt cccacgagca ccttatgagc cagacctcct   1620
ccagcgacag caacggccat gaggactcac gccggaggag agccgaaatt tgtaaaaatg   1680
gtaacaagac caaaaataga agtcattatt ctcatgaatc tggagaacaa aagaaaaaat   1740
ccgttacaga aatgcaaact aatcccccag ctgagaagaa agctgtccct gccatggaaa   1800
aggacagcct gggggtcagc ttccccgagg agttggcctg caagaaccag cccacctgct   1860
cctaccagca gatcagctgc ttggacagcg tcatcaggta cttggagagc tgcaatgagg   1920
ctgccaccct gaagaggaaa tgcgagttcc cagcaaacgt cccagcgcta aggtccagtg   1980
ataagcggaa ggccacagtc agcccagggc cacacgctgg agaggcagag ccgccctcca   2040
gggtgaacag ccgcacggga gtaggtacgc acctgacctc gctggcactg ccgggcaagg   2100
cagagagtgt ggcgtcgctc accagccagt gcagctacag cagcaccatc gtccatgtgg   2160
gagacaagaa gccgcagccg gagttagaga tggtggaaga tgctgcgagt gggccagaat   2220
ccctggactg cctggcgggc cctgccctgg cctgtggtct cagccaagag aaggagccct   2280
tcaagaagct gggcctcacc aaggaggtac tcgctgcaca cacacagaag gaggagcaga   2340
gcttcctgca gaagttcaaa gaaataagaa aactcagcat tttccagtcc cactgccatt   2400
actacttgca agaaagatcc aaggggcagc caagtgaacg aactgcccct ggactaagaa   2460
atacttccgg aatagattca ccttggaaaa aaacaggaaa gaacagaaaa ttgaagtcca   2520
agcgggtcaa acctcgagac tcatctgaga gcaccggatc tgggggggccc gtgtccgccc  2580
ggcccccgct ggtgggcttg aacgccacag cctggtcacc ctcagacacg tcccagtcca   2640
gctgcccagc cgtgcccttt cccgccccag tgccagcagc ttattcactg cccgtgtttc   2700
cagcgccagg gactgtggca gcacccccgg cacctcccca cgccagcttc acagtgcctg   2760
ctgtgcccgt ggacctccag caccagtttg cagtccagcc cccacctttc cctgcccctt   2820
tggcgcctgt catggcattc atgctaccca gttattcctt cccctcgggg accccaaacc   2880
tgccccaggc cttcttcccc agccagcctc agtttccgag ccaccccaca ctcacatccg   2940
```

-continued

```
agatggcctc tgcctcacag cctgagttcc ccagccggac ctcgatcccc agacagccat   3000
gtgcttgtcc agccacccgg gccaccccac catcggccat gggtagggcc tccccaccgc   3060
tctttcagtc ccgcagcagc tcgcccctgc agctcaacct gctgcagctg gaggaagccc   3120
ctgagggtgg cactggagcc atggggacca caggggccac agagacagca gctgtagggg   3180
cggactgcaa acctggcact tctcgggacc agcagccgaa ggcgcctctg acccgtgatg   3240
aaccctcaga cacacagaac agtgacgccc tttccacgtc aagcggcctc ctaaacctcc   3300
tgctgaatga ggacctctgc tcagcctcgg gctctgctgc ttcggagtct ctgggctccg   3360
gctcactggg ctgcgacgcc tccccgagtg ggcaggcag tagtgacaca agtcatacca   3420
gcaaatattt tggaagcatt gactcctcag agaataatca caaagcaaaa atgaacactg   3480
gtatggaaga aagtgagcat ttcattaagt gcgtcctgca ggatcccatc tggctgctga   3540
tggcagatgc ggacagcagc gtcatgatga cgtaccagct gccttcccga aatttagaag   3600
cggttttgaa ggaggacaga gagaagctga agctcctaca gaaactccag ccaggttcac   3660
ggagagtcag aagcaggagc tgcgcgaggt ccaccagtgg atgcagacgg gcggcctgcc   3720
cgcagccatc gacgtggcag aatgtgttta ctgtgaaaac aaggaaaaag gtaatatttg   3780
cataccatat gaggaagata ttccttctct gggactcagc gaagtgtcgg acaccaaaga   3840
agacgaaaat ggatccccct tgaatcacag gatcgaagag cagacgtaac ccctgcccca   3900
cctcagcccg gcagccagcg aggtacacca ggtggtgctt ggaagagatg aaagatcttc   3960
atggctgttt ccactgaaat ggacacatat gctcatgttg cttttttgt tttagaaaaa   4020
aaaacaacat agttttctga aggggcgact taaaactgtg gagagtgggg agagttcgga   4080
aagaaatatg tttttatata taaaatatat atgtggagtt ttgtgggatg gggaagagat   4140
tttagttgtt atttaacttg agaaagacta agcgcctctt agtgtcaggg aagttgcctc   4200
agtgctccca gaagtcctgt gactgtgacg agacctctgt ctgctgcacc agctggggac   4260
tctggcttcc agagctttcc cagggtgttt ggatcagatc aaattttgtc ctctcttggg   4320
gactgctttt tatctgaatt atcatttagt caaggtagag tgttttttta tacataccaa   4380
atggagatag cagcctctcc tagttttatt tcaaaacgtt tcacattaaa tggtgtgaag   4440
cgttgtttgg caaaccaaca gctttggctt ctggtgtggt caatatttca gtctgacata   4500
ggttttgttt gtagtgaaca aagttgaaac atttgctctg gactaaagaa gcctagtggt   4560
ttgtgtggcc aactccatcg gatgaatgca cacgcagaca gaccctctgt atatttctgc   4620
attattcttg tctccttttc agaccatgat ggccaatatg gagattaaaa tatgtcatca   4680
gtcatctctt tatggtgact tccctttgca aaccaggctg tgaccaacac atgtgagacc   4740
cagtcctgtt tggttttctt ccgttggaac cacccagaca tctgcttcca cccagccaag   4800
cccacatcac atctcctggc cgagagcagc cactgccact cagtctgaca gcttgcgact   4860
gcatctgtat tttcaggggt gcagtgagct cacctctccc actgcaccct gggttgggtg   4920
cacagccctc attcttttca tgagcccgac ctctctcgga gcagcttcag gcctctgcca   4980
gtgtccccag cacttttagg tcatttggac acttggggaa aagtgaggcc agtctgcccg   5040
gctttttaca aaacctcatg ttgcattgta tattccaaag atggttcaga aaatttaata   5100
ttggtccctg gtggaaattc aaagttatca ctgaagaaca gttgacttaa aattggacca   5160
agactatgag gcttaaaagg gaccagggtt ttcttttttt tttttttttt tttttttttt   5220
agatggagtt tctttttgcc caggctggag tgcagtggcg ccatcttggc tcactgcaac   5280
ctctgcctcc caggttcaag cgattctcct gcctcagcct cctgagtagc tgggaccaca   5340
```

-continued

```
ggcgactgcc accacaccca gctaattttt tgtattttta gtagagacag ggtttcacca   5400
tgttggccag gctggtctcg aactcctgac ctcaagcgat ccacccacct cggcctccca   5460
aagtgctggg attacaggcg tgagccacca cgcccaactg ggaccagggt tttctgtttt   5520
ttgatggagg tgaaatctct ttgtaatcca ctaggttttc atcgtaaaac catcttatgc   5580
ctgactatta aacctattct tcataaacac aagaacactt taatttttcg ttaatttaca   5640
aagtaacatc agctgcctat gcctatgata aggtagcagt ctgcattctt atggccatta   5700
gatgttacaa actccttgcc tctaaagtca gatcatgaag ggataggtgt tcatctaagg   5760
ttacagttat gttaccgaaa cacaaaactg ccaaaatctt actctgctgt tatgaatgtt   5820
taccatcagc attattttat catttaatat gtgctcactg attgttaact gtagcttcag   5880
cgcgtgccaa gcagttgact taataggatc atcttgtgaa tttgtttacg tgatgccaag   5940
catcaagtca tgttttcttt agtgtgtgtg cttacacagg tgttaaacag tttttctcta   6000
ttttaaactg agccttcttt ttaatatatt cccgaagaga tatgtaaata agctctcaga   6060
gtttctgtga tgatttgttg agccttgctg gacaagtggt ttgtttgtgt gcaaaccaaa   6120
ctttctttac ccagtgcaat agatttgttt gactgcttgt gtctttttat gacctgtttg   6180
ccttttagaa aattggtaaa taaagcaagt atattttt                           6218
```

<210> SEQ ID NO 9
<211> LENGTH: 1815
<212> TYPE: DNA
<213> ORGANISM: Homo sapiens

<400> SEQUENCE: 9

```
ccgggcaggt ctcctgtggt ttccagccgc gtgagtccag ggacaagacc aacagctatg     60
gggtctttca gctcacacat gacagagttt ccacgaaaac gcaaaggaag tgattcagac    120
ccatcccagt caggaatcat gacagaaaaa gtggtggaaa agctttctca gaatcccctt    180
acctatcttc tttcaacaag gatagaaata tcagcctcca gtggcagcag agaagctcat    240
agccaaactg aaaagcggag gagagataaa atgaataacc tgattgaaga actgtctgca    300
atgatccctc agtgcaaccc catggcgcgt aaactggaca aacttacagt tttaagaatg    360
gctgttcaac acttgagatc tttaaaaggc ttgacaaatt cttatgtggg aagtaattat    420
agaccatcat ttcttcagga taatgagctc agacatttaa tccttaagac tgcagaaggc    480
ttcttatttg tggttggatg tgaaagagga aaaattctct tcgtttctaa gtcagtctcc    540
aaaatactta attatgatca ggctagtttg actggacaaa gcttatttga cttcttacat    600
ccaaaagatg ttgccaaagt aaaggaacaa ctttcttctt ttgatatttc accaagagaa    660
aagctaatag ataccaaaac tggtttgcaa gttcacagta atctccacgc tggaaggaca    720
cgtgtgtatt ttggctcaag acgatctttt ttctgtcgga taaagagttg taaaatctct    780
gtcaaagaag agcatggatg cttacccaac tcaaagaaga aagagcacag aaaattctat    840
actatccatt gcactggtta cttgagaagc tggcctccaa atattgttgg aatggaagaa    900
gaaaggaaca gtaagaaaga caacagtaat tttacctgcc ttgtggccat tggaagatta    960
cagccatata ttgttccaca gaacagtgga gagattaatg tgaaaccaac tgaatttata   1020
acccggtttg cagtgaatgg aaaatttgtc tatgtagatc aaagggcaac agcgatttta   1080
ggatatctgc ctcaggaact tttgggaact tcttgttatg aatattttca tcaagatgac   1140
cacaataatt tgactgacaa gcacaaagca gttctacaga gtaaggagaa aatacttaca   1200
```

-continued

```
gattcctaca aattcagagc aaaagatggc tcttttgtaa ctttaaaaag ccaatggttt   1260

agtttcacaa atccttggac aaaagaactg gaatatattg tatctgtcaa cactttagtt   1320

ttgggacata gtgagcctgg agaagcatca tttttacctt gtagctctca atcatcagaa   1380

gaatcctcta gacagtcctg tatgagtgta cctggaatgt ctactggaac agtacttggt   1440

gctggtagta ttggaacaga tattgcaaat gaaattctgg atttacagag gttacagtct   1500

tcttcatacc ttgatgattc gagtccaaca ggtttaatga aagatactca tactgtaaac   1560

tgcaggagta tgtcaaataa ggagttgttt ccaccaagtc cttctgaaat gggggagcta   1620

gaggctacca ggcaaaacca gagtactgtt gctgtccaca gccatgagcc actcctcagt   1680

gatggtgcac agttggattt cgatgcccta tgtgacaatg atgacacagc catggctgca   1740

tttatgaatt acttagaagc agagggggc ctgggagacc ctggggactt cagtgacatc   1800

cagtggaccc tctag                                                    1815
```

```
<210> SEQ ID NO 10
<211> LENGTH: 826
<212> TYPE: PRT
<213> ORGANISM: Homo sapiens

<400> SEQUENCE: 10

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
```

-continued

```
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
        675                 680                 685
```

```
Asn Val Leu Ser Val Ala Leu Ser Gln Arg Thr Thr Val Pro Glu Glu
    690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
        755                 760                 765

Lys Thr Ile Ile Leu Ile Pro Ser Asp Leu Ala Cys Arg Leu Leu Gly
    770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825


<210> SEQ ID NO 11
<211> LENGTH: 870
<212> TYPE: PRT
<213> ORGANISM: Homo sapiens

<400> SEQUENCE: 11

Met Thr Ala Asp Lys Glu Lys Lys Arg Ser Ser Ser Glu Arg Arg Lys
1               5                   10                  15

Glu Lys Ser Arg Asp Ala Ala Arg Cys Arg Arg Ser Lys Glu Thr Glu
            20                  25                  30

Val Phe Tyr Glu Leu Ala His Glu Leu Pro Leu Pro His Ser Val Ser
        35                  40                  45

Ser His Leu Asp Lys Ala Ser Ile Met Arg Leu Ala Ile Ser Phe Leu
    50                  55                  60

Arg Thr His Lys Leu Leu Ser Ser Val Cys Ser Glu Asn Glu Ser Glu
65                  70                  75                  80

Ala Glu Ala Asp Gln Gln Met Asp Asn Leu Tyr Leu Lys Ala Leu Glu
                85                  90                  95

Gly Phe Ile Ala Val Val Thr Gln Asp Gly Asp Met Ile Phe Leu Ser
            100                 105                 110

Glu Asn Ile Ser Lys Phe Met Gly Leu Thr Gln Val Glu Leu Thr Gly
        115                 120                 125

His Ser Ile Phe Asp Phe Thr His Pro Cys Asp His Glu Glu Ile Arg
    130                 135                 140

Glu Asn Leu Ser Leu Lys Asn Gly Ser Gly Phe Gly Lys Lys Ser Lys
145                 150                 155                 160

Asp Met Ser Thr Glu Arg Asp Phe Phe Met Arg Met Lys Cys Thr Val
                165                 170                 175

Thr Asn Arg Gly Arg Thr Val Asn Leu Lys Ser Ala Thr Trp Lys Val
            180                 185                 190

Leu His Cys Thr Gly Gln Val Lys Val Tyr Asn Asn Cys Pro Pro His
        195                 200                 205

Asn Ser Leu Cys Gly Tyr Lys Glu Pro Leu Leu Ser Cys Leu Ile Ile
    210                 215                 220

Met Cys Glu Pro Ile Gln His Pro Ser His Met Asp Ile Pro Leu Asp
```

-continued

```
225                 230                 235                 240

Ser Lys Thr Phe Leu Ser Arg His Ser Met Asp Met Lys Phe Thr Tyr
                245                 250                 255

Cys Asp Asp Arg Ile Thr Glu Leu Ile Gly Tyr His Pro Glu Glu Leu
            260                 265                 270

Leu Gly Arg Ser Ala Tyr Glu Phe Tyr His Ala Leu Asp Ser Glu Asn
        275                 280                 285

Met Thr Lys Ser His Gln Asn Leu Cys Thr Lys Gly Gln Val Val Ser
    290                 295                 300

Gly Gln Tyr Arg Met Leu Ala Lys His Gly Gly Tyr Val Trp Leu Glu
305                 310                 315                 320

Thr Gln Gly Thr Val Ile Tyr Asn Pro Arg Asn Leu Gln Pro Gln Cys
                325                 330                 335

Ile Met Cys Val Asn Tyr Val Leu Ser Glu Ile Glu Lys Asn Asp Val
            340                 345                 350

Val Phe Ser Met Asp Gln Thr Glu Ser Leu Phe Lys Pro His Leu Met
        355                 360                 365

Ala Met Asn Ser Ile Phe Asp Ser Ser Gly Lys Gly Ala Val Ser Glu
    370                 375                 380

Lys Ser Asn Phe Leu Phe Thr Lys Leu Lys Glu Glu Pro Glu Glu Leu
385                 390                 395                 400

Ala Gln Leu Ala Pro Thr Pro Gly Asp Ala Ile Ile Ser Leu Asp Phe
                405                 410                 415

Gly Asn Gln Asn Phe Glu Glu Ser Ser Ala Tyr Gly Lys Ala Ile Leu
            420                 425                 430

Pro Pro Ser Gln Pro Trp Ala Thr Glu Leu Arg Ser His Ser Thr Gln
        435                 440                 445

Ser Glu Ala Gly Ser Leu Pro Ala Phe Thr Val Pro Gln Ala Ala Ala
    450                 455                 460

Pro Gly Ser Thr Thr Pro Ser Ala Thr Ser Ser Ser Ser Ser Cys Ser
465                 470                 475                 480

Thr Pro Asn Ser Pro Glu Asp Tyr Tyr Thr Ser Leu Asp Asn Asp Leu
                485                 490                 495

Lys Ile Glu Val Ile Glu Lys Leu Phe Ala Met Asp Thr Glu Ala Lys
            500                 505                 510

Asp Gln Cys Ser Thr Gln Thr Asp Phe Asn Glu Leu Asp Leu Glu Thr
        515                 520                 525

Leu Ala Pro Tyr Ile Pro Met Asp Gly Glu Gly Phe Gln Leu Ser Pro
    530                 535                 540

Ile Cys Pro Glu Glu Arg Leu Leu Ala Glu Asn Pro Gln Ser Thr Pro
545                 550                 555                 560

Gln His Cys Phe Ser Ala Met Thr Asn Ile Phe Gln Pro Leu Ala Pro
                565                 570                 575

Val Ala Pro His Ser Pro Phe Leu Leu Asp Lys Phe Gln Gln Gln Leu
            580                 585                 590

Glu Ser Lys Lys Thr Glu Pro Glu Arg Arg Pro Met Ser Ser Ile Phe
        595                 600                 605

Phe Asp Ala Gly Ser Lys Ala Ser Leu Pro Pro Cys Cys Gly Gln Ala
    610                 615                 620

Ser Thr Pro Leu Ser Ser Met Gly Gly Arg Ser Asn Thr Gln Trp Pro
625                 630                 635                 640

Pro Asp Pro Pro Leu His Phe Gly Pro Thr Lys Trp Ala Val Gly Asp
                645                 650                 655
```

-continued

```
Gln Arg Thr Glu Phe Leu Gly Ala Ala Pro Leu Gly Pro Pro Val Ser
        660                 665                 670

Pro Pro His Val Ser Thr Phe Lys Thr Arg Ser Ala Lys Gly Phe Gly
        675                 680                 685

Ala Arg Gly Pro Asn Val Leu Ser Pro Ala Met Val Ala Leu Ser Asn
    690                 695                 700

Lys Leu Lys Leu Lys Arg Gln Leu Glu Tyr Glu Lys Gln Ala Phe Gln
705                 710                 715                 720

Asp Pro Ser Gly Gly Asp Pro Pro Gly Gly Ser Thr Ser His Leu Met
                725                 730                 735

Trp Lys Arg Met Lys Asn Leu Arg Gly Gly Ser Cys Pro Leu Met Pro
            740                 745                 750

Asp Lys Pro Leu Ser Ala Asn Val Pro Asn Asp Lys Leu Thr Gln Asn
        755                 760                 765

Ser Met Arg Gly Leu Gly His Pro Leu Arg His Leu Pro Leu Pro Gln
    770                 775                 780

Pro Pro Ser Ala Ile Ser Pro Gly Glu Asn Ser Lys Ser Arg Phe Pro
785                 790                 795                 800

Pro Gln Cys Tyr Ala Thr Gln Tyr Gln Asp Tyr Ser Leu Ser Ser Ala
                805                 810                 815

His Lys Val Ser Gly Met Ala Ser Arg Leu Leu Gly Pro Ser Phe Glu
            820                 825                 830

Ser Tyr Leu Leu Pro Glu Leu Thr Arg Tyr Asp Arg Glu Val Lys Val
        835                 840                 845

Pro Val Leu Gly Ser Ser Thr Leu Leu Gln Gly Gly Asp Leu Leu Arg
    850                 855                 860

Ala Leu Asp Gln Ala Thr
865                 870


<210> SEQ ID NO 12
<211> LENGTH: 624
<212> TYPE: PRT
<213> ORGANISM: Homo sapiens

<400> SEQUENCE: 12

Met Ser Lys Glu Ala Val Ser Leu Trp Ala Leu Thr Val Ser Leu Gln
1               5                   10                  15

Pro Pro Val Pro Leu Cys Val Cys Arg Glu Met Thr Gly Ser Gly Arg
            20                  25                  30

Arg Lys Gln Gln Cys Val Thr Leu Pro Phe Ile Ser Arg Glu Leu Cys
        35                  40                  45

Phe Tyr Leu Leu Leu Phe Pro Pro Pro Arg Leu Glu Tyr Thr Glu His
    50                  55                  60

Gln Gly Gly Ile Lys Asn Ala Arg Glu Ala His Ser Gln Ile Glu Lys
65                  70                  75                  80

Arg Arg Arg Asp Lys Met Asn Ser Phe Ile Asp Glu Leu Ala Ser Leu
                85                  90                  95

Val Pro Thr Cys Asn Ala Met Ser Arg Lys Leu Asp Lys Leu Thr Val
            100                 105                 110

Leu Arg Met Ala Val Gln His Met Lys Thr Leu Arg Gly Ala Thr Asn
        115                 120                 125

Pro Tyr Thr Glu Ala Asn Tyr Lys Pro Thr Phe Leu Ser Asp Asp Glu
    130                 135                 140

Leu Lys His Leu Ile Leu Arg Ala Ala Asp Gly Phe Leu Phe Val Val
```

-continued

```
145                 150                 155                 160

Gly Cys Asp Arg Gly Lys Ile Leu Phe Val Ser Glu Ser Val Phe Lys
                165                 170                 175

Ile Leu Asn Tyr Ser Gln Asn Asp Leu Ile Gly Gln Ser Leu Phe Asp
            180                 185                 190

Tyr Leu His Pro Lys Asp Ile Ala Lys Val Lys Glu Gln Leu Ser Ser
        195                 200                 205

Ser Asp Thr Ala Pro Arg Glu Arg Leu Ile Asp Ala Lys Thr Gly Leu
    210                 215                 220

Pro Val Lys Thr Asp Ile Thr Pro Gly Pro Ser Arg Leu Cys Ser Gly
225                 230                 235                 240

Ala Arg Arg Ser Phe Phe Cys Arg Met Lys Cys Asn Arg Pro Ser Val
                245                 250                 255

Lys Val Glu Asp Lys Asp Phe Pro Ser Thr Cys Ser Lys Lys Lys Ala
            260                 265                 270

Asp Arg Lys Ser Phe Cys Thr Ile His Ser Thr Gly Tyr Leu Lys Ser
        275                 280                 285

Trp Pro Pro Thr Lys Met Gly Leu Asp Glu Asp Asn Glu Pro Asp Asn
    290                 295                 300

Glu Gly Cys Asn Leu Ser Cys Leu Val Ala Ile Gly Arg Leu His Ser
305                 310                 315                 320

His Val Val Pro Gln Pro Val Asn Gly Glu Ile Arg Val Lys Ser Met
                325                 330                 335

Glu Tyr Val Ser Arg His Ala Ile Asp Gly Lys Phe Val Phe Val Asp
            340                 345                 350

Gln Arg Ala Thr Ala Ile Leu Ala Tyr Leu Pro Gln Glu Leu Leu Gly
        355                 360                 365

Thr Ser Cys Tyr Glu Tyr Phe His Gln Asp Asp Ile Gly His Leu Ala
    370                 375                 380

Glu Cys His Arg Gln Val Leu Gln Thr Arg Glu Lys Ile Thr Thr Asn
385                 390                 395                 400

Cys Tyr Lys Phe Lys Ile Lys Asp Gly Ser Phe Ile Thr Leu Arg Ser
                405                 410                 415

Arg Trp Phe Ser Phe Met Asn Pro Trp Thr Lys Glu Val Glu Tyr Ile
            420                 425                 430

Val Ser Thr Asn Thr Val Val Leu Ala Asn Val Leu Glu Gly Gly Asp
        435                 440                 445

Pro Thr Phe Pro Gln Leu Thr Ala Ser Pro His Ser Met Asp Ser Met
    450                 455                 460

Leu Pro Ser Gly Glu Gly Gly Pro Lys Arg Thr His Pro Thr Val Pro
465                 470                 475                 480

Gly Ile Pro Gly Gly Thr Arg Ala Gly Ala Gly Lys Ile Gly Arg Met
                485                 490                 495

Ile Ala Glu Glu Ile Met Glu Ile His Arg Ile Arg Gly Ser Leu Arg
            500                 505                 510

Ser Ser Cys Gly Ser Ser Pro Leu Asn Ile Thr Ser Thr Pro Pro Pro
        515                 520                 525

Asp Ala Ser Ser Pro Gly Gly Lys Lys Ile Leu Asn Gly Gly Thr Pro
    530                 535                 540

Asp Ile Pro Ser Ser Gly Leu Leu Ser Gly Gln Ala Gln Glu Asn Pro
545                 550                 555                 560

Gly Tyr Pro Tyr Ser Asp Ser Ser Ser Ile Leu Gly Glu Asn Pro His
                565                 570                 575
```

-continued

```
Ile Gly Ile Asp Met Ile Asp Asn Asp Gln Gly Ser Ser Ser Pro Ser
            580                 585                 590

Asn Asp Glu Ala Ala Met Ala Val Ile Met Ser Leu Leu Glu Ala Asp
        595                 600                 605

Ala Gly Leu Gly Gly Pro Val Asp Phe Ser Asp Leu Pro Trp Pro Leu
    610                 615                 620


<210> SEQ ID NO 13
<211> LENGTH: 626
<212> TYPE: PRT
<213> ORGANISM: Homo sapiens

<400> SEQUENCE: 13

Met Asp Glu Asp Glu Lys Asp Arg Ala Lys Arg Ala Ser Arg Asn Lys
1               5                   10                  15

Ser Glu Lys Lys Arg Arg Asp Gln Phe Asn Val Leu Ile Lys Glu Leu
            20                  25                  30

Ser Ser Met Leu Pro Gly Asn Thr Arg Lys Met Asp Lys Thr Thr Val
        35                  40                  45

Leu Glu Glu Val Ile Gly Phe Leu Gln Lys His Asn Glu Val Ser Ala
    50                  55                  60

Gln Thr Glu Ile Cys Asp Ile Gln Gln Asp Trp Lys Pro Ser Phe Leu
65                  70                  75                  80

Ser Asn Glu Glu Phe Thr Gln Leu Met Leu Glu Ala Leu Asp Gly Phe
                85                  90                  95

Ile Ile Ala Val Thr Thr Asp Gly Ser Ile Ile Tyr Val Ser Asp Ser
            100                 105                 110

Ile Thr Pro Leu Leu Gly His Leu Pro Ser Asp Val Met Asp Gln Asn
        115                 120                 125

Leu Leu Asn Phe Leu Pro Glu Gln Glu His Ser Glu Val Tyr Lys Ile
    130                 135                 140

Leu Ser Ser His Met Leu Val Thr Asp Ser Pro Ser Pro Glu Tyr Leu
145                 150                 155                 160

Lys Ser Asp Gly Asp Leu Glu Phe Tyr Cys His Leu Leu Arg Gly Ser
                165                 170                 175

Leu Asn Pro Lys Glu Phe Pro Thr Tyr Glu Tyr Ile Lys Phe Val Gly
            180                 185                 190

Asn Phe Arg Ser Tyr Asn Asn Val Pro Ser Pro Ser Cys Asn Gly Phe
        195                 200                 205

Asp Asn Thr Leu Ser Arg Pro Cys Arg Val Pro Leu Gly Lys Glu Val
    210                 215                 220

Cys Phe Ile Ala Thr Val Arg Leu Ala Thr Pro Gln Phe Leu Lys Glu
225                 230                 235                 240

Met Cys Ile Val Asp Glu Pro Leu Glu Glu Phe Thr Ser Arg His Ser
                245                 250                 255

Leu Glu Trp Lys Phe Leu Phe Leu Asp His Arg Ala Pro Pro Ile Ile
            260                 265                 270

Gly Tyr Leu Pro Phe Glu Val Leu Gly Thr Ser Gly Tyr Asp Tyr Tyr
        275                 280                 285

His Ile Asp Asp Leu Glu Leu Leu Ala Arg Cys His Gln His Leu Met
    290                 295                 300

Gln Phe Gly Lys Gly Lys Ser Cys Cys Tyr Arg Phe Leu Thr Lys Gly
305                 310                 315                 320

Gln Gln Trp Ile Trp Leu Gln Thr His Tyr Tyr Ile Thr Tyr His Gln
```

-continued

```
                325                 330                 335

Trp Asn Ser Lys Pro Glu Phe Ile Val Cys Thr His Ser Val Val Ser
            340                 345                 350

Tyr Ala Asp Val Arg Val Glu Arg Arg Gln Glu Leu Ala Leu Glu Asp
        355                 360                 365

Pro Pro Ser Glu Ala Leu His Ser Ser Ala Leu Lys Asp Lys Gly Ser
    370                 375                 380

Ser Leu Glu Pro Arg Gln His Phe Asn Ala Leu Asp Val Gly Ala Ser
385                 390                 395                 400

Gly Leu Asn Thr Ser His Ser Pro Ser Ala Ser Ser Arg Ser Ser His
                405                 410                 415

Lys Ser Ser His Thr Ala Met Ser Glu Pro Thr Ser Thr Pro Thr Lys
            420                 425                 430

Leu Met Ala Glu Ala Ser Thr Pro Ala Leu Pro Arg Ser Ala Thr Leu
        435                 440                 445

Pro Gln Glu Leu Pro Val Pro Gly Leu Ser Gln Ala Ala Thr Met Pro
    450                 455                 460

Ala Pro Leu Pro Ser Pro Ser Ser Cys Asp Leu Thr Gln Gln Leu Leu
465                 470                 475                 480

Pro Gln Thr Val Leu Gln Ser Thr Pro Ala Pro Met Ala Gln Phe Ser
                485                 490                 495

Ala Gln Phe Ser Met Phe Gln Thr Ile Lys Asp Gln Leu Glu Gln Arg
            500                 505                 510

Thr Arg Ile Leu Gln Ala Asn Ile Arg Trp Gln Gln Glu Glu Leu His
        515                 520                 525

Lys Ile Gln Glu Gln Leu Cys Leu Val Gln Asp Ser Asn Val Gln Met
    530                 535                 540

Phe Leu Gln Gln Pro Ala Val Ser Leu Ser Phe Ser Ser Thr Gln Arg
545                 550                 555                 560

Pro Glu Ala Gln Gln Gln Leu Gln Gln Arg Ser Ala Ala Val Thr Gln
                565                 570                 575

Pro Gln Leu Gly Ala Gly Pro Gln Leu Pro Gly Gln Ile Ser Ser Ala
            580                 585                 590

Gln Val Thr Ser Gln His Leu Leu Arg Glu Ser Ser Val Ile Ser Thr
        595                 600                 605

Gln Gly Pro Lys Pro Met Arg Ser Ser Gln Leu Met Gln Ser Ser Gly
    610                 615                 620

Arg Ser
625


<210> SEQ ID NO 14
<211> LENGTH: 481
<212> TYPE: PRT
<213> ORGANISM: Homo sapiens

<400> SEQUENCE: 14

Asn Ser Arg Arg Pro Ala Leu Arg Ala Ala Ala Ala Gly Ala Arg Pro
1               5                   10                  15

Ala Gly Gly Pro Gly Ser Gln Pro Pro Glu Gln His Leu Gly Gly His
            20                  25                  30

Ile Leu Gln Ser Leu Asp Gly Phe Val Phe Ala Leu Asn Gln Glu Gly
        35                  40                  45

Lys Phe Leu Tyr Ile Ser Glu Thr Val Ser Ile Tyr Leu Gly Leu Ser
    50                  55                  60
```

-continued

```
Gln Val Glu Met Thr Gly Ser Ser Val Phe Asp Tyr Ile His Pro Gly
65                  70                  75                  80

Asp His Ser Glu Val Leu Glu Gln Leu Gly Leu Arg Thr Pro Thr Pro
                85                  90                  95

Gly Pro Pro Thr Pro Pro Ser Val Ser Ser Ser Ser Ser Ser Ser Ser
            100                 105                 110

Ser Leu Ala Asp Thr Pro Glu Ile Glu Ala Ser Leu Thr Lys Val Pro
        115                 120                 125

Pro Ser Ser Leu Val Gln Glu Arg Ser Phe Phe Val Arg Met Lys Ser
    130                 135                 140

Thr Leu Thr Lys Arg Gly Leu His Val Lys Ala Ser Gly Tyr Lys Val
145                 150                 155                 160

Ile His Val Thr Gly Arg Leu Arg Ala His Ala Leu Gly Leu Val Ala
                165                 170                 175

Leu Gly His Thr Leu Pro Pro Ala Pro Leu Ala Glu Leu Pro Leu His
            180                 185                 190

Gly His Met Ile Val Phe Arg Leu Ser Leu Gly Leu Thr Ile Leu Ala
        195                 200                 205

Cys Glu Ser Arg Val Ser Asp His Met Asp Leu Gly Pro Ser Glu Leu
    210                 215                 220

Val Gly Arg Ser Cys Tyr Gln Phe Val His Gly Gln Asp Ala Thr Arg
225                 230                 235                 240

Ile Arg Gln Ser His Val Asp Leu Leu Asp Lys Gly Gln Val Met Thr
                245                 250                 255

Gly Tyr Tyr Arg Trp Leu Gln Arg Ala Gly Gly Phe Val Trp Leu Gln
            260                 265                 270

Ser Val Ala Thr Val Ala Gly Ser Gly Lys Ser Pro Gly Glu His His
        275                 280                 285

Val Leu Trp Val Ser His Val Leu Ser Gln Ala Glu Gly Gly Gln Thr
    290                 295                 300

Pro Leu Asp Ala Phe Gln Leu Pro Ala Ser Val Ala Cys Glu Glu Ala
305                 310                 315                 320

Ser Ser Pro Gly Pro Glu Pro Thr Glu Pro Glu Pro Pro Thr Glu Gly
                325                 330                 335

Lys Gln Ala Ala Pro Ala Glu Asn Glu Ala Pro Gln Thr Gln Gly Lys
            340                 345                 350

Arg Ile Lys Val Glu Pro Gly Pro Arg Glu Thr Lys Gly Ser Glu Asp
        355                 360                 365

Ser Gly Asp Glu Asp Pro Ser Ser His Pro Ala Thr Pro Arg Pro Glu
    370                 375                 380

Phe Thr Ser Val Ile Arg Ala Gly Val Leu Lys Gln Asp Pro Val Arg
385                 390                 395                 400

Pro Trp Gly Leu Ala Pro Pro Gly Asp Pro Pro Pro Thr Leu Leu His
                405                 410                 415

Ala Gly Phe Leu Pro Pro Val Val Arg Gly Leu Cys Thr Pro Gly Thr
            420                 425                 430

Ile Arg Tyr Gly Pro Ala Glu Leu Gly Leu Val Tyr Pro His Leu Gln
        435                 440                 445

Arg Leu Gly Pro Gly Pro Ala Leu Pro Glu Ala Phe Tyr Pro Pro Leu
    450                 455                 460

Gly Leu Pro Tyr Pro Gly Pro Ala Gly Thr Arg Leu Pro Arg Lys Gly
465                 470                 475                 480

Asp
```

<210> SEQ ID NO 15
<211> LENGTH: 691
<212> TYPE: PRT
<213> ORGANISM: Homo sapiens

<400> SEQUENCE: 15

```
Met Ala Pro Thr Lys Pro Ser Phe Gln Gln Asp Pro Ser Arg Arg Glu
1               5                   10                  15

Arg Leu Gln Ala Leu Arg Lys Glu Lys Ser Arg Asp Ala Ala Arg Ser
            20                  25                  30

Arg Arg Gly Lys Glu Asn Phe Glu Phe Tyr Glu Leu Ala Lys Leu Leu
        35                  40                  45

Pro Leu Pro Ala Ala Ile Thr Ser Gln Leu Asp Lys Ala Ser Ile Ile
    50                  55                  60

Arg Leu Thr Ile Ser Tyr Leu Lys Met Arg Asp Phe Ala Asn Gln Gly
65                  70                  75                  80

Asp Pro Pro Trp Asn Leu Arg Met Glu Gly Pro Pro Pro Asn Thr Ser
                85                  90                  95

Val Lys Gly Ala Gln Arg Arg Arg Ser Pro Ser Ala Leu Ala Ile Glu
            100                 105                 110

Val Phe Glu Ala His Leu Gly Ser His Ile Leu Gln Ser Leu Asp Gly
        115                 120                 125

Phe Val Phe Ala Leu Asn Gln Glu Gly Lys Phe Leu Tyr Ile Ser Glu
    130                 135                 140

Thr Val Ser Ile Tyr Leu Gly Leu Ser Gln Val Glu Leu Thr Gly Ser
145                 150                 155                 160

Ser Val Phe Asp Tyr Val His Pro Gly Asp His Val Glu Met Ala Glu
                165                 170                 175

Gln Leu Gly Met Lys Leu Pro Pro Gly Arg Gly Leu Leu Ser Gln Gly
            180                 185                 190

Thr Ala Glu Asp Gly Ala Ser Ser Ala Ser Ser Ser Ser Gln Ser Glu
        195                 200                 205

Thr Pro Glu Pro Val Glu Ser Thr Ser Pro Ser Leu Leu Thr Thr Asp
    210                 215                 220

Asn Thr Leu Glu Arg Ser Phe Phe Ile Arg Met Lys Ser Thr Leu Thr
225                 230                 235                 240

Lys Arg Gly Val His Ile Lys Ser Ser Gly Tyr Lys Val Ile His Ile
                245                 250                 255

Thr Gly Arg Leu Arg Leu Arg Val Ser Leu Ser His Gly Arg Thr Val
            260                 265                 270

Pro Ser Gln Ile Met Gly Leu Val Val Val Ala His Ala Leu Pro Pro
        275                 280                 285

Pro Thr Ile Asn Glu Val Arg Ile Asp Cys His Met Phe Val Thr Arg
    290                 295                 300

Val Asn Met Asp Leu Asn Ile Ile Tyr Cys Glu Asn Arg Ile Ser Asp
305                 310                 315                 320

Tyr Met Asp Leu Thr Pro Val Asp Ile Val Gly Lys Arg Cys Tyr His
                325                 330                 335

Phe Ile His Ala Glu Asp Val Glu Gly Ile Arg His Ser His Leu Asp
            340                 345                 350

Leu Leu Asn Lys Gly Gln Cys Val Thr Lys Tyr Tyr Arg Trp Met Gln
        355                 360                 365

Lys Asn Gly Gly Tyr Ile Trp Ile Gln Ser Ser Ala Thr Ile Ala Ile
```

```
    370                 375                 380

Asn Ala Lys Asn Ala Asn Glu Lys Asn Ile Ile Trp Val Asn Tyr Leu
385                 390                 395                 400

Leu Ser Asn Pro Glu Tyr Lys Asp Thr Pro Met Asp Ile Ala Gln Leu
                405                 410                 415

Pro His Leu Pro Glu Lys Thr Ser Glu Ser Ser Glu Thr Ser Asp Ser
            420                 425                 430

Glu Ser Asp Ser Lys Asp Thr Ser Gly Ile Thr Glu Asp Asn Glu Asn
        435                 440                 445

Ser Lys Ser Asp Glu Lys Gly Asn Gln Ser Glu Asn Ser Glu Asp Pro
    450                 455                 460

Glu Pro Asp Arg Lys Lys Ser Gly Asn Ala Cys Asp Asn Asp Met Asn
465                 470                 475                 480

Cys Asn Asp Asp Gly His Ser Ser Ser Asn Pro Asp Ser Arg Asp Ser
                485                 490                 495

Asp Asp Ser Phe Glu His Ser Asp Phe Glu Asn Pro Lys Ala Gly Glu
            500                 505                 510

Asp Gly Phe Gly Ala Leu Gly Ala Met Gln Ile Lys Val Glu Arg Tyr
        515                 520                 525

Val Glu Ser Glu Ser Asp Leu Arg Leu Gln Asn Cys Glu Ser Leu Thr
    530                 535                 540

Ser Asp Ser Ala Lys Asp Ser Asp Ser Ala Gly Glu Ala Gly Ala Gln
545                 550                 555                 560

Ala Ser Ser Lys His Gln Lys Arg Lys Lys Arg Arg Lys Arg Gln Lys
                565                 570                 575

Gly Gly Ser Ala Ser Arg Arg Arg Leu Ser Ser Ala Ser Ser Pro Gly
            580                 585                 590

Gly Leu Asp Ala Gly Leu Val Glu Pro Pro Arg Leu Leu Ser Ser Pro
        595                 600                 605

Asn Ser Ala Ser Val Leu Lys Ile Lys Thr Glu Ile Ser Glu Pro Ile
    610                 615                 620

Asn Phe Asp Asn Asp Ser Ser Ile Trp Asn Tyr Pro Pro Asn Arg Glu
625                 630                 635                 640

Ile Ser Arg Asn Glu Ser Pro Tyr Ser Met Thr Lys Pro Pro Ser Ser
                645                 650                 655

Glu His Phe Pro Ser Pro Gln Gly Gly Gly Gly Gly Gly Gly Gly Gly
            660                 665                 670

Gly Gly Leu His Val Ala Ile Pro Asp Ser Val Leu Thr Pro Pro Gly
        675                 680                 685

Ala Asp Gly
    690


<210> SEQ ID NO 16
<211> LENGTH: 662
<212> TYPE: PRT
<213> ORGANISM: mus

<400> SEQUENCE: 16

Met Asp Trp Asp Gln Asp Arg Ser Asn Thr Glu Leu Arg Lys Glu Lys
1               5                   10                  15

Ser Arg Asp Ala Ala Arg Ser Arg Arg Ser Gln Glu Thr Glu Val Leu
            20                  25                  30

Tyr Gln Leu Ala His Thr Leu Pro Phe Ala Arg Gly Val Ser Ala His
        35                  40                  45
```

-continued

```
Leu Asp Lys Ala Ser Ile Met Arg Leu Thr Ile Ser Tyr Leu Arg Met
    50                  55                  60

His Arg Leu Cys Ala Ala Gly Glu Trp Asn Gln Val Glu Lys Gly Gly
65                  70                  75                  80

Glu Pro Leu Asp Ala Cys Tyr Leu Lys Ala Leu Glu Gly Phe Val Met
                85                  90                  95

Val Leu Thr Ala Glu Gly Asp Met Ala Tyr Leu Ser Glu Asn Val Ser
            100                 105                 110

Lys His Leu Gly Leu Ser Gln Leu Glu Leu Ile Gly His Ser Ile Phe
        115                 120                 125

Asp Phe Ile His Pro Cys Asp Gln Glu Glu Leu Gln Asp Ala Leu Thr
    130                 135                 140

Pro Arg Pro Asn Leu Ser Lys Lys Lys Leu Glu Ala Pro Thr Glu Arg
145                 150                 155                 160

His Phe Ser Leu Arg Met Lys Ser Thr Leu Thr Ser Arg Gly Arg Thr
                165                 170                 175

Leu Asn Leu Lys Ala Ala Thr Trp Lys Val Leu His Cys Ser Gly His
            180                 185                 190

Met Arg Ala Tyr Lys Pro Pro Ala Gln Thr Ser Pro Ala Gly Ser Pro
        195                 200                 205

Arg Ser Glu Pro Pro Leu Gln Cys Leu Val Leu Ile Cys Glu Ala Ile
    210                 215                 220

Pro His Pro Ala Ser Leu Glu Pro Pro Leu Gly Arg Gly Ala Phe Leu
225                 230                 235                 240

Ser Arg His Ser Leu Asp Met Lys Phe Thr Tyr Cys Asp Glu Arg Ile
                245                 250                 255

Ala Glu Val Ala Gly Tyr Ser Pro Asp Asp Leu Ile Gly Cys Ser Ala
            260                 265                 270

Tyr Glu Tyr Ile His Ala Leu Asp Ser Asp Ala Val Ser Arg Ser Ile
        275                 280                 285

His Thr Leu Leu Ser Lys Gly Gln Ala Val Thr Gly Gln Tyr Arg Phe
    290                 295                 300

Leu Ala Arg Thr Gly Gly Tyr Leu Trp Thr Gln Thr Gln Ala Thr Val
305                 310                 315                 320

Val Ser Gly Gly Arg Gly Pro Gln Ser Glu Ser Ile Ile Cys Val His
                325                 330                 335

Phe Leu Ile Ser Arg Val Glu Glu Thr Gly Val Val Leu Ser Leu Glu
            340                 345                 350

Gln Thr Glu Gln His Thr Arg Arg Pro Pro Arg Leu Ser Ala Ser Ser
        355                 360                 365

Gln Lys Gly Ile Pro Gly Asn Ser Val Asp Ser Pro Ala Pro Arg Ile
    370                 375                 380

Leu Ala Phe Leu His Pro Pro Ala Leu Ser Glu Ala Ser Leu Ala Ala
385                 390                 395                 400

Asp Pro Arg Arg Phe Cys Ser Pro Asp Leu Arg Arg Leu Met Ala Pro
                405                 410                 415

Ile Leu Asp Gly Pro Pro Pro Ala Ala Thr Pro Ser Thr Pro Gln Ala
            420                 425                 430

Thr Arg Arg Pro Gln Ser Pro Leu Pro Ala Asp Leu Pro Asp Lys Leu
        435                 440                 445

Ala Val Gly Leu Glu Asn Ala His Arg Leu Ser Thr Ala Gln Lys Asn
    450                 455                 460

Lys Thr Val Glu Thr Asp Leu Asp Ile Ala Gln Asp Ser Asp Thr Leu
```

-continued

```
465                 470                 475                 480

Asp Leu Glu Met Leu Ala Pro Tyr Ile Ser Met Asp Asp Asp Phe Gln
                485                 490                 495

Leu Asn Ser Ser Glu Gln Leu Pro Lys Val His Arg Arg Pro Pro Arg
            500                 505                 510

Val Ala Arg Arg Pro Arg Ala Arg Ser Phe His Gly Leu Ser Pro Pro
        515                 520                 525

Ile Pro Glu Pro Ser Leu Leu Pro Arg Trp Gly Ser Asp Pro Arg Leu
    530                 535                 540

Asn Cys Ser Ser Pro Ser Arg Gly Asp Arg Pro Thr Ala Ser Leu Met
545                 550                 555                 560

Pro Gly Thr Arg Lys Arg Ala Leu Ala Gln Ser Ser Glu Asp Lys Gly
                565                 570                 575

Leu Glu Leu Leu Glu Ile Lys Pro Pro Lys Arg Ser Pro Arg Leu Glu
            580                 585                 590

Pro Gly Ser Phe Leu Leu Pro Pro Leu Ser Leu Ser Phe Leu Leu Gln
        595                 600                 605

Gly Arg Gln Leu Leu Gly Asn Gln Gln Asp Pro Arg Ala Pro Leu Val
    610                 615                 620

His Ser His Glu Pro Leu Gly Leu Ala Pro Ser Leu Leu Ser Leu Cys
625                 630                 635                 640

Gln His Glu Glu Thr Val Gln Pro Arg Asn His Phe Pro Pro Ala Ala
                645                 650                 655

Gly Leu Gly Gln Thr His
            660


<210> SEQ ID NO 17
<211> LENGTH: 1246
<212> TYPE: PRT
<213> ORGANISM: Homo sapiens

<400> SEQUENCE: 17

Met Asn Gly Tyr Ala Glu Phe Pro Pro Ser Pro Ser Asn Pro Thr Lys
1               5                   10                  15

Glu Pro Val Glu Pro Gln Pro Ser Gln Val Pro Leu Gln Glu Asp Val
            20                  25                  30

Asp Met Ser Ser Gly Ser Ser Gly His Glu Thr Asn Glu Asn Cys Ser
        35                  40                  45

Thr Gly Arg Asp Ser Gln Gly Ser Asp Cys Asp Asp Ser Gly Lys Glu
    50                  55                  60

Leu Gly Met Leu Val Glu Pro Pro Asp Ala Arg Gln Ser Pro Asp Thr
65                  70                  75                  80

Phe Ser Leu Met Met Ala Lys Ser Glu His Asn Pro Ser Thr Ser Gly
                85                  90                  95

Cys Ser Ser Asp Gln Ser Ser Lys Val Asp Thr His Lys Glu Leu Ile
            100                 105                 110

Lys Thr Leu Lys Glu Leu Lys Val His Leu Pro Ala Asp Lys Lys Ala
        115                 120                 125

Lys Gly Lys Ala Ser Thr Leu Ala Thr Leu Lys Tyr Ala Leu Arg Ser
    130                 135                 140

Val Lys Gln Val Lys Ala Asn Glu Glu Tyr Tyr Gln Leu Leu Met Ser
145                 150                 155                 160

Ser Glu Gly His Pro Cys Gly Ala Asp Val Pro Ser Tyr Thr Val Glu
                165                 170                 175
```

-continued

```
Glu Met Glu Ser Val Thr Ser Glu His Ile Val Lys Asn Ala Asp Met
            180                 185                 190

Phe Ala Val Ala Val Ser Leu Val Ser Gly Lys Ile Leu Tyr Ile Ser
        195                 200                 205

Asp Gln Val Ala Ser Ile Phe His Cys Lys Arg Asp Ala Phe Ser Asp
    210                 215                 220

Ala Lys Phe Val Glu Phe Leu Ala Pro His Asp Val Gly Val Phe His
225                 230                 235                 240

Ser Phe Thr Ser Pro Tyr Lys Leu Pro Leu Trp Ser Met Cys Ser Gly
                245                 250                 255

Ala Asp Ser Phe Thr Gln Glu Cys Met Glu Glu Lys Ser Phe Phe Cys
            260                 265                 270

Arg Val Ser Val Arg Lys Ser His Glu Asn Glu Ile Arg Tyr His Pro
        275                 280                 285

Phe Arg Met Thr Pro Tyr Leu Val Lys Val Arg Asp Gln Gln Gly Ala
    290                 295                 300

Glu Ser Gln Leu Cys Cys Leu Leu Leu Ala Glu Arg Val His Ser Gly
305                 310                 315                 320

Tyr Glu Ala Pro Arg Ile Pro Pro Glu Lys Arg Ile Phe Thr Thr Thr
                325                 330                 335

His Thr Pro Asn Cys Leu Phe Gln Asp Val Asp Glu Arg Ala Val Pro
            340                 345                 350

Leu Leu Gly Tyr Leu Pro Gln Asp Leu Ile Glu Thr Pro Val Leu Val
        355                 360                 365

Gln Leu His Pro Ser Asp Arg Pro Leu Met Leu Ala Ile His Lys Lys
    370                 375                 380

Ile Leu Gln Ser Gly Gly Gln Pro Phe Asp Tyr Ser Pro Ile Arg Phe
385                 390                 395                 400

Arg Ala Arg Asn Gly Glu Tyr Ile Thr Leu Asp Thr Ser Trp Ser Ser
                405                 410                 415

Phe Ile Asn Pro Trp Ser Arg Lys Ile Ser Phe Ile Ile Gly Arg His
            420                 425                 430

Lys Val Arg Val Gly Pro Leu Asn Glu Asp Val Phe Ala Ala His Pro
        435                 440                 445

Cys Thr Glu Glu Lys Ala Leu His Pro Ser Ile Gln Glu Leu Thr Glu
    450                 455                 460

Gln Ile His Arg Leu Leu Leu Gln Pro Val Pro His Ser Gly Ser Ser
465                 470                 475                 480

Gly Tyr Gly Ser Leu Gly Ser Asn Gly Ser His Glu His Leu Met Ser
                485                 490                 495

Gln Thr Ser Ser Ser Asp Ser Asn Gly His Glu Asp Ser Arg Arg Arg
            500                 505                 510

Arg Ala Glu Ile Cys Lys Asn Gly Asn Lys Thr Lys Asn Arg Ser His
        515                 520                 525

Tyr Ser His Glu Ser Gly Glu Gln Lys Lys Lys Ser Val Thr Glu Met
    530                 535                 540

Gln Thr Asn Pro Pro Ala Glu Lys Lys Ala Val Pro Ala Met Glu Lys
545                 550                 555                 560

Asp Ser Leu Gly Val Ser Phe Pro Glu Glu Leu Ala Cys Lys Asn Gln
                565                 570                 575

Pro Thr Cys Ser Tyr Gln Gln Ile Ser Cys Leu Asp Ser Val Ile Arg
            580                 585                 590

Tyr Leu Glu Ser Cys Asn Glu Ala Ala Thr Leu Lys Arg Lys Cys Glu
```

-continued

```
        595                 600                 605

Phe Pro Ala Asn Val Pro Ala Leu Arg Ser Ser Asp Lys Arg Lys Ala
    610                 615                 620

Thr Val Ser Pro Gly Pro His Ala Gly Glu Ala Glu Pro Pro Ser Arg
625                 630                 635                 640

Val Asn Ser Arg Thr Gly Val Gly Thr His Leu Thr Ser Leu Ala Leu
                645                 650                 655

Pro Gly Lys Ala Glu Ser Val Ala Ser Leu Thr Ser Gln Cys Ser Tyr
            660                 665                 670

Ser Ser Thr Ile Val His Val Gly Asp Lys Lys Pro Gln Pro Glu Leu
        675                 680                 685

Glu Met Val Glu Asp Ala Ala Ser Gly Pro Glu Ser Leu Asp Cys Leu
    690                 695                 700

Ala Gly Pro Ala Leu Ala Cys Gly Leu Ser Gln Glu Lys Glu Pro Phe
705                 710                 715                 720

Lys Lys Leu Gly Leu Thr Lys Glu Val Leu Ala Ala His Thr Gln Lys
                725                 730                 735

Glu Glu Gln Ser Phe Leu Gln Lys Phe Lys Glu Ile Arg Lys Leu Ser
            740                 745                 750

Ile Phe Gln Ser His Cys His Tyr Tyr Leu Gln Glu Arg Ser Lys Gly
        755                 760                 765

Gln Pro Ser Glu Arg Thr Ala Pro Gly Leu Arg Asn Thr Ser Gly Ile
    770                 775                 780

Asp Ser Pro Trp Lys Lys Thr Gly Lys Asn Arg Lys Leu Lys Ser Lys
785                 790                 795                 800

Arg Val Lys Pro Arg Asp Ser Ser Glu Ser Thr Gly Ser Gly Gly Pro
                805                 810                 815

Val Ser Ala Arg Pro Pro Leu Val Gly Leu Asn Ala Thr Ala Trp Ser
            820                 825                 830

Pro Ser Asp Thr Ser Gln Ser Ser Cys Pro Ala Val Pro Phe Pro Ala
        835                 840                 845

Pro Val Pro Ala Ala Tyr Ser Leu Pro Val Phe Pro Ala Pro Gly Thr
    850                 855                 860

Val Ala Ala Pro Pro Ala Pro Pro His Ala Ser Phe Thr Val Pro Ala
865                 870                 875                 880

Val Pro Val Asp Leu Gln His Gln Phe Ala Val Gln Pro Pro Pro Phe
                885                 890                 895

Pro Ala Pro Leu Ala Pro Val Met Ala Phe Met Leu Pro Ser Tyr Ser
            900                 905                 910

Phe Pro Ser Gly Thr Pro Asn Leu Pro Gln Ala Phe Phe Pro Ser Gln
        915                 920                 925

Pro Gln Phe Pro Ser His Pro Thr Leu Thr Ser Glu Met Ala Ser Ala
    930                 935                 940

Ser Gln Pro Glu Phe Pro Ser Arg Thr Ser Ile Pro Arg Gln Pro Cys
945                 950                 955                 960

Ala Cys Pro Ala Thr Arg Ala Thr Pro Pro Ser Ala Met Gly Arg Ala
                965                 970                 975

Ser Pro Pro Leu Phe Gln Ser Arg Ser Ser Ser Pro Leu Gln Leu Asn
            980                 985                 990

Leu Leu Gln Leu Glu Glu Ala Pro  Glu Gly Gly Thr Gly  Ala Met Gly
        995                 1000                1005

Thr Thr  Gly Ala Thr Glu Thr  Ala Ala Val Gly Ala  Asp Cys Lys
    1010                1015                1020
```

-continued

```
Pro Gly  Thr Ser Arg Asp Gln  Gln Pro Lys Ala Pro  Leu Thr Arg
    1025                 1030                 1035

Asp Glu  Pro Ser Asp Thr Gln  Asn Ser Asp Ala Leu  Ser Thr Ser
    1040                 1045                 1050

Ser Gly  Leu Leu Asn Leu Leu  Leu Asn Glu Asp Leu  Cys Ser Ala
    1055                 1060                 1065

Ser Gly  Ser Ala Ala Ser Glu  Ser Leu Gly Ser Gly  Ser Leu Gly
    1070                 1075                 1080

Cys Asp  Ala Ser Pro Ser Gly  Ala Gly Ser Ser Asp  Thr Ser His
    1085                 1090                 1095

Thr Ser  Lys Tyr Phe Gly Ser  Ile Asp Ser Ser Glu  Asn Asn His
    1100                 1105                 1110

Lys Ala  Lys Met Asn Thr Gly  Met Glu Glu Ser Glu  His Phe Ile
    1115                 1120                 1125

Lys Cys  Val Leu Gln Asp Pro  Ile Trp Leu Leu Met  Ala Asp Ala
    1130                 1135                 1140

Asp Ser  Ser Val Met Met Thr  Tyr Gln Leu Pro Ser  Arg Asn Leu
    1145                 1150                 1155

Glu Ala  Val Leu Lys Glu Asp  Arg Glu Lys Leu Lys  Leu Leu Gln
    1160                 1165                 1170

Lys Leu  Gln Pro Gly Ser Arg  Arg Val Arg Ser Arg  Ser Cys Ala
    1175                 1180                 1185

Arg Ser  Thr Ser Gly Cys Arg  Arg Ala Ala Cys Pro  Gln Pro Ser
    1190                 1195                 1200

Thr Trp  Gln Asn Val Phe Thr  Val Lys Thr Arg Lys  Lys Val Ile
    1205                 1210                 1215

Phe Ala  Tyr His Met Arg Lys  Ile Phe Leu Leu Trp  Asp Ser Ala
    1220                 1225                 1230

Lys Cys  Arg Thr Pro Lys Lys  Thr Lys Met Asp Pro  Pro
    1235                 1240                 1245


<210> SEQ ID NO 18
<211> LENGTH: 585
<212> TYPE: PRT
<213> ORGANISM: Homo sapiens

<400> SEQUENCE: 18

Met Gly Ser Phe Ser Ser His Met Thr Glu Phe Pro Arg Lys Arg Lys
1               5                   10                  15

Gly Ser Asp Ser Asp Pro Ser Gln Ser Gly Ile Met Thr Glu Lys Val
            20                  25                  30

Val Glu Lys Leu Ser Gln Asn Pro Leu Thr Tyr Leu Leu Ser Thr Arg
        35                  40                  45

Ile Glu Ile Ser Ala Ser Ser Gly Ser Arg Glu Ala His Ser Gln Thr
    50                  55                  60

Glu Lys Arg Arg Arg Asp Lys Met Asn Asn Leu Ile Glu Glu Leu Ser
65                  70                  75                  80

Ala Met Ile Pro Gln Cys Asn Pro Met Ala Arg Lys Leu Asp Lys Leu
                85                  90                  95

Thr Val Leu Arg Met Ala Val Gln His Leu Arg Ser Leu Lys Gly Leu
            100                 105                 110

Thr Asn Ser Tyr Val Gly Ser Asn Tyr Arg Pro Ser Phe Leu Gln Asp
        115                 120                 125

Asn Glu Leu Arg His Leu Ile Leu Lys Thr Ala Glu Gly Phe Leu Phe
```

-continued

```
    130                 135                 140

Val Val Gly Cys Glu Arg Gly Lys Ile Leu Phe Val Ser Lys Ser Val
145                 150                 155                 160

Ser Lys Ile Leu Asn Tyr Asp Gln Ala Ser Leu Thr Gly Gln Ser Leu
                165                 170                 175

Phe Asp Phe Leu His Pro Lys Asp Val Ala Lys Val Lys Glu Gln Leu
            180                 185                 190

Ser Ser Phe Asp Ile Ser Pro Arg Glu Lys Leu Ile Asp Thr Lys Thr
        195                 200                 205

Gly Leu Gln Val His Ser Asn Leu His Ala Gly Arg Thr Arg Val Tyr
    210                 215                 220

Phe Gly Ser Arg Arg Ser Phe Phe Cys Arg Ile Lys Ser Cys Lys Ile
225                 230                 235                 240

Ser Val Lys Glu Glu His Gly Cys Leu Pro Asn Ser Lys Lys Lys Glu
                245                 250                 255

His Arg Lys Phe Tyr Thr Ile His Cys Thr Gly Tyr Leu Arg Ser Trp
            260                 265                 270

Pro Pro Asn Ile Val Gly Met Glu Glu Glu Arg Asn Ser Lys Lys Asp
        275                 280                 285

Asn Ser Asn Phe Thr Cys Leu Val Ala Ile Gly Arg Leu Gln Pro Tyr
    290                 295                 300

Ile Val Pro Gln Asn Ser Gly Glu Ile Asn Val Lys Pro Thr Glu Phe
305                 310                 315                 320

Ile Thr Arg Phe Ala Val Asn Gly Lys Phe Val Tyr Val Asp Gln Arg
                325                 330                 335

Ala Thr Ala Ile Leu Gly Tyr Leu Pro Gln Glu Leu Leu Gly Thr Ser
            340                 345                 350

Cys Tyr Glu Tyr Phe His Gln Asp Asp His Asn Asn Leu Thr Asp Lys
        355                 360                 365

His Lys Ala Val Leu Gln Ser Lys Glu Lys Ile Leu Thr Asp Ser Tyr
    370                 375                 380

Lys Phe Arg Ala Lys Asp Gly Ser Phe Val Thr Leu Lys Ser Gln Trp
385                 390                 395                 400

Phe Ser Phe Thr Asn Pro Trp Thr Lys Glu Leu Glu Tyr Ile Val Ser
                405                 410                 415

Val Asn Thr Leu Val Leu Gly His Ser Glu Pro Gly Glu Ala Ser Phe
            420                 425                 430

Leu Pro Cys Ser Ser Gln Ser Ser Glu Glu Ser Ser Arg Gln Ser Cys
        435                 440                 445

Met Ser Val Pro Gly Met Ser Thr Gly Thr Val Leu Gly Ala Gly Ser
    450                 455                 460

Ile Gly Thr Asp Ile Ala Asn Glu Ile Leu Asp Leu Gln Arg Leu Gln
465                 470                 475                 480

Ser Ser Ser Tyr Leu Asp Asp Ser Ser Pro Thr Gly Leu Met Lys Asp
                485                 490                 495

Thr His Thr Val Asn Cys Arg Ser Met Ser Asn Lys Glu Leu Phe Pro
            500                 505                 510

Pro Ser Pro Ser Glu Met Gly Glu Leu Glu Ala Thr Arg Gln Asn Gln
        515                 520                 525

Ser Thr Val Ala Val His Ser His Glu Pro Leu Leu Ser Asp Gly Ala
    530                 535                 540

Gln Leu Asp Phe Asp Ala Leu Cys Asp Asn Asp Asp Thr Ala Met Ala
545                 550                 555                 560
```

```
Ala Phe Met Asn Tyr Leu Glu Ala Glu Gly Gly Leu Gly Asp Pro Gly
                565                 570                 575

Asp Phe Ser Asp Ile Gln Trp Thr Leu
            580                 585


<210> SEQ ID NO 19
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 19

cgaggtcgac ggtatcg                                                    17


<210> SEQ ID NO 20
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 20

tctagaacta gtggatc                                                    17


<210> SEQ ID NO 21
<211> LENGTH: 37
<212> TYPE: DNA
<213> ORGANISM: Artificial Sequence
<220> FEATURE:
<223> OTHER INFORMATION: Synthetic Sequence

<400> SEQUENCE: 21

cccaagctta cgcgtggtct ttgaagtcaa cctcacc                              37


<210> SEQ ID NO 22
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 22

agctcgaaat taaccctcac taaagg                                          26


<210> SEQ ID NO 23
<211> LENGTH: 41
<212> TYPE: DNA
<213> ORGANISM: Artificial Sequence
<220> FEATURE:
<223> OTHER INFORMATION: Synthetic Sequence

<400> SEQUENCE: 23

cgggatcctt acacattggt gttggtacag atgatgtact c                         41


<210> SEQ ID NO 24
<211> LENGTH: 34
<212> TYPE: DNA
<213> ORGANISM: Artificial Sequence
<220> FEATURE:
<223> OTHER INFORMATION: Synthetic Sequence

<400> SEQUENCE: 24

gcgtcgactg atgagcagcg gcgccaacat cacc                                 34
```

<210> SEQ ID NO 25
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 25
gataagaatg cggccgcaga tctgggtccg aagcacacg 39

<210> SEQ ID NO 26
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 26
cattacttat ctagagctcg 20

<210> SEQ ID NO 27
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 27
cgggatcctc atggcggcga ctactgccaa cc 32

<210> SEQ ID NO 28
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 28
gacagttgct tgagtttcaa cc 22

<210> SEQ ID NO 29
<211> LENGTH: 24
<212> TYPE: DNA
<213> ORGANISM: Artificial Sequence
<220> FEATURE:
<223> OTHER INFORMATION: Oligonucleotide

<400> SEQUENCE: 29
ttatgagctt gctcatcagt tgcc 24

<210> SEQ ID NO 30
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 30
cctcacacgc aaatagctga tgg 23

<210> SEQ ID NO 31
<211> LENGTH: 35
<212> TYPE: DNA
<213> ORGANISM: Artificial Sequence
<220> FEATURE:
<223> OTHER INFORMATION: Oligonucleotide

<400> SEQUENCE: 31
ccgctcgagt gatgagcagc ggcgccaaca tcacc 35

<210> SEQ ID NO 32
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 32
ccgctcgagt ggcagctaca ggaatccacc 30

<210> SEQ ID NO 33
<211> LENGTH: 28
<212> TYPE: DNA
<213> ORGANISM: Artificial Sequence
<220> FEATURE:
<223> OTHER INFORMATION: Oligonucleotide

<400> SEQUENCE: 33
gcggtaccgg gaccgattca ccatggag 28

<210> SEQ ID NO 34
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 34
tcgagctggg cagggtacgt ggcaaggc 28

<210> SEQ ID NO 35
<211> LENGTH: 28
<212> TYPE: DNA
<213> ORGANISM: Artificial Sequence
<220> FEATURE:
<223> OTHER INFORMATION: Oligonucleotide

<400> SEQUENCE: 35
tcgagccttg ccacgtaccc tgcccagc 28

<210> SEQ ID NO 36
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 36
gtaaaacgac ggccagt 17

<210> SEQ ID NO 37
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 37
ggaaacagct atgaccatg 19

<210> SEQ ID NO 38

<211> LENGTH: 28
<212> TYPE: DNA
<213> ORGANISM: Artificial Sequence
<220> FEATURE:
<223> OTHER INFORMATION: Synthetic Sequence

<400> SEQUENCE: 38
tcgagctggg cagggtgcgt ggcaaggc 28

<210> SEQ ID NO 39
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 39
tcgagccttg ccacgcaccc tgcccagc 28

<210> SEQ ID NO 40
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 40
tcgagctggg caggtcacgt ggcaaggc 28

<210> SEQ ID NO 41
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 41
tcgagccttg ccacgtgacc tgcccagc 28

<210> SEQ ID NO 42
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 42
tcgagctggg caggttgcgt ggcaaggc 28

<210> SEQ ID NO 43
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 43
tcgagccttg ccacgcaacc tgcccagc 28

<210> SEQ ID NO 44
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 44
tactggccac ttactacctg acc 23

<210> SEQ ID NO 45
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 45
aaccagagcc atttttgaga ct 22

<210> SEQ ID NO 46
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 46
gctctagagg ccacagcgac aatgacagc 29

<210> SEQ ID NO 47
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 47
gatcggaggt gttctatgag c 21

<210> SEQ ID NO 48
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 48
ttaggatgca ggtagtcaaa ca 22

<210> SEQ ID NO 49
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 49
gttctccatg gaccagactg a 21

<210> SEQ ID NO 50
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 50
cgggtaccct gggccctacg tgctgtctc 29

<210> SEQ ID NO 51
<211> LENGTH: 32
<212> TYPE: DNA

<213> ORGANISM: Artificial Sequence
<220> FEATURE:
<223> OTHER INFORMATION: Synthetic Sequence

<400> SEQUENCE: 51
cggctagcct ctggcctccc tctccttgat ga 32

<210> SEQ ID NO 52
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 52
ctgggagcct gcctgccttc a 21

<210> SEQ ID NO 53
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 53
cccaaggaga ggcgtgat 18

<210> SEQ ID NO 54
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 54
gggatcctcg tcgccactg 19

<210> SEQ ID NO 55
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 55
atgcagtacc cagacggatt tc 22

<210> SEQ ID NO 56
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 56
tgcacggtca ccaacagag 19

<210> SEQ ID NO 57
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 57
ttgccagtcg catgatgga 19

<210> SEQ ID NO 58
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 58
ctgaacagcc atccttag 18

<210> SEQ ID NO 59
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 59
agcttgccct acgtgctgtc tcag 24

<210> SEQ ID NO 60
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 60
aattctgaga cagcacgtag ggca 24

<210> SEQ ID NO 61
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 61
agaggtgctg cccaggtaga a 21

<210> SEQ ID NO 62
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 62
caatgatgag ggaaacactg 20

<210> SEQ ID NO 63
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 63
cgggatcccg tcaactggag atgagcaagg ag 32

<210> SEQ ID NO 64
<211> LENGTH: 23
<212> TYPE: DNA
<213> ORGANISM: Artificial Sequence
<220> FEATURE:

<223> OTHER INFORMATION: Synthetic Sequence

<400> SEQUENCE: 64
ctgcaaaaat ccgatgacct ctt 23

<210> SEQ ID NO 65
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 65
cgggcagcag cgtcttc 17

<210> SEQ ID NO 66
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 66
gcgtccgcag ccccagttg 19

<210> SEQ ID NO 67
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 67
ttcaatgttc tcatcaaaga gc 22

<210> SEQ ID NO 68
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 68
gaacagtttt atagatgaat tggc 24

<210> SEQ ID NO 69
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 69
gaggtgtttc aattcatcgt ct 22

<210> SEQ ID NO 70
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 70
gggatccgtg accgattcac catggag 27

-continued

<210> SEQ ID NO 71
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 71
ctgcaggtca cacaacgtaa ttcacaca 28

<210> SEQ ID NO 72
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 72
gggatccgta tgacagctga caaggag 27

<210> SEQ ID NO 73
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 73
ggtcgacgtc acaggacgta gttgacaca 29

<210> SEQ ID NO 74
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 74
gaatccatga gcaaggaggc cgtg 24

<210> SEQ ID NO 75
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 75
ggtcgacgtc aaacaacagt gttagttga 29

<210> SEQ ID NO 76
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 76
gggatgcgta tggatgaaga tgagaaagac 30

<210> SEQ ID NO 77
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 77
ggtcgacgct agaccgagtg tgtgca 26

<210> SEQ ID NO 78
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 78
gacagtatca cgcctctcct t 21

<210> SEQ ID NO 79
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 79
agcggcgtcg ggataaaatg a 21

<210> SEQ ID NO 80
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 80
atgctgaact gtgccgaaaa ctgt 24

<210> SEQ ID NO 81
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 81
gaacagtggg gtgggtcctc ttt 23

<210> SEQ ID NO 82
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 82
ggaattctga gtctgaac 18

<210> SEQ ID NO 83
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 83
ggaattccac gctcagg 17

<210> SEQ ID NO 84
<211> LENGTH: 47

```
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (19)..(31)
<223> OTHER INFORMATION: nucleotide can be either a, c, g or t

<400> SEQUENCE: 84

ggaattctga gtctgaacnn nnnnnnnnn ncctgagcgt ggattcc                  47


<210> SEQ ID NO 85
<211> LENGTH: 46
<212> TYPE: DNA
<213> ORGANISM: Artificial Sequence
<220> FEATURE:
<223> OTHER INFORMATION: Synthetic Sequence

<400> SEQUENCE: 85

gatcggacac gtgaccattg gtcacgtgtc cattggacac gtgacc                  46


<210> SEQ ID NO 86
<211> LENGTH: 46
<212> TYPE: DNA
<213> ORGANISM: Artificial Sequence
<220> FEATURE:
<223> OTHER INFORMATION: Synthetic Sequence

<400> SEQUENCE: 86

gatcggtcac gtgtccaatg gacacgtgac caatggtcac gtgtcc                  46


<210> SEQ ID NO 87
<211> LENGTH: 46
<212> TYPE: DNA
<213> ORGANISM: Artificial Sequence
<220> FEATURE:
<223> OTHER INFORMATION: Synthetic Sequence

<400> SEQUENCE: 87

gatcggatac gtgaccattg gttacgtgtc cattggatac gtgacc                  46


<210> SEQ ID NO 88
<211> LENGTH: 46
<212> TYPE: DNA
<213> ORGANISM: Artificial Sequence
<220> FEATURE:
<223> OTHER INFORMATION: Synthetic Sequence

<400> SEQUENCE: 88

gatcggtcac gtatccaatg gacacgtaac caatggtcac gtatcc                  46


<210> SEQ ID NO 89
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 89

tcgagctggg caggtaaggt ggcaaggc                                      28


<210> SEQ ID NO 90
<211> LENGTH: 28
<212> TYPE: DNA
<213> ORGANISM: Artificial Sequence
<220> FEATURE:
```

<223> OTHER INFORMATION: Synthetic Sequence

<400> SEQUENCE: 90
tcgagccttg ccacgttacc tgcccagc 28

<210> SEQ ID NO 91
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 91
tcgagctggg caggtgaggt ggcaaggc 28

<210> SEQ ID NO 92
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 92
tcgagccttg ccacgtcacc tgcccagc 28

<210> SEQ ID NO 93
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 93
tcgagctggg cagggtaggt ggcaaggc 28

<210> SEQ ID NO 94
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 94
tcgagccttg ccacgtaccc tgcccagc 28

<210> SEQ ID NO 95
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 95
gccatggcgt tggggtgcag 20

<210> SEQ ID NO 96
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 96
actgtgtcca atgagctcca g 21

<210> SEQ ID NO 97
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 97
gcctccatca tgcgcctcac aatcagc 27

<210> SEQ ID NO 98
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 98
ccccgttact gcctggccct tgctca 26

<210> SEQ ID NO 99
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 99
agccgagggg gtctgcgagt atgttgc 27

<210> SEQ ID NO 100
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 100
gctgctgacc ctcgccgttt ctgtagt 27

<210> SEQ ID NO 101
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 101
gtcgacgcca ccatggactg ggaccaagac agg 33

<210> SEQ ID NO 102
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 102
ggatcctcag tgggtctggc ccaagcc 27

<210> SEQ ID NO 103
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 103
gcggggtgct gggagtggct gctac 25

<210> SEQ ID NO 104
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 104
gccttcctgc acccgccttc cctgag 26

<210> SEQ ID NO 105
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 105
gcggccgcaa aaaacaagac cgtggagaca 30

<210> SEQ ID NO 106
<211> LENGTH: 42
<212> TYPE: DNA
<213> ORGANISM: Artificial Sequence
<220> FEATURE:
<223> OTHER INFORMATION: Synthetic Sequence

<400> SEQUENCE: 106
gccctgggag aatagctgtt ggactttggg caattgctca ct 42

<210> SEQ ID NO 107
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 107
gcggccgcct attctgaaaa ggggggaaa 29

<210> SEQ ID NO 108
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 108
ccatcctaat acgactcact atagggc 27

<210> SEQ ID NO 109
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 109
actcactata gggctcgagc ggc 23

<210> SEQ ID NO 110
<211> LENGTH: 14

-continued

<212> TYPE: DNA
<213> ORGANISM: Artificial Sequence
<220> FEATURE:
<223> OTHER INFORMATION: Synthetic Sequence

<400> SEQUENCE: 110
ggggcacgtg acac 14

<210> SEQ ID NO 111
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 111
ggtacacgtg accc 14

<210> SEQ ID NO 112
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 112
tgaacacgtg accc 14

<210> SEQ ID NO 113
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 113
tgaacacgtg actc 14

<210> SEQ ID NO 114
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 114
gggccacgtg acct 14

<210> SEQ ID NO 115
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 115
gggacacgtg accg 14

<210> SEQ ID NO 116
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 116
ctaacacgtg accg 14

<210> SEQ ID NO 117
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 117
gaaccacgtg agct 14

<210> SEQ ID NO 118
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 118
tgaacacgtg acac 14

<210> SEQ ID NO 119
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 119
gggtcacgtg actc 14

<210> SEQ ID NO 120
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: nucleotide can be either g or t
<220> FEATURE:
<221> NAME/KEY: misc_feature
<222> LOCATION: (3)..(3)
<223> OTHER INFORMATION: nucleotide can be either a or g

<400> SEQUENCE: 120
ngnacacgtg accc 14

<210> SEQ ID NO 121
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 121
gccctacgtg accc 14

<210> SEQ ID NO 122
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 122

-continued

```
gccctacgtg ttcc                                                          14


<210> SEQ ID NO 123
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 123

gccctacgtg accc                                                          14


<210> SEQ ID NO 124
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (4)..(4)
<223> OTHER INFORMATION: nucleotide can be a, c, t or g
<220> FEATURE:
<221> NAME/KEY: misc_feature
<222> LOCATION: (11)..(11)
<223> OTHER INFORMATION: nucleotide can be a, c, t or g

<400> SEQUENCE: 124

gcancacgtg nacc                                                          14


<210> SEQ ID NO 125
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 125

Asp Asn Asp Gln Gly Ser Ser Ser Pro Ser Asn Asp Glu Ala Ala Cys
1               5                   10                  15


<210> SEQ ID NO 126
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 126

Lys Asp Lys Gly Ser Ser Leu Glu Pro Arg Gln His Phe Asn Ala Leu
1               5                   10                  15

Asp Val Gly Cys
            20
```